(12) United States Patent
Gray et al.

(10) Patent No.: US 9,180,127 B2
(45) Date of Patent: Nov. 10, 2015

(54) TYPE II RAF KINASE INHIBITORS

(75) Inventors: Nathanael S. Gray, Boston, MA (US);
Hwan G. Choi, Chestnut Hill, MA (US);
Xianming Deng, Brookline, MA (US);
Jianming Zhang, Belmont, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/519,826

(22) PCT Filed: Dec. 29, 2010

(86) PCT No.: PCT/US2010/062310
§ 371 (c)(1),
(2), (4) Date: Nov. 1, 2012

(87) PCT Pub. No.: WO2011/090738
PCT Pub. Date: Jul. 28, 2011

(65) Prior Publication Data
US 2013/0040949 A1 Feb. 14, 2013

Related U.S. Application Data

(60) Provisional application No. 61/290,884, filed on Dec. 29, 2009.

(51) Int. Cl.
| | | |
|---|---|---|
| C07D 471/02 | (2006.01) |
| C07D 405/00 | (2006.01) |
| A61K 31/44 | (2006.01) |
| A61K 31/496 | (2006.01) |
| C07D 487/04 | (2006.01) |
| C07D 471/04 | (2006.01) |

(52) U.S. Cl.
CPC ............ *A61K 31/496* (2013.01); *C07D 471/04* (2013.01); *C07D 487/04* (2013.01)

(58) Field of Classification Search
USPC ............ 544/336, 357, 407; 546/268.1, 276.4, 546/113; 548/517, 518; 514/300
See application file for complete search history.

(56) References Cited

U.S. PATENT DOCUMENTS

| | | | |
|---|---|---|---|
| 6,939,874 B2 | 9/2005 | Harmange et al. | |
| 7,115,617 B2 | 10/2006 | Buchanan et al. | |
| 8,765,747 B2 | 7/2014 | Choi et al. | |
| 2006/0189627 A1* | 8/2006 | Laird et al. ............... | 514/253.05 |
| 2007/0093537 A1* | 4/2007 | Hynes et al. .................. | 514/370 |
| 2007/0185171 A1 | 8/2007 | Germain et al. | |
| 2007/0281907 A1 | 12/2007 | Watkins | |
| 2008/0039629 A1 | 2/2008 | Ramesh et al. | |
| 2008/0103167 A1 | 5/2008 | Bebernitz et al. | |
| 2008/0214501 A1 | 9/2008 | Pan et al. | |
| 2009/0054392 A1 | 2/2009 | Pelletier et al. | |
| 2009/0054405 A1 | 2/2009 | Booker et al. | |
| 2009/0105250 A1* | 4/2009 | Sim et al. .................... | 514/235.8 |
| 2011/0212053 A1 | 9/2011 | Qian et al. | |
| 2012/0088766 A1 | 4/2012 | Choi et al. | |
| 2012/0165309 A1 | 6/2012 | Takahashi et al. | |
| 2014/0309249 A1 | 10/2014 | Gray et al. | |

FOREIGN PATENT DOCUMENTS

| | | | |
|---|---|---|---|
| CA | 2503646 A1 | 5/2004 | |
| CA | 2550128 A1 | 6/2005 | |
| CA | 2563212 A1 | 10/2005 | |
| EP | 1935890 A1 | 6/2008 | |
| JP | 2007-500725 A | 1/2007 | |
| JP | 2009-510110 A | 3/2009 | |
| JP | 2011-516533 A | 5/2011 | |
| WO | WO 02/076986 A1 | 10/2002 | |
| WO | WO 02/079197 A1 | 10/2002 | |
| WO | WO 02/080926 A1 | 10/2002 | |
| WO | WO 02/096905 A1 | 12/2002 | |
| WO | WO 02/102800 A1 | 12/2002 | |
| WO | WO 2004/005283 A1 | 1/2004 | |
| WO | WO 2004/039796 A1 | 5/2004 | |
| WO | 2004-078757 A2 | 9/2004 | |
| WO | WO 2004078757 A2 * | 9/2004 | ........... C07D 471/04 |
| WO | WO 2004/087699 A2 | 10/2004 | |
| WO | WO 2004/100868 A2 | 11/2004 | |
| WO | WO 2005/011597 A2 | 2/2005 | |
| WO | WO 2005/058891 A1 | 6/2005 | |
| WO | WO 2005/097790 A1 | 10/2005 | |
| WO | WO 2006/031806 A2 | 3/2006 | |
| WO | WO 2006024834 A1 * | 3/2006 | |
| WO | WO 2006040568 A1 * | 4/2006 | |
| WO | WO 2007/035428 A1 | 3/2007 | |
| WO | WO 2007/042786 A2 | 4/2007 | |
| WO | WO 2007/129195 A2 | 11/2007 | |
| WO | WO 2007/138277 A1 | 12/2007 | |
| WO | WO 2008/068171 A1 | 6/2008 | |

(Continued)

OTHER PUBLICATIONS

Y. Choi et al., "Discovery and Structural Analysis of Eph Receptor Tyrosine Kinase Inhbitors", Bioorg. Med. Chem. Lett. Aug. 1, 2009, pp. 4467-4470.
International Search Report and Written Opinion for PCT/US2012/065618, mailed Mar. 19, 2013.
International Preliminary Report on Patentability for PCT/US2012/065618, mailed May 30, 2014.
International Search Report and Written Opinion for PCT/US2013/065708, mailed Feb. 4, 2014.

(Continued)

*Primary Examiner* — Paul Zarek
*Assistant Examiner* — George W Kosturko
(74) *Attorney, Agent, or Firm* — Wolf, Greenfield & Sacks, P.C.

(57) ABSTRACT

The present invention relates to novel compounds which are able to modulate b-raf kinases, and the use of such compounds in the treatment of various diseases, disorders or conditions.

8 Claims, 52 Drawing Sheets

(56) References Cited

FOREIGN PATENT DOCUMENTS

| | | | |
|---|---|---|---|
| WO | WO 2008124393 A1 * | 10/2008 | |
| WO | 2008-144253 A1 | 11/2008 | |
| WO | WO 2008144253 A1 * | 11/2008 | |
| WO | WO 2008/151183 A1 | 12/2008 | |
| WO | WO 2009/017822 A2 | 2/2009 | |
| WO | 2009-155017 A2 | 12/2009 | |
| WO | WO 2010/008847 A2 | 1/2010 | |
| WO | WO 2010/051781 A1 | 5/2010 | |
| WO | WO 2010/125799 A1 | 11/2010 | |
| WO | WO 2013/074986 A1 | 5/2013 | |
| WO | WO 2013/154778 A1 | 10/2013 | |
| WO | WO 2014/063068 A1 | 4/2014 | |

OTHER PUBLICATIONS

International Search Report and Written Opinion for PCT/US2013/065689, mailed Mar. 4, 2014.
International Search Report and Written Opinion for PCT/US2013/065698, mailed Feb. 20, 2014.
International Search Report and Written Opinion for PCT/US2014/061232, mailed Dec. 23, 2014.
Extended European Search Report for EP 10786967.9, mailed Oct. 23, 2012.
International Search Report and Written Opinion for PCT/US2010/038518, mailed Aug. 6, 2010.
International Preliminary Report on Patentability for PCT/US2010/038518, mailed Dec. 22, 2011.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Stanovnik et al., The Tautomerism of Heterocycles: Substituent Tautomerism of Six-Membered Ring Heterocycles. Advances in Heterocyclic Chemistry. 2006;91:1-134.
Zhang et al., Discovery of potent and selective covalent inhibitors of JNK. Chem Biol. Jan. 27, 2012;19(1):140-54. doi: 10.1016/j.chembiol.2011.11.010.
Extended European Search Report for EP 10844280.7, mailed Apr. 17, 2013.
International Search Report and Written Opinion for PCT/US2010/062310, mailed Oct. 14, 2011.
International Preliminary Report on Patentability for PCT/US2010/062310, mailed Jul. 12, 2012.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.

* cited by examiner

FIG. 1A: Table 1. The following compounds were produced by using the corresponding starting compounds according to method similar to that described in Example 1.

| Structure | Name | ¹H NMR, and/or MS(m/z) |
|---|---|---|
| I-2 | N-(3-((5-aminopyrazin-2-yl)methylamino)-4-methylphenyl)-3-(trifluoromethyl)benzamide | MS m/z : 402 [M+1]. |
| I-3 | N-(3-((5-aminopyrazin-2-yl)methylamino)-4-methylphenyl)-3-(4-methyl-1H-imidazol-1-yl)-5-(trifluoromethyl)benzamide | ¹H NMR (600 MHz, CDCl$_3$) δ 8.30 (s, 1H), 8.11 (s, 1H), 8.04 (d, J = 7.2 Hz, 2H), 7.94 (s, 1H), 7.85 (s, 1H), 7.73 (s, 1H), 7.26 (s, 1H), 7.08 (s, 2H), 7.04 (d, J = 7.8 Hz, 1H), 6.92 (d, J = 7.2 Hz, 1H), 4.56 (s, 2H), 4.36 (s, 2H), 2.26 (s, 3H), 2.18 (s, 3H). MS m/z : 482 [M+1]. |
| I-4 | 5-((3,5-dimethoxyphenylamino)methyl)pyrazin-2-amine | MS m/z : 261 [M+1]. |

FIG. 1B

| Structure | Name | Data |
|---|---|---|
| I-5 | 5-((2-chlorophenylamino)methyl)pyrazin-2-amine | $^1$H NMR (600 MHz, CDCl$_3$) δ 8.03 (s, 1H), 7.98 (s, 1H), 7.27 (dd, J = 1.2, 6.6 Hz, 1H), 7.11 (dt, J = 1.2, 7.2 Hz, 1H), 6.68-6.63 (m, 2H), 5.08 (brs, 1H), 4.59 (s, 2H), 4.39 (s, 2H). MS m/z : 235 [M+1]. |
| I-6 | N-((5-aminopyrazin-2-yl)methyl)quinolin-3-amine | MS m/z : 252 [M+1]. |
| I-7 | 5-((2-chloro-6-methylphenylamino)methyl)pyrazin-2-amine | MS m/z : 249 [M+1]. |
| I-8 | methyl 3-((5-aminopyrazin-2-yl)methylamino)-4-methylbenzoate | $^1$H NMR (600 MHz, CDCl$_3$) δ 8.06 (s, 1H), 7.99 (s, 1H), 7.37 (d, J = 7.8 Hz, 1H), 7.32 (s, 1H), 7.12 (d, J = 7.8 Hz, 1H), 4.57 (brs, 2H), 4.41 (s, 2H), 3.88 (s, 3H), 2.24 (s, 3H). MS m/z : 273 [M+1]. |

FIG. 1C

| | | |
|---|---|---|
| 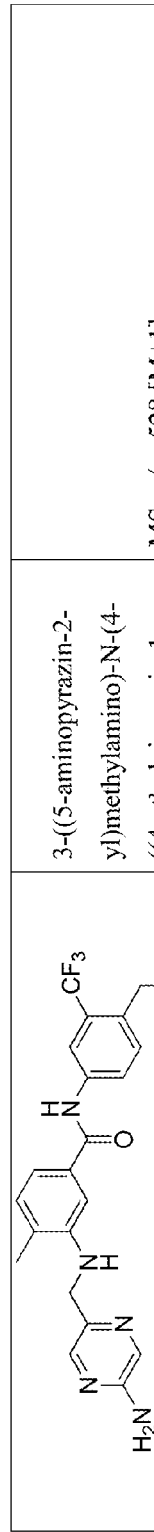<br>I-9 | 3-((5-aminopyrazin-2-yl)methylamino)-N-(4-((4-ethylpiperazin-1-yl)methyl)-3-(trifluoromethyl)phenyl)-4-methylbenzamide | MS m/z : 528 [M+1]. |
| 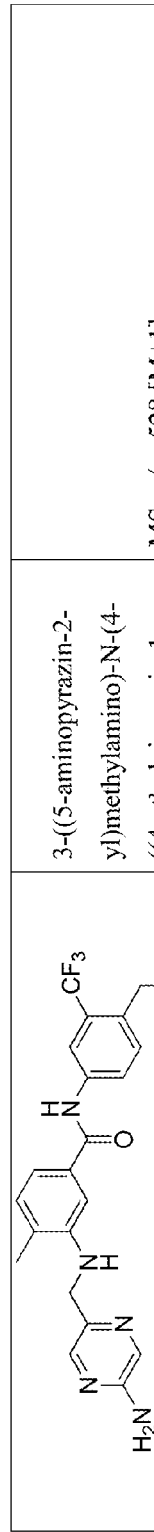<br>I-10 | N-(3-((5-aminopyrazin-2-yl)methoxy)-5-methoxyphenyl)-3-(trifluoromethyl)benzamide | $^1$H NMR (600 MHz, CDCl$_3$) $\delta$ 8.08 (s, 1H), 8.05 (s, 1H), 7.97 (s, J = 7.8 Hz, 1H), 7.92 (s, 1H), 7.80 (s, 1H), 7.74 (d, J = 7.2 Hz, 1H), 7.56 (t, J = 7.8 Hz, 1H), 6.90-6.87 (m, 2H), 6.32 (t, J = 1.8 Hz, 1H), 4.99 (s, 2H), 4.69 (s, 2H), 3.73 (s, 3H). MS m/z : 419 [M+1]. |
| 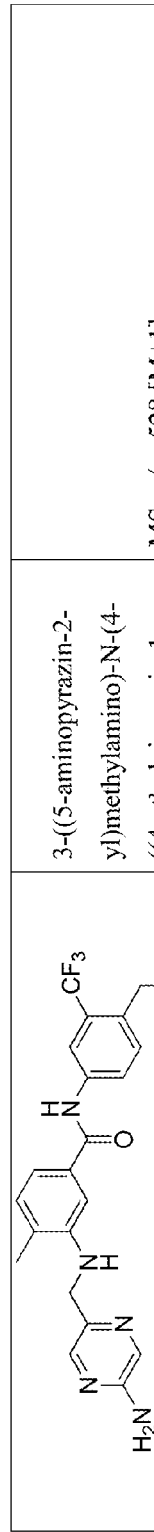<br>I-11 | N-(3-((5-aminopyrazin-2-yl)methoxy)-4-methylphenyl)-3-(trifluoromethyl)benzamide | $^1$H NMR (600 MHz, CDCl$_3$) $\delta$ 8.08 (s, 1H), 8.04 (s, 1H), 7.98 (d, J = 7.2 Hz, 2H), 7.95 (s, 1H), 7.85 (s, 1H), 7.74 (d, J = 7.8 Hz, 1H), 7.56 (t, J = 7.8 Hz, 1H), 7.37 (s, 1H), 7.08 (d, J = 7.8 Hz, 1H), 6.92 (d, J = 7.2 Hz, 1H), 5.05 (s, 2H), 2.18 (s, 3H). MS m/z : 403 [M+1]. |

FIG. 1D
| | | |
|---|---|---|
| 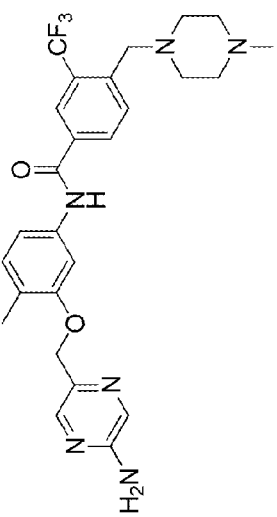 I-12 | N-(3-((5-aminopyrazin-2-yl)methoxy)-4-methylphenyl)-4-((4-methylpiperazin-1-yl)methyl)-3-(trifluoromethyl)benzamide | $^1$H NMR (600 MHz, CDCl$_3$) δ 8.22 (s, 1H), 8.12 (s, 1H), 8.02-7.98 (m, 2H), 7.96 (d, J = 7.8 Hz, 1H), 7.81 (d, J = 8.4 Hz, 1H), 7.50 (s, 1H), 7.12 (d, J = 7.8 Hz, 1H), 7.01 (dd, J = 1.8, 7.8 Hz, 1H), 5.11 (s, 2H), 4.60 (s, 2H), 3.72 (s, 2H), 2.60-2.40 (m, 8H), 2.32 (s, 3H), 2.24 (s, 3H). MS m/z : 515 [M+1]. |
| 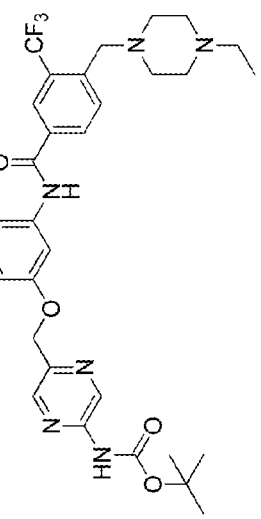 I-13 | tert-butyl 5-((3-(4-((4-ethylpiperazin-1-yl)methyl)-3-(trifluoromethyl)benzamido)phenoxy)methyl)pyrazin-2-ylcarbamate | MS m/z : 615 [M+1]. |

| | | |
|---|---|---|
| | N-(3-((5-aminopyrazin-2-yl)methoxy)phenyl)-4-(((4-ethylpiperazin-1-yl)methyl)-3-(trifluoromethyl)benzamide | $^1$H NMR (600 MHz, DMSO-$d_6$) δ 10.42 (s, 1H), 8.24 (s, 1H), 8.21 (d, $J$ = 7.8 Hz, 1H), 8.02 (d, $J$ = 1.2 Hz, 1H), 7.91 (dd, $J$ = 3.6, 4.8 Hz, 2H), 7.47 (t, $J$ = 2.4 Hz, 1H), 7.33 (d, $J$ = 8.4 Hz, 1H), 7.26 (t, $J$ = 8.4 Hz, 1H), 6.79 (dd, $J$ = 1.8, 8.4 Hz, 1H), 5.71 (s, 2H), 4.94 (s, 2H), 3.78 (s, 2H), 3.50-3.35 (m, 2H), 3.12 (q, $J$ = 7.2 Hz, 2H), 2.99-2.91 (m, 4H), 2.45-2.38 (m, 2H), 1.19 (t, $J$ = 7.2 Hz, 3H). MS $m/z$ : 515 [M+1]. |
| I-14 | | |

FIG. 2A: Table 2. The following compounds were produced by using the corresponding starting compounds according to method similar to that described in Example 2.

| Structure | Name | $^1$H NMR, and/or MS(m/z) |
|---|---|---|
| 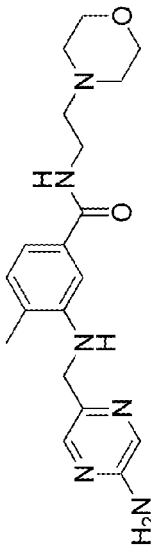<br>II-2 | 3-((5-aminopyrazin-2-yl)methylamino)-4-methyl-N-(2-morpholinoethyl)benzamide | $^1$H NMR (600 MHz, CDCl$_3$) δ 7.99 (s, 1H), 7.94 (d, J = 1.2 Hz, 1H), 7.12 (d, J = 1.8 Hz, 1H), 7.07 (d, J = 7.8 Hz, 1H), 6.97 (dd, J = 1.8, 7.8 Hz, 1H), 6.80 (s, 1H), 4.78 (s, 2H), 4.49 (s, 1H), 4.37 (d, J = 3.6 Hz, 2H), 3.69 (t, J = 4.2 Hz, 4H), 3.52 (q, J = 5.4 Hz, 2H), 2.57 (t, J = 5.4 Hz, 2H), 2.48 (brs, 4H), 2.20 (s, 3H). MS m/z : 371 [M+1]. |
| 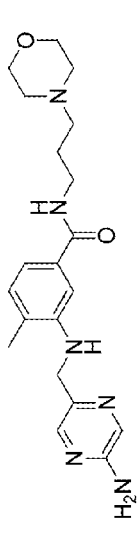<br>II-3 | 3-((5-aminopyrazin-2-yl)methylamino)-4-methyl-N-(3-morpholinopropyl)benzamide | $^1$H NMR (600 MHz, CDCl$_3$) δ 8.02 (d, J = 1.2 Hz, 1H), 7.96 (d, J = 1.2 Hz, 1H), 7.63 (s, 1H), 7.19 (d, J = 1.8 Hz, 1H), 7.08 (d, J = 7.8 Hz, 1H), 6.98 (dd, J = 1.8, 7.8 Hz, 1H), 4.66 (s, 2H), 4.49 (s, 1H), 4.40 (s, 2H), 3.71-3.68 (m, 4H), 3.53 (q, J = 6.0 Hz, 2H), 2.53 (t, J = 5.4 Hz, 2H), 2.49 (brs, 4H), 2.21 (s, 3H), 1.80-1.76 (m, 2H). MS m/z : 385 [M+1]. |

FIG. 2B

| Structure | Name | Data |
|---|---|---|
| II-4 | 3-((5-aminopyrazin-2-yl)methylamino)-4-methyl-N-(3-(4-methylpiperazin-1-yl)propyl)benzamide | MS m/z : 398 [M+1]. |
| II-5 | 3-((5-aminopyrazin-2-yl)methylamino)-4-methyl-N-(2-(pyrrolidin-1-yl)ethyl)benzamide | $^1$H NMR (600 MHz, CDCl$_3$) δ 8.05 (d, $J$ = 1.2 Hz, 1H), 7.96 (d, $J$ 1.8 Hz, 1H), 7.28 (brs, 1H), 7.18 (d, $J$ = 1.2 Hz, 1H), 7.09-7.05 (m, 2H), 4.60 (s, 2H), 4.49 (t, $J$ = 4.8 Hz, 1H), 4.40 (d, $J$ = 4.8 Hz, 2H), 3.62 (q, $J$ = 5.4 Hz, 2H), 2.89 (t, $J$ = 6.0 Hz, 2H), 2.78 (s, br, 4H), 2.21 (s, 3H), 1.88-1.84 (m, 4H). MS m/z : 355 [M+1]. |
| II-6 | 3-((5-aminopyrazin-2-yl)methylamino)-N-(2-hydroxyethyl)-4-methylbenzamide | $^1$H NMR (600 MHz, CDCl$_3$) δ 7.99 (d, $J$ = 1.2 Hz, 1H), 7.91 (d, $J$ = 1.8 Hz, 1H), 7.06 (d, $J$ = 1.2 Hz, 1H), 7.03 (d, $J$ = 7.8 Hz, 1H), 6.94 (dd, $J$ = 1.2, 7.8 Hz, 1H), 4.48 (s, 2H), 4.45 (s, 1H), 4,34 (s, 2H), 3.76 (t, $J$ = 4.8 Hz, 2H), 3.54 (dd, $J$ = 5.4, 9.6 Hz, 2H), 2.16 (s, 3H). MS m/z : 302 [M+1]. |

FIG. 3A: Table 3. The following compounds were produced by using the corresponding starting compounds according to method similar to that described in Example 3.

| Structure | Name | $^1$H NMR, and/or MS(m/z) |
|---|---|---|
| III-2 | 3-((5-acetamidopyrazin-2-yl)methylamino)-5-methoxy-N-(4-((4-methylpiperazin-1-yl)methyl)-3-(trifluoromethyl)phenyl)benzamide | $^1$H NMR (600 MHz, CD$_3$OD) δ 9.50 (d, J = 1.2 Hz, 1H), 8.54 (d, J = 1.2 Hz, 1H), 8.11 (d, J = 2.4 Hz, 1H), 7.96 (dd, J = 1.8, 8.4 Hz, 1H), 7.75 (d, J = 8.4 Hz, 1H), 6.82 (t, J = 1.8 Hz, 1H), 6.78 (t, J 1.8 Hz, 1H), 6.48 (t, J = 1.8 Hz, 1H), 4.74 (s, 2H), 3.85 (s, 2H), 3.80 (s, 3H), 3.73-3.69 (m, 2H), 3.53-3.49 (m, 2H), 3.16 (s, 3H), 3.05-3.00 (m, 2H), 2.90-2.85 (m, 2H), 2.21 (s, 3H). MS m/z : 572 [M+1]. |
| III-3 | methyl 5-((5-(4-((4-ethylpiperazin-1-yl)methyl)-3-(trifluoromethyl)benzamido)-2-methylphenylamino)methyl)pyrazin-2-ylcarbamate | $^1$H NMR (600 MHz, CD$_3$OD) δ 9.22 (s, 1H), 8.37 (s, 1H), 8.02 (s, 1H), 7.85 (s, 1H), 7.65 (s, 1H), 7.14-7.03 (m, 3H), 4.61 (s, 2H), 3.80-3.60 (m, 5H), 3.55 (s, 2H), 3.42-3.38 (m, 2H), 3.21 (s, 2H), 2.90-2.79 (m, 4H), 2.11 (s, 3H), 1.39 (brs, 3H). MS m/z : 586 [M+1]. |

FIG. 3B

| Structure | Name | 1H NMR |
|---|---|---|
| 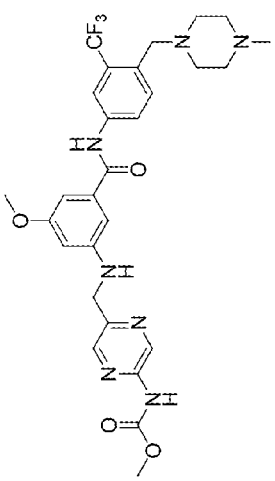 III-4 | methyl 5-((3-methoxy-5-(4-((4-methylpiperazin-1-yl)methyl)-3-(trifluoromethyl)phenylcarbamoyl)phenylamino)methyl)pyrazin-2-yl)carbamate | 1H NMR (600 MHz, CD3OD) δ 9.23 (s, 1H), 8.38 (s, 1H), 8.01 (s, 1H), 7.86 (d, J = 8.4 Hz, 1H), 7.65 (d, J = 8.4 Hz, 1H), 6.72 (s, 1H), 6.68 (s, 1H), 6.39 (s, 1H), 4.62 (s, 2H), 3.75-3.70 (m, 8H), 3.60 (t, J = 9.0 Hz, 2H), 3.42-3.40 (m, 2H), 3.05 (s, 3H), 2.93-2.90 (m, 2H), 2.79-2.75 (m, 2H). MS m/z: 588 [M+1]. |
| 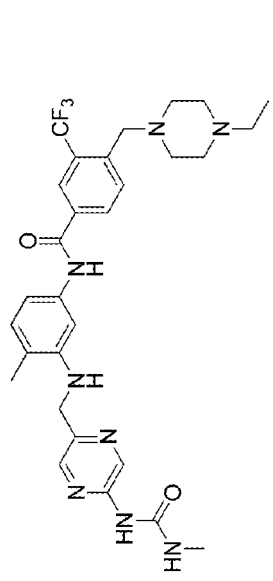 III-5 | 4-((4-ethylpiperazin-1-yl)methyl)-N-(4-methyl-3-((5-(3-methylureido)pyrazin-2-yl)methylamino)phenyl)-3-(trifluoromethyl)benzamide | 1H NMR (600 MHz, CD3OD) δ 8.73 (s, 1H), 8.38 (d, J = 1.2 Hz, 1H), 8.12 (d, J = 1.8 Hz, 1H), 7.94 (dd, J = 1.8, 8.4 Hz, 1H), 7.74 (d, J = 8.4 Hz, 1H), 7.24 (t, J = 1.8 Hz, 1H), 7.18 (dd, J = 1.8, 7.8 Hz, 1H), 7.11 (d, J = 7.8 Hz, 1H), 4.67 (s, 2H), 3.84 (s, 2H), 3.65-3.62 (m, 2H), 3.52-3.45 (m, 4H), 2.99-2.96 (m, 2H), 2.89-2.86 (m, 5H), 2.21 (s, 3H), 1.49 (t, J = 7.2 Hz, 3H). MS m/z: 585 [M+1]. |

FIG. 3C

| | | |
|---|---|---|
| 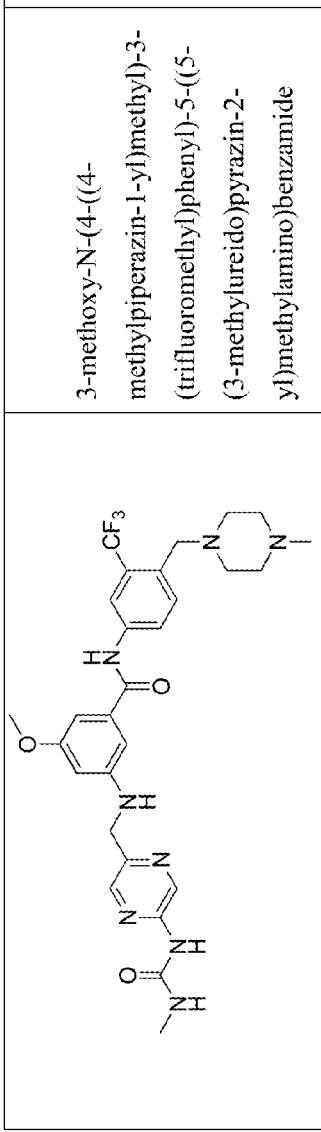 III-6 | 3-methoxy-N-(4-((4-methylpiperazin-1-yl)methyl)-3-(trifluoromethyl)phenyl)-5-(((5-(3-methylureido)pyrazin-2-yl)methylamino)benzamide | $^1$H NMR (600 MHz, DMSO-$d_6$ or CDCl$_3$) $\delta$, MS $m/z$ : 587 [M+1]. |
| 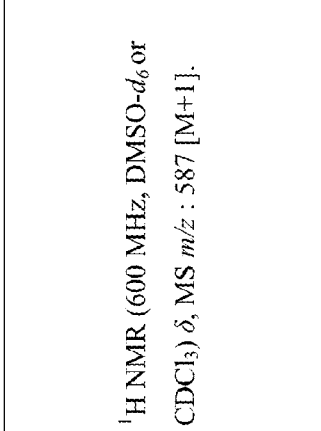 III-7 | 3-((5-(cyclopropanecarboxamido)pyrazin-2-yl)methylamino)-5-methoxy-N-(3-(trifluoromethyl)phenyl)benzamide | $^1$H NMR (600 MHz, CDCl$_3$) $\delta$ 9.46 (s, 1H), 8.29 (s, 1H), 8.24 (s, 1H), 7.99 (s, 1H), 7.94 (s, 1H), 7.82 (d, $J$ = 7.2 Hz, 1H), 7.46 (t, $J$ = 7.8 Hz, 1H), 7.38 (d, $J$ = 7.2 Hz, 1H), 6.75 (s, 1H), 6.72 (s, 1H), 6.35 (d, $J$ 1.8 Hz, 1H), 4.46 (s, 2H), 3.79 (s, 3H), 1.69-1.56 (m, 1H), 1.13 (dd, $J$ = 3.0, 4.2 Hz, 2H), 0.93 (dd, $J$ = 3.0, 7.8 Hz, 2H). MS $m/z$ : 486 [M+1]. |

| | | |
|---|---|---|
| (III-8 structure) | N-(3-((5-(cyclopropanecarboxamido)pyrazin-2-yl)methylamino)-4-methylphenyl)-3-(trifluoromethyl)benzamide | MS m/z : 470 [M+1]. |
| (III-9 structure) | N-(3-((5-(cyclopropanecarboxamido)pyrazin-2-yl)methylamino)-4-((4-ethylpiperazin-1-yl)methyl)-3-(trifluoromethyl)benzamide | $^1$H NMR (600 MHz, DMSO-$d_6$) δ 11.42 (s, 1H), 10.40 (s, 1H), 9.47 (d, J = 1.2 Hz, 1H), 8.66 (d, J = 1.2 Hz, 1H), 8.28 (d, J = 1.8 Hz, 1H), 8.15 (d, J = 7.8 Hz, 1H), 7.77 (d, J = 8.4 Hz, 1H), 7.34 (s, 1H), 7.27 (d, J = 7.8 Hz, 1H), 7.19 (d, J = 7.2 Hz, 1H), 4.80 (s, 2H), 3.86 (s, 2H), 3.63-3.60 (m, 2H), 3.53-3.48 (m, 4H), 3.05-2.98 (m, 2H), 2.89-2.86 (m, 2H), 2.22 (s, 3H), 2.14-2.10 (m, 1H), 1.43 (t, J = 7.2 Hz, 3H), 0.96-0.93 (m, 4H). MS m/z : 596 [M+1]. |

| | 3-(5-(cyclopropanecarboxamido)pyrazin-2-yl)methylamino)-4-methyl-N-(4-((4-methylpiperazin-1-yl)methyl)-3-(trifluoromethyl)phenyl)benzamide | MS m/z : 582 [M+1]. |

III-10

FIG. 4A: Table 4. The following compounds were produced by using the corresponding starting compounds according to method similar to that described in Example 4.
| Structure | Name | $^1$H NMR, and/or MS(m/z) |
|---|---|---|
| 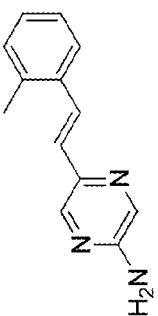<br>IV-2 | (E)-5-(2-methylstyryl)pyrazin-2-amine | MS m/z : 212 [M+1]. |
| 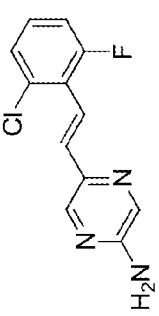<br>IV-3 | (E)-5-(2-chloro-6-fluorostyryl)pyrazin-2-amine | MS m/z : 250 [M+1]. |
| 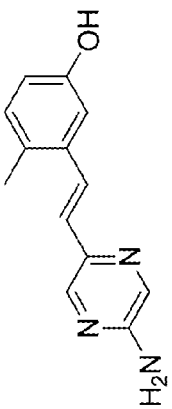<br>IV-4 | (E)-3-(2-(5-aminopyrazin-2-yl)vinyl)-4-methylphenol | MS m/z : 228 [M+1]. |

FIG. 4B

| Structure | Name | MS |
|---|---|---|
| IV-5 | (E)-5-(2-(4-chloro-1-(pyridin-4-ylmethyl)-1H-pyrrolo[2,3-b]pyridin-5-yl)vinyl)pyrazin-2-amine | MS m/z : 363 [M+1]. |
| IV-6 | (E)-N-(3-(2-(5-aminopyrazin-2-yl)vinyl)-4-methylphenyl)-3-(4-methyl-1H-imidazol-1-yl)-5-(trifluoromethyl)benzamide | MS m/z : 479 [M+1]. |
| IV-7 | (E)-N-(3-(2-(5-aminopyrazin-2-yl)vinyl)-4-methylphenyl)-2-fluoro-5-(trifluoromethyl)benzamide | MS m/z : 417 [M+1]. |

| | (E)-N-(6-(2-(5-aminopyrazin-2-yl)vinyl)benzo[d]thiazol-2-yl)-4-((4-ethylpiperazin-1-yl)methyl)-3-(trifluoromethyl)benzamide | MS m/z : 568 [M+1]. |

IV-8

FIG. 5A: Table 5. The following compounds were produced by using the corresponding starting compounds according to method similar to that described in Example 5.
| Structure | Name | $^1$H NMR, and/or MS(m/z) |
|---|---|---|
| 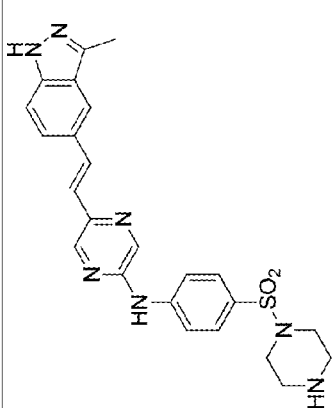<br>V-2 | (E)-5-(2-(3-methyl-1H-indazol-5-yl)vinyl)-N-(4-(piperazin-1-ylsulfonyl)phenyl)pyrazin-2-amine | MS m/z : 476 [M+1]. |
| 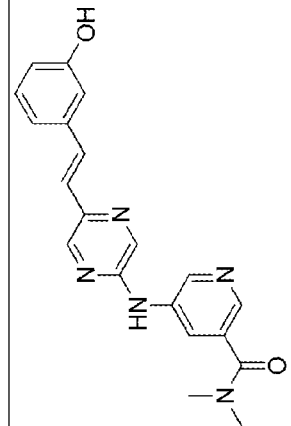<br>V-3 | (E)-5-(5-(3-hydroxystyryl)pyrazin-2-ylamino)-N,N-dimethylnicotinamide | MS m/z : 362 [M+1]. |

FIG. 5B
| | | |
|---|---|---|
| 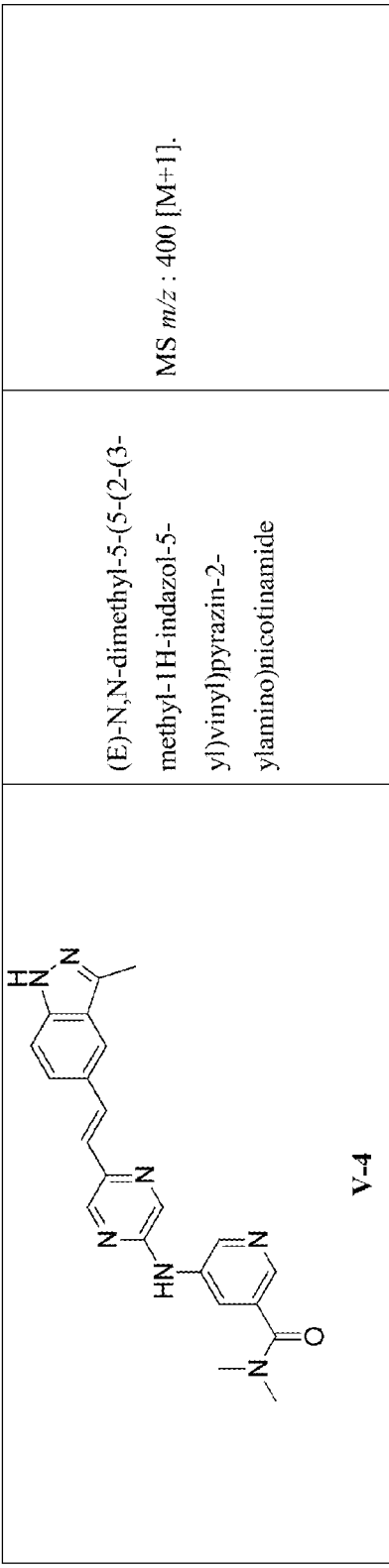<br>V-4 | (E)-N,N-dimethyl-5-(5-(2-(3-methyl-1H-indazol-5-yl)vinyl)pyrazin-2-ylamino)nicotinamide | MS m/z : 400 [M+1]. |
| 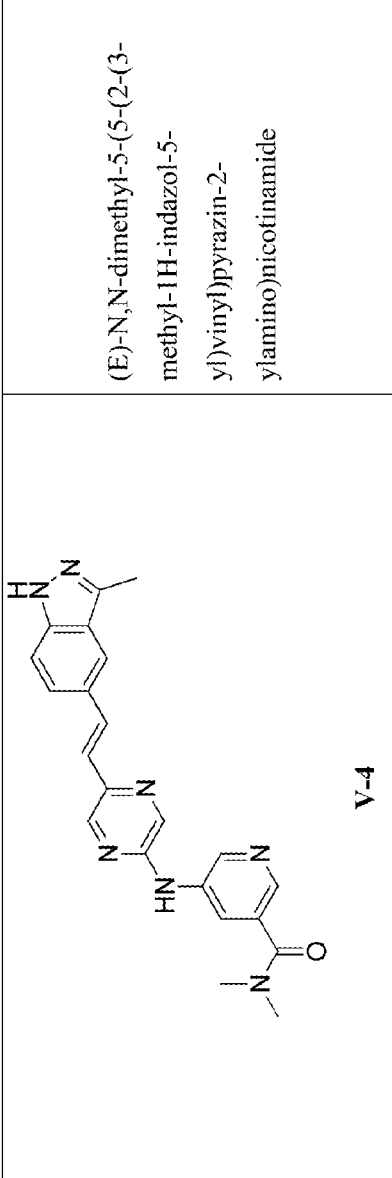<br>V-5 | (E)-3-(2-(5-(2-methyl-6-(piperazin-1-yl)pyrimidin-4-ylamino)pyrazin-2-yl)vinyl)phenol | MS m/z : 390 [M+1]. |

FIG. 5C

| Structure | Name | MS |
|---|---|---|
| V-6 | (E)-2-methyl-N-(5-(2-(3-methyl-1H-indazol-5-yl)vinyl)pyrazin-2-yl)-6-(piperazin-1-yl)pyrimidin-4-amine | MS m/z : 428 [M+1]. |
| V-7 | (E)-6-(2-(5-(2-methyl-6-(piperazin-1-yl)pyrimidin-4-ylamino)pyrazin-2-yl)vinyl)benzo[d]thiazol-2-amine | MS m/z : 446 [M+1]. |
| V-8 | (E)-N-(5-(2-(5-aminopyrazin-2-yl)vinyl)pyrazin-2-yl)-2-methyl-6-(piperazin-1-yl)pyrimidin-4-amine | MS m/z : 391 [M+1]. |

FIG. 5D

| Structure | Name | MS |
|---|---|---|
| V-9 | (E)-4-methyl-3-(2-(5-(2-methyl-6-(piperazin-1-yl)pyrimidin-4-ylamino)pyrazin-2-yl)vinyl)benzoic acid | MS m/z : 432 [M+1]. |
| V-10 | (E)-4-methyl-3-(2-(5-(2-methyl-6-(piperazin-1-yl)pyrimidin-4-ylamino)pyrazin-2-yl)vinyl)-N-(3-(trifluoromethyl)phenyl)benzamide | MS m/z : 575 [M+1]. |
| V-11 | (E)-N-(4-((4-ethylpiperazin-1-yl)methyl)-3-(trifluoromethyl)phenyl)-4-methyl-3-(2-(5-(2-methyl-6-(piperazin-1-yl)pyrimidin-4-ylamino)pyrazin-2-yl)vinyl)benzamide | MS m/z : 701 [M+1]. |

FIG. 5F

| | | |
|---|---|---|
| V-14 | (E)-4-(2-(5-(2-methyl-6-(piperazin-1-yl)pyrimidin-4-ylamino)pyrazin-2-yl)vinyl)indolin-2-one | MS m/z : 429 [M+1]. |
| V-15 | (E)-3-(2-(5-(2-methyl-6-(piperazin-1-yl)pyrimidin-4-ylamino)pyrazin-2-yl)vinyl)-N-(3-(trifluoromethyl)phenyl)benzamide | MS m/z : 561 [M+1]. |
| V-16 | (E)-N-cyclopropyl-3-(2-(5-(2-methyl-6-(piperazin-1-yl)pyrimidin-4-ylamino)pyrazin-2-yl)vinyl)benzamide | MS m/z : 457 [M+1]. |

FIG. 5G
| | | |
|---|---|---|
| 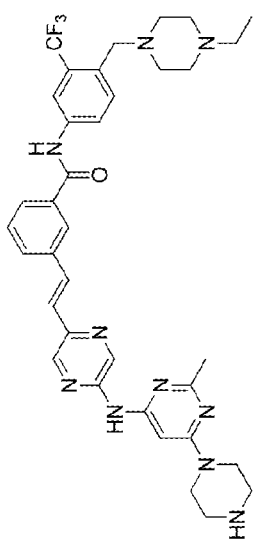 V-17 | (E)-N-(4-((4-ethylpiperazin-1-yl)methyl)-3-(trifluoromethyl)phenyl)-3-(2-(5-(2-methyl-6-(piperazin-1-yl)pyrimidin-4-ylamino)pyrazin-2-yl)vinyl)benzamide | MS *m/z* : 687 [M+1]. |
| 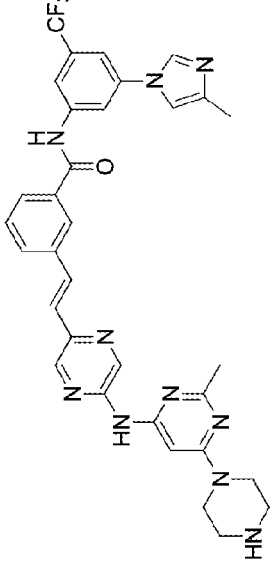 V-18 | (E)-N-(3-(4-methyl-1H-imidazol-1-yl)-5-(trifluoromethyl)phenyl)-3-(2-(5-(2-methyl-6-(piperazin-1-yl)pyrimidin-4-ylamino)pyrazin-2-yl)vinyl)benzamide | MS *m/z* : 641 [M+1]. |

FIG. 6A Table 6. The following compounds were produced by using the corresponding starting compounds according to method similar to that described in Example 6.

| Structure | Name | $^1$H NMR, and/or MS(m/z) |
|---|---|---|
| VI-1 | 4-chloro-N-(5-(4-((4-ethylpiperazin-1-yl)methyl)-3-(trifluoromethyl)benzamido)-2-methylphenyl)-1H-pyrrolo[2,3-b]pyridine-5-carboxamide | $^1$H NMR (600 MHz, DMSO-$d_6$) δ 11.89 (s, 1H), 10.21 (s, 1H), 9.33 (brs, 1H), 8.13 (s, 1H), 8.10 (s, 1H), 7.96 (d, $J$ = 7.8 Hz, 1H), 7.60 (d, $J$ = 8.4 Hz, 1H), 7.50 (t, $J$ = 3.0 Hz, 1H), 7.12 (d, $J$ = 7.2 Hz, 1H), 7.10 (d, $J$ = 7.8 Hz, 1H), 6.98 (s, 1H), 6.43 (s, 1H), 4.55 (s, 2H), 3.65-3.55 (m, 2H), 3.10-3.02 (m, 2H), 2.95-2.80 (m, 4H), 2.35-2.30 (m, 2H), 2.17 (s, 3H), 1.14 (t, $J$ = 7.2 Hz, 3H). MS m/z : 599 [M+1]. |

FIG. 6B
| | | |
|---|---|---|
| 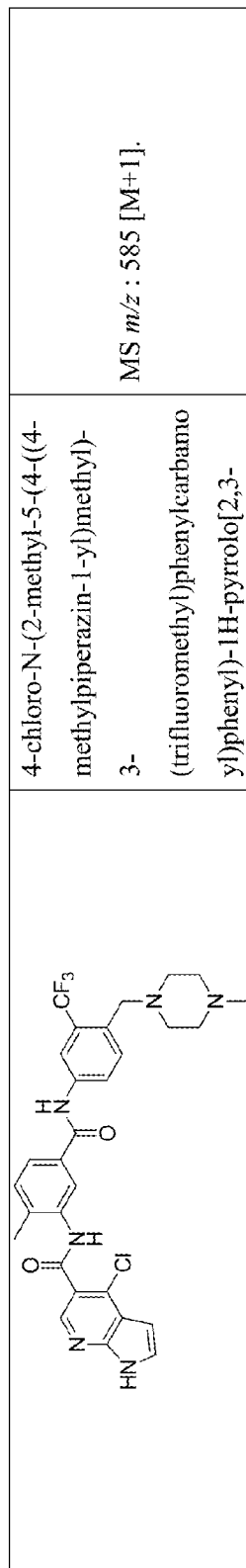 VI-2 | 4-chloro-N-(2-methyl-5-(4-((4-methylpiperazin-1-yl)methyl)-3-(trifluoromethyl)phenylcarbamoyl)phenyl)-1H-pyrrolo[2,3-b]pyridine-5-carboxamide | MS *m/z* : 585 [M+1]. |
| 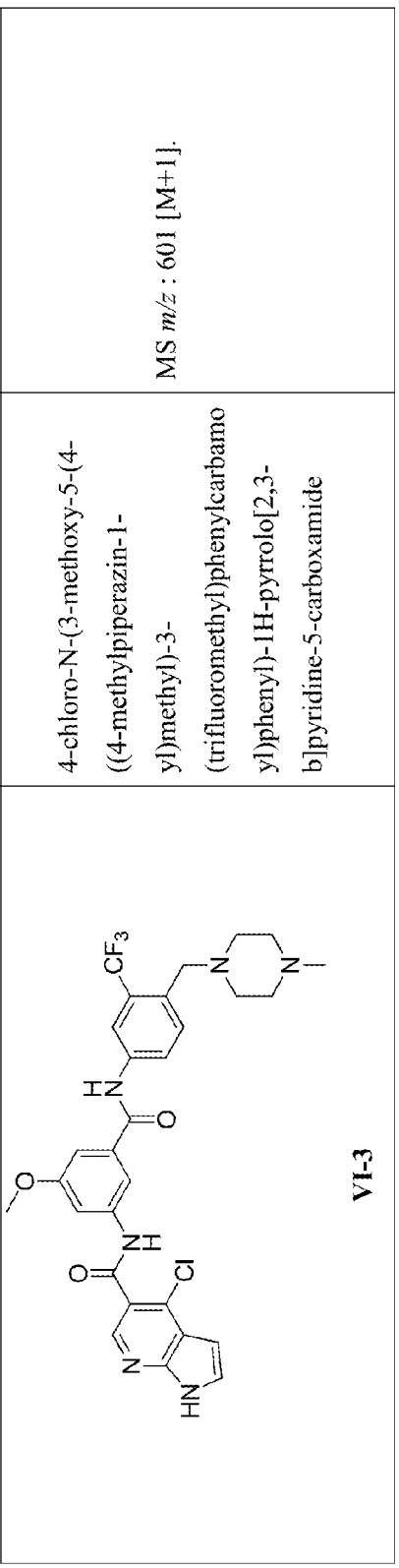 VI-3 | 4-chloro-N-(3-methoxy-5-(4-((4-methylpiperazin-1-yl)methyl)-3-(trifluoromethyl)phenylcarbamoyl)phenyl)-1H-pyrrolo[2,3-b]pyridine-5-carboxamide | MS *m/z* : 601 [M+1]. |

FIG. 7A: Table 7. The following compounds were produced by using the corresponding starting compounds according to method similar to that described in Example 7.

| Structure | Name | ¹H NMR, and/or MS(m/z) |
|---|---|---|
| VII-2 | N-(3-((4-chloro-1H-pyrrolo[2,3-b]pyridin-5-yl)methylamino)-4-methylphenyl)-4-((4-ethylpiperazin-1-yl)methyl)-3-(trifluoromethyl)benzamide | MS m/z : 585 [M+1]. |
| VII-3 | 3-((4-chloro-1H-pyrrolo[2,3-b]pyridin-5-yl)methylamino)-5-methoxy-N-(3-(trifluoromethyl)phenyl)benzamide | ¹H NMR (600 MHz, DMSO-$d_6$) δ 11.95 (s, 1H), 10.33 (s, 1H), 8.25 (s, 1H), 8.19 (s, 1H), 8.00 (d, $J$ = 7.2 Hz, 1H), 7.55 (s, 2H), 7.40 (d, $J$ = 7.2 Hz, 1H), 6.81 (s, 1H), 6.71 (s, 1H), 6.48-6.42 (m, 2H), 6.38 (s, 1H), 4.48 (s, 2H), 3.72 (s, 3H). MS m/z : 475 [M+1]. |

FIG. 7C
| | | |
|---|---|---|
| 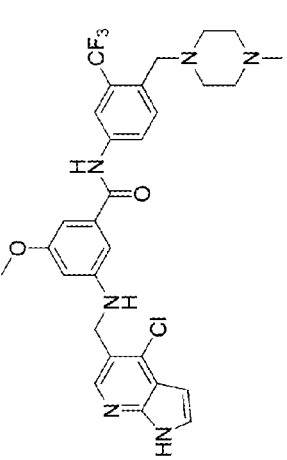<br>VII-6 | 3-((4-chloro-1H-pyrrolo[2,3-b]pyridin-5-yl)methylamino)-5-methoxy-N-(4-((4-methylpiperazin-1-yl)methyl)-3-(trifluoromethyl)phenyl)benzamide | ¹H NMR (600 MHz, CDCl₃) δ 10.31 (s, 1H), 8.28 (s, 1H), 7.94 (s, 1H), 7.84-7.82 (m, 2H), 7.73 (d, J = 8.4 Hz, 1H), 7.35 (s, 1H), 6.77 (s, 1H), 6.70 (s, 1H), 6.59 (s, 1H), 6.35 (s, 1H), 4.54 (s, 2H), 4.34 (s, 1H), 3.78 (s, 3H), 3.61 (s, 2H), 2.70-2.35 (m, 8H), 2.29 (s, 3H). MS m/z : 587 [M+1]. |
| 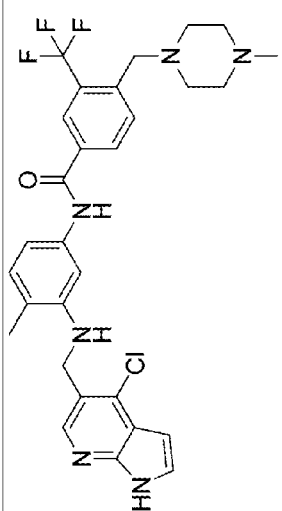<br>VII-7 | N-(3-((4-chloro-1H-pyrrolo[2,3-b]pyridin-5-yl)methylamino)-4-methylphenyl)-4-((4-methylpiperazin-1-yl)methyl)-3-(trifluoromethyl)benzamide | MS m/z : 571 [M+1]. |

FIG. 7D

| Structure | Name | MS |
|---|---|---|
| 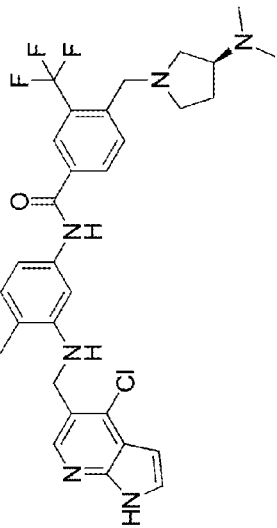 VII-8 | (S)-N-(3-((4-chloro-1H-pyrrolo[2,3-b]pyridin-5-yl)methylamino)-4-methylphenyl)-4-((3-(dimethylamino)pyrrolidin-1-yl)methyl)-3-(trifluoromethyl)benzamide | MS m/z : 585 [M+1]. |
| 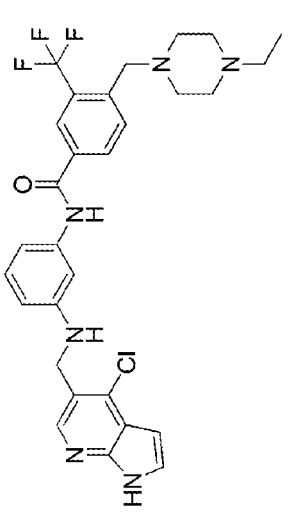 VII-9 | N-(3-((4-chloro-1H-pyrrolo[2,3-b]pyridin-5-yl)methylamino)phenyl)-4-((4-ethylpiperazin-1-yl)methyl)-3-(trifluoromethyl)benzamide | MS m/z : 571 [M+1]. |
| 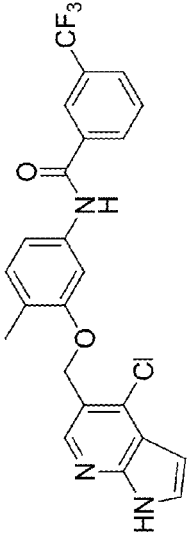 VII-10 | N-(3-((4-chloro-1H-pyrrolo[2,3-b]pyridin-5-yl)methoxy)-4-methylphenyl)-3-(trifluoromethyl)benzamide | MS m/z : 460 [M+1]. |

FIG. 8: Table 8. The following compound was produced by using the corresponding starting compounds according to method similar to that described in Example 8.
| Structure | Name | ¹H NMR, and/or MS(*m/z*) |
|---|---|---|
| 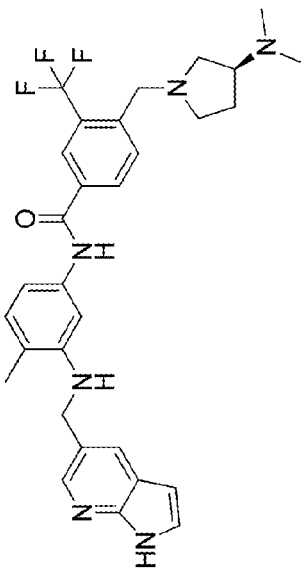<br>VIII-2 | (S)-N-(3-((1H-pyrrolo[2,3-b]pyridin-5-yl)methylamino)-4-methylphenyl)-4-((3-(dimethylamino)pyrrolidin-1-yl)methyl)-3-(trifluoromethyl)benzamide | MS *m/z* : 551 [M+1]. |

FIG. 9A: Table 9. The following compounds were produced by using the corresponding starting compounds according to method similar to that described in Example 9.

| Structure | Name | ¹H NMR, and/or MS(m/z) |
|---|---|---|
| IX-2 | 3-((4-methoxy-1H-pyrrolo[2,3-b]pyridin-5-yl)methylamino)-4-methyl-N-(4-((4-methylpiperazin-1-yl)methyl)-3-(trifluoromethyl)phenyl)benzamide | MS m/z : 567 [M+1]. |
| IX-3 | 3-methoxy-5-((4-methoxy-1H-pyrrolo[2,3-b]pyridin-5-yl)methylamino)-N-(4-((4-methylpiperazin-1-yl)methyl)-3-(trifluoromethyl)phenyl)benzamide | MS m/z : 583 [M+1]. |

FIG. 9B

| Structure | Name | MS |
|---|---|---|
| IX-3 | 4-((4-ethylpiperazin-1-yl)methyl)-N-(3-((4-methoxy-1H-pyrrolo[2,3-b]pyridin-5-yl)methylamino)phenyl)-3-(trifluoromethyl)benzamide | MS m/z : 567 [M+1]. |
| IX-4 | N-(3-((4-methoxy-1H-pyrrolo[2,3-b]pyridin-5-yl)methylamino)phenyl)-3-(trifluoromethyl)benzamide | MS m/z : 441 [M+1]. |
| IX-5 | N-(4-((4-ethylpiperazin-1-yl)methyl)-3-(trifluoromethyl)phenyl)-3-((4-methoxy-1H-pyrrolo[2,3-b]pyridin-5-yl)methylamino)benzamide | MS m/z : 567 [M+1]. |

FIG. 9C
| | | |
|---|---|---|
| 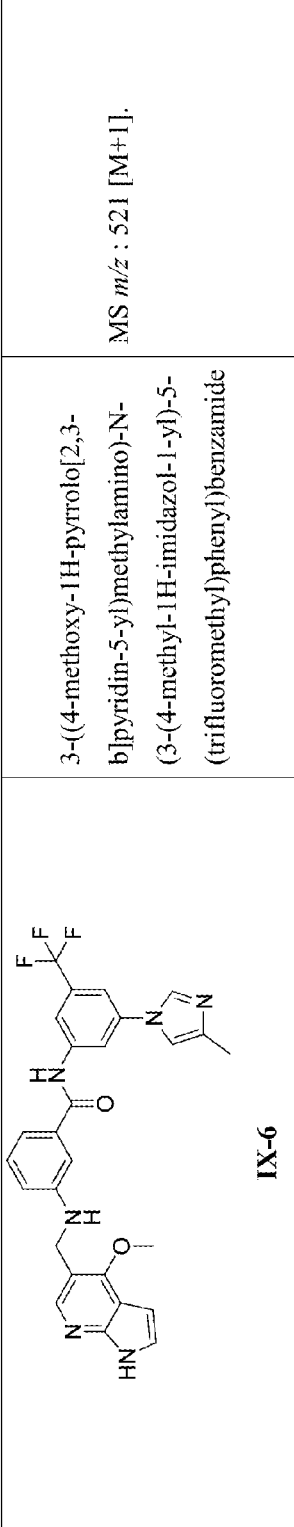 IX-6 | 3-((4-methoxy-1H-pyrrolo[2,3-b]pyridin-5-yl)methylamino)-N-(3-(4-methyl-1H-imidazol-1-yl)-5-(trifluoromethyl)phenyl)benzamide | MS m/z : 521 [M+1]. |
| 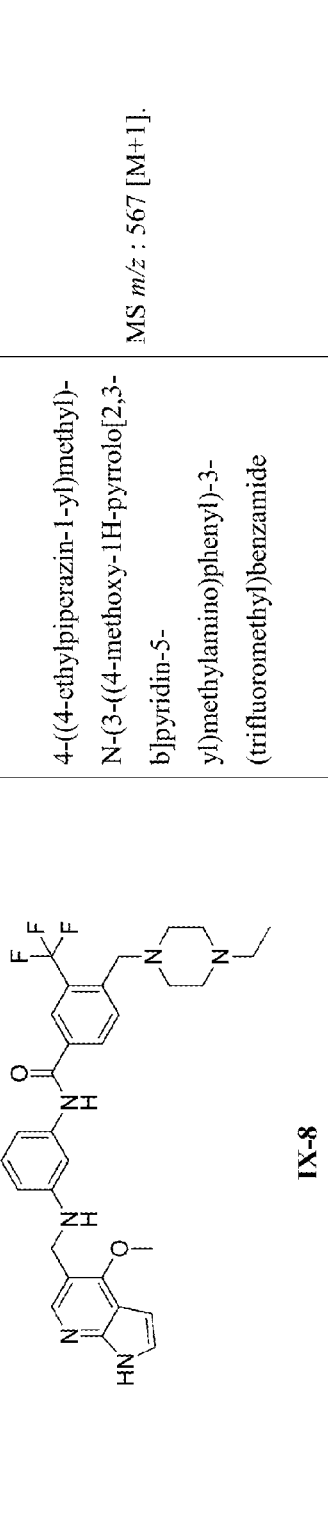 IX-7 | 3-((4-methoxy-1H-pyrrolo[2,3-b]pyridin-5-yl)methylamino)-N-(3-(trifluoromethyl)phenyl)benzamide | MS m/z : 441 [M+1]. |
|  IX-8 | 4-((4-ethylpiperazin-1-yl)methyl)-N-(3-((4-methoxy-1H-pyrrolo[2,3-b]pyridin-5-yl)methylamino)phenyl)-3-(trifluoromethyl)benzamide | MS m/z : 567 [M+1]. |

FIG. 10A: Table 10. The following compounds were produced by using the corresponding starting compounds according to method similar to that described in Example 10.

| Structure | Name | ¹H NMR, and/or MS(*m/z*) |
|---|---|---|
| X-2 | 3-((4-(isopropylthio)-1H-pyrrolo[2,3-b]pyridin-5-yl)methylamino)-N-(3-(trifluoromethyl)phenyl)benzamide | MS *m/z* : 485 [M+1]. |
| X-3 | N-(4-((4-ethylpiperazin-1-yl)methyl)-3-(trifluoromethyl)phenyl)-3-((4-(isopropylthio)-1H-pyrrolo[2,3-b]pyridin-5-yl)methylamino)benzamide | MS *m/z* : 611 [M+1]. |
| X-4 | 3-((4-(isopropylthio)-1H-pyrrolo[2,3-b]pyridin-5-yl)methylamino)-N-(3-(4-methyl-1H-imidazol-1-yl)-5-(trifluoromethyl)phenyl)benzamide | MS *m/z* : 565 [M+1]. |

FIG. 10B
| | | |
|---|---|---|
| 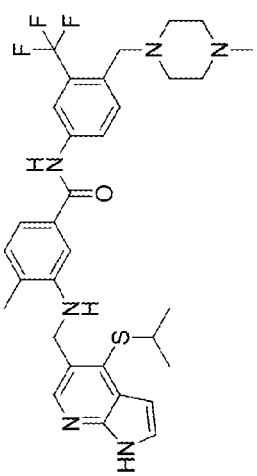 X-5 | 3-((4-(isopropylthio)-1H-pyrrolo[2,3-b]pyridin-5-yl)methylamino)-4-methyl-N-(4-(((4-methylpiperazin-1-yl)methyl)-3-(trifluoromethyl)phenyl)benzamide | MS m/z : 611 [M+1]. |
| 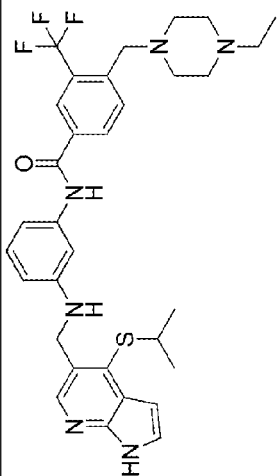 X-6 | 4-((4-ethylpiperazin-1-yl)methyl)-N-(3-((4-(isopropylthio)-1H-pyrrolo[2,3-b]pyridin-5-yl)methylamino)phenyl)-3-(trifluoromethyl)benzamide | MS m/z : 611 [M+1]. |

FIG. 11A: Table 11. The following compounds were produced by using the corresponding starting compounds according to method similar to that described in Example 11.

| Structure | Name | ¹H NMR, and/or MS(m/z) |
|---|---|---|
| XI-1 | (E)-N-(4-((4-ethylpiperazin-1-yl)methyl)-3-(trifluoromethyl)phenyl)-3-(2-(4-methoxy-1H-pyrrolo[2,3-b]pyridin-5-yl)vinyl)-4-methylbenzamide | ¹H NMR (600 MHz, CD₃OD) δ 8.31 (s, 1H), 8.17 (d, J = 1.8 Hz, 1H), 8.10 (d, J = 2.4 Hz, 1H), 7.91 (dd, J = 1.8, 8.4 Hz, 1H), 7.71-7.67 (m, 2H), 7.41 (d, J = 16.8 Hz, 1H), 7.32 (d, J = 16.2 Hz, 1H), 7.25 (d, J = 7.8 Hz, 1H), 7.23 (d, J = 3.6 Hz, 1H), 6.78 (d, J = 3.6 Hz, 1H), 4.35 (s, 3H), 3.61 (s, 2H), 2.60-2.40 (m, 13H), 1.08 (t, J = 7.2 Hz, 3H). MS m/z : 578 [M+1]. |
| XI-2 | (E)-3-(2-(4-methoxy-1H-pyrrolo[2,3-b]pyridin-5-yl)vinyl)-4-methyl-N-(3-(4-methyl-1H-imidazol-1-yl)-5-(trifluoromethyl)phenyl)benzamide | MS m/z : 532 [M+1]. |

FIG. 11B

| | | |
|---|---|---|
| XI-3 | (E)-N-(2-fluoro-5-(trifluoromethyl)phenyl)-3-(2-(4-methoxy-1H-pyrrolo[2,3-b]pyridin-5-yl)vinyl)-4-methylbenzamide | MS m/z : 470 [M+1]. |
| XI-4 | (E)-3-(2-(4-chloro-1H-pyrrolo[2,3-b]pyridin-5-yl)vinyl)-4-methyl-N-(3-(4-methyl-1H-imidazol-1-yl)-5-(trifluoromethyl)phenyl)benzamide | MS m/z : 536 [M+1]. |
| XI-5 | (E)-3-(2-(4-chloro-1H-pyrrolo[2,3-b]pyridin-5-yl)vinyl)-4-methyl-N-(3-(trifluoromethyl)phenyl)benzamide | MS m/z : 456 [M+1]. |
| XI-6 | (E)-3-(2-(4-chloro-1H-pyrrolo[2,3-b]pyridin-5-yl)vinyl)-N-(2-fluoro-5-(trifluoromethyl)phenyl)-4-methylbenzamide | MS m/z : 474 [M+1]. |

FIG. 12A: Table 12. The following compounds were produced by using the corresponding starting compounds according to method similar to that described in Example 12.

| Structure | Name | $^1$H NMR, and/or MS(m/z) |
|---|---|---|
| 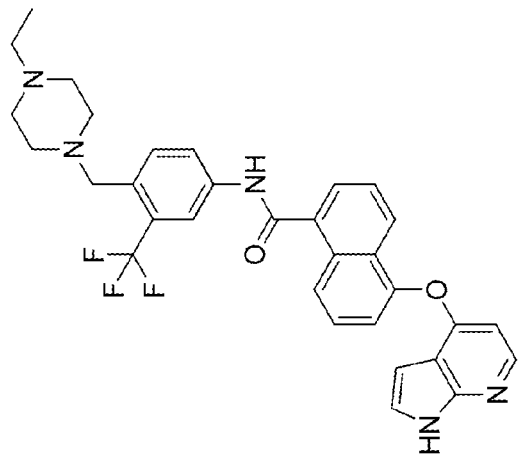<br>XII-2 | 5-(1H-pyrrolo[2,3-b]pyridin-4-yloxy)-N-(4-((4-ethylpiperazin-1-yl)methyl)-3-(trifluoromethyl)phenyl)-1-naphthamide | $^1$H NMR (600 MHz, CDCl$_3$) δ 10.42 (s, 1H), 8.36 (d, J = 9.0 Hz, 1H), 8.25 (s, 1H), 8.08 (brs, 1H), 7.90 (d, J = 7.8 Hz, 1H), 7.87 (s, 1H), 7.79 (d, J = 8.4 Hz, 1H), 7.62 (d, J = 6.6 Hz, 1H), 7.59 (d, J = 8.4 Hz, 1H), 7.50 (d, J = 8.4 Hz, 1H), 7.42 (dd, J = 7.2, 1.2 Hz, 1H), 7.34 (dd, J = 2.4, 9.6 Hz, 1H), 7.14 (d, J = 3.6 Hz, 1H), 6.48 (d, J = 4.2 Hz, 1H), 6.30 (d, J = 3.6 Hz, 1H), 3.61 (s, 2H), 3.00-2.50 (m, 10H), 1.14 (t, J = 7.8 Hz, 3H). MS m/z : 574 [M+1]. |

FIG. 12B
| 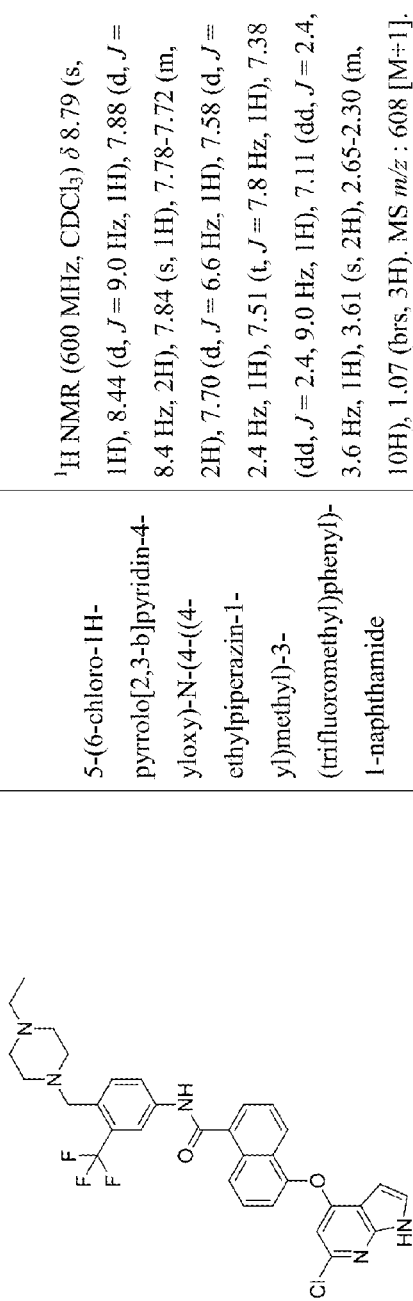 | 5-(6-chloro-1H-pyrrolo[2,3-b]pyridin-4-yloxy)-N-(4-((4-ethylpiperazin-1-yl)methyl)-3-(trifluoromethyl)phenyl)-1-naphthamide | $^1$H NMR (600 MHz, CDCl$_3$) δ 8.79 (s, 1H), 8.44 (d, $J$ = 9.0 Hz, 1H), 7.88 (d, $J$ = 8.4 Hz, 2H), 7.84 (s, 1H), 7.78-7.72 (m, 2H), 7.70 (d, $J$ = 6.6 Hz, 1H), 7.58 (d, $J$ = 2.4 Hz, 1H), 7.51 (t, $J$ = 7.8 Hz, 1H), 7.38 (dd, $J$ = 2.4, 9.0 Hz, 1H), 7.11 (dd, $J$ = 2.4, 3.6 Hz, 1H), 3.61 (s, 2H), 2.65-2.30 (m, 10H), 1.07 (brs, 3H). MS $m/z$ : 608 [M+1]. |
|---|---|---|
| XII-3 | | |
| 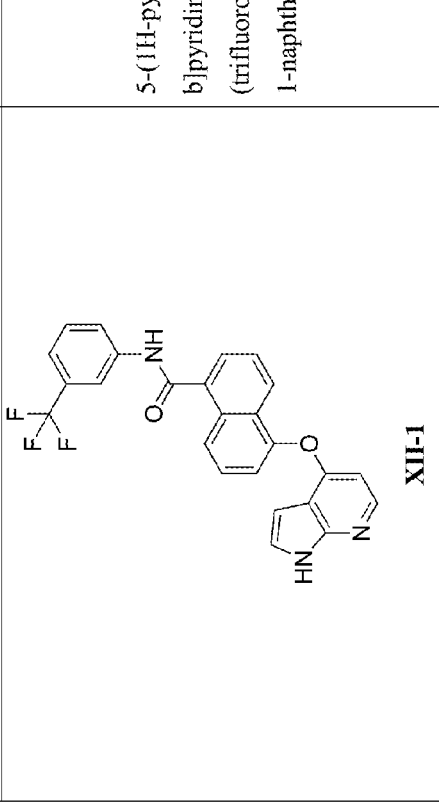 | 5-(1H-pyrrolo[2,3-b]pyridin-4-yloxy)-N-(3-(trifluoromethyl)phenyl)-1-naphthamide | MS $m/z$ : 448 [M+1]. |
| XII-1 | | |

| Structure | Name | Data |
|---|---|---|
| XII-4 | 5-(6-chloro-1H-pyrrolo[2,3-b]pyridin-4-yloxy)-N-(3-(trifluoromethyl)phenyl)-1-naphthamide | $^{1}$H NMR (600 MHz, DMSO-$d_6$) δ 12.03 (s, 1H), 10.95 (s, 1H), 8.34 (s, 2H), 8.12 (d, $J$ = 7.8 Hz, 1H), 8.06-8.00 (m, 1H), 7.89 (s, 1H), 7.84-7.80 (m, 1H), 7.70-7.60 (m, 2H), 7.55 (d, $J$ = 7.8 Hz, 1H), 7.50 (d, $J$ = 6.6 Hz, 1H), 7.41 (s, 1H), 6.53 (s, 1H), 6.20 (s, 1H). MS $m/z$: 482 [M+1]. |
| XII-5 | 3-(1H-pyrrolo[2,3-b]pyridin-4-yloxy)-4-methyl-N-(3-(trifluoromethyl)phenyl)benzamide | MS $m/z$: 412 [M+1]. |

FIG. 12D

| Structure | Name | Data |
|---|---|---|
| XII-6 | 3-(6-chloro-1H-pyrrolo[2,3-b]pyridin-4-yloxy)-N-(4-((4-ethylpiperazin-1-yl)methyl)-3-(trifluoromethyl)phenyl)-4-methylbenzamide | MS m/z : 572 [M+1]. |
| XII-7 | 3-(6-chloro-1H-pyrrolo[2,3-b]pyridin-4-yloxy)-N-(4-((4-ethylpiperazin-1-yl)methyl)-3-(trifluoromethyl)phenyl)-4-methylbenzamide | $^1$H NMR (600 MHz, DMSO-$d_6$) δ 11.90 (s, 1H), 10.45 (s, 1H), 8.14 (d, $J$ = 2.4 Hz, 1H), 8.10 (d, $J$ = 5.4 Hz, 1H), 8.04 (d, $J$ = 9.0 Hz, 1H), 7.88 (d, $J$ = 7.8 Hz, 1H), 7.76 (s, 1H), 7.67 (d, $J$ = 8.4 Hz, 1H), 7.56 (d, $J$ = 7.8 Hz, 1H), 7.38 (t, $J$ = 3.0 Hz, 1H), 3.64 (s, 2H), 3.42 (d, $J$ = 11.4 Hz, 2H), 3.11-3.08 (m, 2H), 3.00-2.90 (m, 2H), 2.89 (d, $J$ = 11.4 Hz, 2H), 2.35 (t, $J$ = 11.4 Hz, 2H), 2.21 (s, 3H), 1.17 (t, $J$ = 7.2 Hz, 3H). MS m/z : 538 [M+1]. |

FIG. 13: Table 13. The following compounds were produced by using the corresponding starting compounds according to method similar to that described in Example 13.

| Structure | Name | ¹H NMR, and/or MS(*m/z*) |
|---|---|---|
| XIII-2 | 4-methyl-3-(6-(4-(4-methylpiperazin-1-yl)phenylamino)-1H-pyrrolo[2,3-b]pyridin-4-yloxy)-N-(3-(trifluoromethyl)phenyl)benzamide | MS *m/z* : 601 [M+1]. |

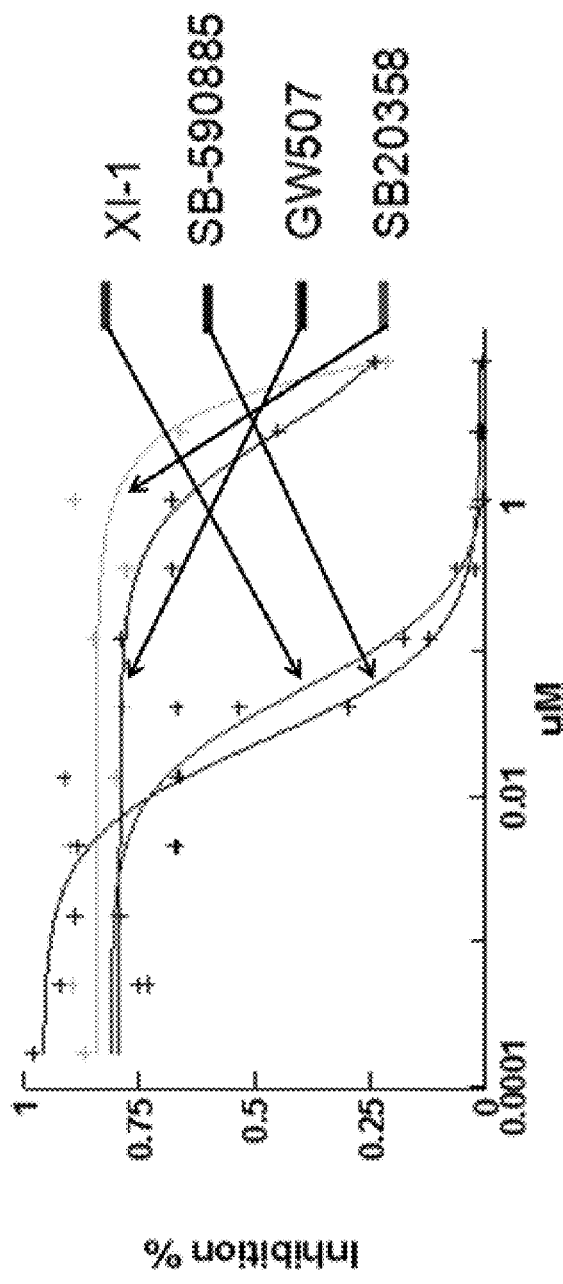
FIG. 14A: Dose response IC50 calculation for XI-1 ((E)-N-(4-((4-ethylpiperazin-1-yl)methyl)-3-(2-(4-methoxy-1H-pyrrolo[2,3-b]pyridin-5-yl)vinyl)-4-methylbenzamide) compared to reference Raf inhibitors SB-590885, GW5074, SB203580
FIG. 14B: Compounds IC50 on B-RAF *V600E* transformed Ba/F3 cells (μM)
| XI-1 | SB-590885 | GW5074 | SB203580 |
|------|-----------|--------|----------|
| 0.09 | 0.04 | 2.8 | 3.91 |

FIG. 15A: Summary of antiproliferative activity of XI-1 against a variety of cancer cell lines. XI-1 possesses most superior activity against V600E b-raf transformed lines

| Cells | Genetic status | Cellular IC50 (µM) | | | | | | |
|---|---|---|---|---|---|---|---|---|
| | | XI-1 | BAY61-3606 | Sorafenib | SB590885 | PLX4720 | Torin-1 | Dasatinib |
| A373-C6 | B-RAF V600E | 0.63 | >10 | 3.50 | 3.60 | 4.80 | ND | ND |
| A375 | B-RAF V600E | 0.18 | 0.40 | 0.99 | 0.03 | 0.10 | 0.02 | 5.17 |
| BRAF/Baf3 | B-RAF T529I & V600E | 0.42 | | 6.50 | 2.90 | >10 | ND | ND |
| BRAF/Baf3 | B-RAF V600E | 0.09 | 0.25 | 0.81 | 0.04 | 0.16 | 0.01 | 5.16 |
| CH-212 | | 1.06 | 0.53 | 4.31 | >10 | >10 | ND | ND |
| M14 | B-RAF V600E | 0.80 | >10 | 4.34 | 1.11 | 2.56 | ND | ND |
| NAE | B-RAF V600E | 0.35 | 1.87 | 1.27 | 1.05 | 0.28 | 0.02 | >10 |
| SK-MEL-5 | B-RAF V600E | 1.64 | 0.65 | 3.39 | 2.10 | 0.06 | 0.04 | >10 |
| TRPM | B-RAF V600E | 0.65 | 0.15 | 1.00 | >10 | >10 | 0.05 | >10 |
| SK-MEL28 | B-RAF V600E | 0.30 | 0.12 | 0.90 | 0.10 | 0.62 | 5.08 | >10 |
| SK-MEL30 | N-RAS Q61R | 1.70 | 8.22 | 5.50 | 3.20 | >10 | ND | ND |

FIG. 15B

| HCT116 |  | 1.10 | ND | ND | ND | ND | ND | ND |
|---|---|---|---|---|---|---|---|---|
| HKE3 |  | 3.20 | ND | ND | ND | ND | ND | ND |
| HT29 |  | 0.20 | ND | ND | ND | ND | ND | ND |
| K029 | *B-RAF V600E* | 0.19 | ND | ND | ND | 0.59 | ND | ND |
| M34 | *B-RAF V600E* | 1.64 | ND | ND | ND | >3 | ND | ND |
| M23 | *N-RAS Q61R* | 0.85 | ND | ND | ND | >3 | ND | ND |
| K033 | *N-RAS Q61R* | 1.66 | ND | ND | ND | >3 | ND | ND |

FIG. 16A: Kinase targets of XI-1 and related analogs

| | Gray044 |
|---|---|
| ABL1 | 0 |
| ABL2 | 0 |
| BRAF(V600E) | 0 |
| CSF1R | 0 |
| EGFR | 0 |
| EPHA8 | 0 |
| FGFR4 | 0 |
| FLT3 | 0 |
| KIT | 0 |
| LOK | 0 |
| MAP4K1 | 0 |
| MUSK | 0 |
| p38-beta | 0 |
| PDGFRA | 0 |
| PDGFRB | 0 |
| RET | 0 |
| TAOK3 | 0 |
| TNNI3K | 0 |

FIG. 16B: Kinase targets of XI-1 and related analogs

| | | | |
|---|---|---|---|
| FES | 0.05 | MAP4K4 | 0.25 |
| LYN | 0.05 | MKNK2 | 0.25 |
| p38-alpha | 0.05 | TEC | 0.25 |
| SRPK1 | 0.05 | FLT1 | 0.3 |
| STK36 | 0.05 | HCK | 0.3 |
| TIE2 | 0.05 | TNK2 | 0.3 |
| DDR1 | 0.1 | TXK | 0.3 |
| EPHA2 | 0.1 | BTK | 0.35 |
| RIOK1 | 0.1 | SLK | 0.35 |
| RIOK3 | 0.1 | RIPK1 | 0.4 |
| SNF1LK | 0.1 | RIPK2 | 0.4 |
| SRC | 0.1 | BIKE | 0.45 |
| TAK1 | 0.1 | CIT | 0.45 |
| BLK | 0.15 | CDKL2 | 0.5 |
| EPHA4 | 0.15 | DRAK1 | 0.5 |
| EPHB2 | 0.15 | EPHB1 | 0.5 |
| FGR | 0.15 | JNK2 | 0.5 |
| FLT4 | 0.15 | BRAF | 0.55 |
| MAP4K2 | 0.15 | MLK1 | 0.55 |
| ANKK1 | 0.2 | MYLK2 | 0.55 |
| FRK | 0.2 | TRKB | 0.55 |
| LCK | 0.2 | VEGFR2 | 0.55 |
| MAP4K5 | 0.2 | YES | 0.55 |
| EGFR | 0.25 | IKK-alpha | 0.6 |
| ERBB4 | 0.25 | PTK2B | 0.6 |
| | | MAP4K3 | 0.65 |
| | | TIE1 | 0.7 |
| | | FYN | 0.75 |
| | | FGFR1 | 0.8 |
| | | ZAK | 0.8 |
| | | DDR2 | 0.9 |
| | | RAF1 | 0.95 |
| | | AURKC | 1 |

FIG. 17A: Additional targets of XI-1 determined using a chemical proteomics approach

| Kinase Name | HL60_ATPProbe |
|---|---|
| LYN | 96.8 |
| CSK | 96.0 |
| ABL1/2 | 92.8 |
| TAO1/3 | 90.3 |
| HPK1 | 85.0 |
| FGR | 83.2 |
| p38a (MAPKAPK2/3 In | 79.8 |
| FES | 79.1 |
| FER | 76.8 |
| TAO2 | 70.7 |
| KHS1/2 | 67.3 |
| AurA/B/C | 63.8 |
| MAP3K2 | 62.9 |
| PYK2 | 62.7 |
| MPSK1 | 51.9 |
| p38a | 51.0 |
| NEK9 | 34.7 |
| PKD1/2 | 34.0 |
| LOK | 33.5 |
| IRAK4 | 33.3 |
| MST2 | 31.7 |
| NEK9 | 28.2 |
| PLK1 | 26.8 |
| MST1 | 20.4 |
| CK2a1 | 17.8 |
| GSK3A | 17.5 |
| CDK7 | 17.2 |
| AMPKa1/2 | 17.1 |

FIG. 17B

| | |
|---|---|
| IRE1 | 16.9 |
| AurA | 15.5 |
| MARK3 | 15.0 |
| p38d/g | 12.9 |
| HSER | 12.3 |
| PIP5K2a | 12.2 |
| STLK5 | 11.9 |
| MAP2K4 | 9.3 |
| PITSLRE | 8.6 |
| CDK2 | 7.8 |
| RSK1/2/3 (Domain 1) | 7.7 |
| PHKg2 | 6.7 |
| PLK2 | 4.7 |
| CDK10 | 2.9 |
| Erk1/2 | 1.9 |
| CaMK2g | 1.8 |
| NEK6/7 | 0.5 |
| DYRK1B | 0.2 |
| CDK6 | -0.9 |
| CDK5 | -1.5 |
| CHK1 | -1.5 |
| SYK | -2.8 |
| GSK3B | -2.9 |
| Wnk1/2/4 | -5.0 |
| RPS6KC1 (domain 1) | -6.4 |
| p38d | -7.6 |
| DMPK1 | -8.6 |
| PKCa/b | -11.3 |
| SMG1 | -12.6 |

FIG. 17C

| ROCK1/2 | -13.2 |
|---|---|
| MAP3K5 | -14.3 |
| CHED | -14.6 |
| BARK1/2 | -16.0 |
| MST4, YSK1 | -18.0 |
| CK1a | -19.6 |
| BRAF | -27.5 |
| PKR | -30.3 |
| PKN2 | -37.0 |
| LKB1 | -51.1 |
| STLK5 | -73.3 |

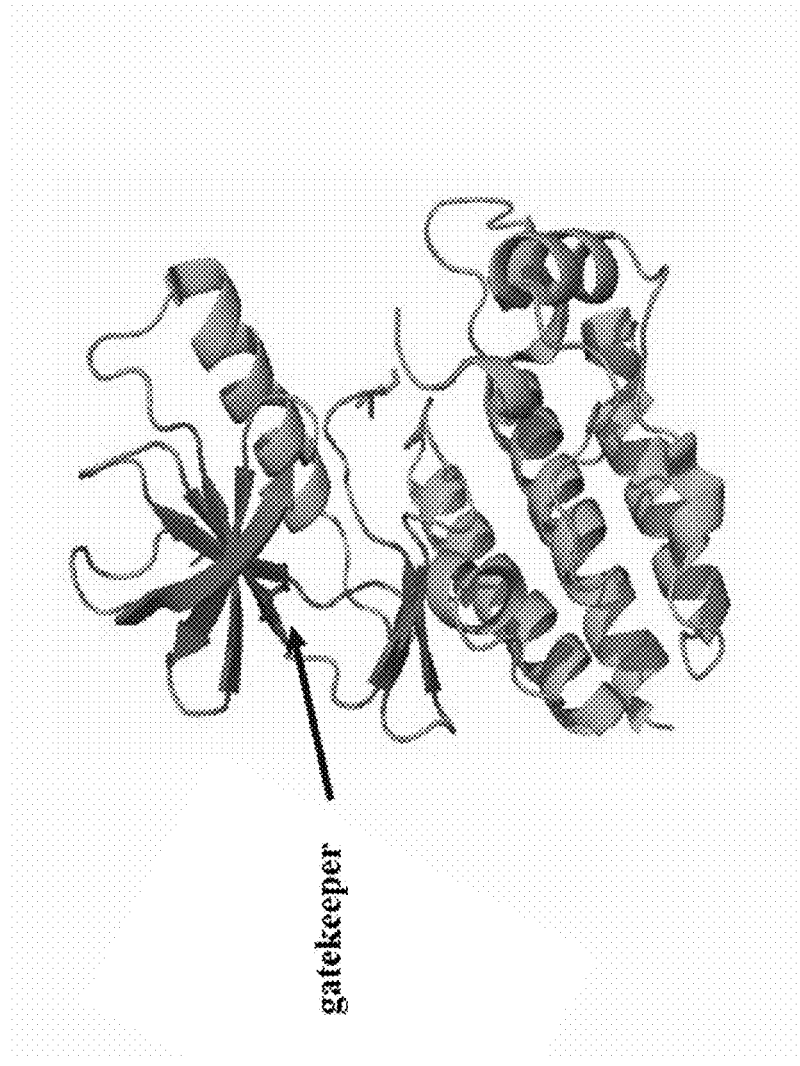
FIG. 18A: XI-1 can suppress B-RAF gatekeeper mutation T529I, which confers resistance in other B-RAF inhibitors

FIG. 19

Cellular IC50 (µM)

| Cells | Genetic status | XL-1 | BAY61-3606 | Sorafenib | SB590885 | PLX4720 | Torin-1 | Dasatinib |
|---|---|---|---|---|---|---|---|---|
| A373-C6 | B-RAF V600E | 0.63 | >10 | 1.50 | 3.60 | 4.60 | ND | ND |
| A375 | B-RAF V600E | 0.18 | 0.40 | 0.98 | 0.03 | 0.10 | 0.02 | 5.17 |
| BRAF/Baf3 | B-RAF T529I & V600E | 0.42 | | 6.60 | 2.90 | >10 | ND | ND |
| BRAF/Baf3 | B-RAF V600E | 0.09 | 0.25 | 0.81 | 0.04 | 0.16 | 0.01 | 5.16 |
| CH-212 | | 1.06 | 0.53 | 4.31 | >10 | >10 | ND | >10 |
| M14 | B-RAF V600E | 0.80 | >10 | 4.34 | 1.11 | 2.50 | >10 | >10 |
| NAE | B-RAF V600E | 0.35 | 1.67 | 1.27 | 1.05 | 0.28 | 0.02 | >10 |
| SK-MEL-5 | B-RAF V600E | 1.64 | 0.65 | 3.39 | 2.10 | 0.06 | 0.04 | >10 |
| TRPM | B-RAF V600E | 0.65 | 0.15 | 1.06 | >10 | >10 | 0.05 | >10 |
| SK-MEL28 | B-RAF V600E | 0.30 | 0.12 | 0.90 | 0.10 | 0.03 | 5.06 | >10 |
| SK-MEL30 | N-RAS Q61R | 1.70 | 6.22 | 5.50 | 5.20 | >10 | ND | >10 |
| HCT116 | | 1.0 | ND | ND | ND | ND | ND | ND |
| HKE3 | | 3.20 | ND | ND | ND | ND | ND | ND |
| HT29 | | 0.20 | ND | ND | ND | 0.59 | ND | ND |
| K029 | B-RAF V600E | 0.19 | ND | ND | ND | >10 | ND | ND |
| M34 | B-RAF V600E | 1.64 | ND | ND | ND | >10 | ND | ND |
| M23 | N-RAS Q61R | 0.85 | ND | ND | ND | >10 | ND | ND |
| K033 | N-RAS Q61R | 1.85 | ND | ND | ND | >10 | ND | ND |

TYPE II RAF KINASE INHIBITORS

RELATED APPLICATIONS

This application is a US National stage application of PCT/US2010/062310 (WO2011/090738), filed on Dec. 29, 2010, which claims priority to U.S. Ser. No. 61/290,884, filed on Dec. 29, 2009. The entire contents of the above-referenced applications are incorporated herein by reference.

TECHNICAL FIELD

The present invention relates to novel compounds which are able to inhibit b-raf and b-raf mutations, and the use of such compounds in the treatment of various diseases, disorders or conditions.

BACKGROUND OF THE INVENTION

Receptor tyrosine kinases and serine/threonine kinases have been implicated in cellular signaling pathways that control cell function, division, growth, differentiation, and apoptosis through reversible phosphorylation of the hydroxyl groups of tyrosine or serine and threonine residues, respectively, in proteins. In signal transduction, for example, extracellular signals are transduced via membrane receptor activation, with amplification and propagation using a complex choreography of cascades of protein phosphorylation, and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyze phosphorylation of certain tyrosyl amino acid residues in various proteins, including themselves, which govern cell growth, proliferation and differentiation.

Downstream of the several RTKs lie several signaling pathways, including the Ras-Raf-MEK-ERK kinase pathway. It is currently understood that activation of Ras GTPase proteins in response to growth factors, hormones, cytokines, etc. stimulates phosphorylation and activation of Raf kinases. These kinases then phosphorylate and activate the intracellular protein kinases MEK1 and MEK2, which in turn phosphorylate and activate other protein kinases, ERK1 and 2. This signaling pathway, also known as the mitogen-activated protein kinase (MAPK) pathway or cytoplasmic cascade, mediates cellular responses to growth signals. The ultimate function of this is to link receptor activity at the cell membrane with modification of cytoplasmic or nuclear targets that govern cell proliferation, differentiation, and survival. Mutations in various Ras GTPases and the B-Raf kinase have been identified that can lead to sustained and constitutive activation of the MAPK pathway, ultimately resulting in increased cell division and survival. As a consequence of this, these mutations have been strongly linked with the establishment, development, and progression of a wide range of human cancers. The biological role of the Raf kinases, and specifically that of B-Raf, in signal transduction is described in Davies, H., et al., Nature (2002) 9:1-6; Garnett, M. J. & Marais, R., Cancer Cell (2004) 6:313-319; Zebisch, A. & Troppmair, J., Cell. Mol. Life. Sci. (2006) 63:1314-1330; Midgley, R. S. & Kerr, D. J., Crit. Rev. One/Hematol. (2002) 44:109-120; Smith, R. A., et al., Curr. Top. Med. Chem. (2006) 6:1071-1089; and Downward, J., Nat. Rev. Cancer (2003) 3:11-22.

The "Erk pathway" is an intracellular signal transduction pathway used by nearly all types of human cells to translate extracellular signals to cellular decisions, including proliferation, differentiation, senescence, or apoptosis (Wellbrock et al., Nat. Rev. Mol. Cell. Biol. 11:875-885 (2004)). One of the invariant components of this pathway is the Ras GTPase, which receives signals from membrane receptors and activates the Raf protein kinases, which activate the Mek protein kinases, which in turn activate the Erk protein kinases. Activated Erk kinases phosphorylate a number of nuclear and cytoplasmic targets to initiate various cellular decisions. The biological importance of Raf in the Erk pathway is underscored by the finding that mutated forms of Raf are associated with certain human malignancies (see e.g. Monia et al., Nature Medicine 2:668-675 (1996); Davies et al., Nature 417:949-954 (2002)). Three distinct genes have been identified in mammals that encode Raf proteins; a-Raf, b-Raf and c-Raf (also known as Raf-1) and isoformic variants that result from differential splicing of mRNA are known (Chong et al., EMBO J. 20:3716-3727 (2001)). The Erk pathway is mutationally activated in a number of human cancers, most often by mutation of the Ras or b-Raf genes. Mutations in Ras and b-Raf genes generally occur in the same tumor types, including cancers of the colon, lung and pancreas and melanoma, but are usually mutually exclusive. This suggests that activation of either Ras or Raf is sufficient for pathway activation and cancer progression.

Naturally occurring mutations of the B-Raf kinase that activate MAPK pathway signaling have been found in a large percentage of human melanomas (Davies (2002) supra) and thyroid cancers (Cohen et al J. Nat. Cancer Inst. (2003) 95 (8) 625-627 and Kimura et al Cancer Res. (2003) 63 (7) 1454-1457), as well as at lower, but still significant, frequencies in the following: Barret's adenocarcinoma, billiary tract carcinomas, breast cancer, cervical cancer, cholangiocarcinoma, central nervous system tumors including primary CNS tumors such as glioblastomas, astrocytomas and ependymomas and secondary CNS tumors (i.e., metastases to the central nervous system of tumors originating outside of the central nervous system), colorectal cancer, including large intestinal colon carcinoma, gastric cancer, carcinoma of the head and neck including squamous cell carcinoma of the head and neck, hematologic cancers including leukemias, acute myelogenous leukemia (AML), myelodysplastic syndromes and chronic myelogenous leukemia; Hodgkin's lymphoma, non-Hodgkin's lymphoma, megakaryoblastic leukemia and multiple myeloma, hepatocellular carcinoma, lung cancer, including small cell lung cancer and non-small cell lung cancer, ovarian cancer, endometrial cancer, pancreatic cancer, pituitary adenoma, prostate cancer, renal cancer, sarcoma, and skin cancers.

By virtue of the role played by the Raf family kinases in these cancers and exploratory studies with a range of preclinical and therapeutic agents, including one selectively targeted to inhibition of B-Raf kinase activity (King A. J., et al., (2006) Cancer Res. 66:11100-11105), it is generally accepted that inhibitors of one or more Raf family kinases will be useful for the treatment of such cancers or other condition associated with Raf kinase.

Mutation of B-Raf has also been implicated in other conditions, including cardio-facio cutaneous syndrome (Rodriguez-Viciana et al Science (2006) 311 (5765) 1287-1290) and polycystic kidney disease (Nagao et al Kidney Int. (2003) 63 (2) 427-437).

Since tumor cells frequently become dependent to one or two key signaling pathways for their survival (see, e.g. Jonkers et al., Cancer Cell. 6:535-538 (2004)), the Erk pathway represents a highly attractive target for drug intervention to treat cancer. Protein kinases in general are considered desirable targets for drug therapy, as evidenced by recent successes in targeting growth factor receptor and intracellular tyrosine kinases. Inhibitors of Mek have shown promise in clinical trials, however, there is ample evidence to indicate Mek-independent Raf signaling that may also contribute to cancer progression (Wellbrock et al, Nat. Rev. Mol. Cell. Biol. 11:875-885 (2004)). Therefore, targeting Raf kinases promises an alternative and complementary approach to treating tumors in which Ras or Raf genes are mutated.

SUMMARY OF THE INVENTION

In one aspect, the invention provides a compound of formula I:

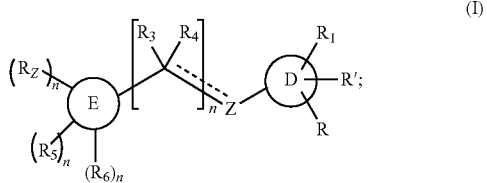

or a pharmaceutically acceptable salt, ester or prodrug thereof,
wherein,
ring D is aryl or heteroaryl;
R is H, halo, or -A-B;
A is $NR_AC(O)$, O, $S(O)_m$, C(O), C(O)O, $C(O)NR_A$, $NR_AC(O)NR_A$, or absent;
B is H, alkyl, alkoxy, cycloalkyl, or aryl, each of which is optionally substituted;
$R_1$ is hydroxyl, alkyl, alkoxy, $C(O)OR_A$, $C(O)NR_AR_B$, or $NR_AR_B$, each of which may be optionally substituted; or H or halo;
R' is absent, or R and R' together with the atoms to which each is attached, form a cycloalkyl, heterocycloalkyl, aryl, or heteroaryl ring, each of which is optionally substituted;
Z is $NR_A$, O, $NR_AC(O)$, $C(O)NR_A$, $CR_3R_4$ or $S(O)_m$;
$R_3$ is H or alkyl;
$R_4$ is H, alkyl, or absent;
or $R_3$ and $R_4$ together with the carbon to which each is attached form C(O);
ring E is monocyclic or bicyclic heteroaryl;
$R_Z$ is $NR_AR_2$;
$R_2$ is H, optionally substituted aryl, optionally substituted heteroaryl, optionally substituted heterocycloalkyl, $C(O)R_A$, $C(O)OR_A$, $C(O)NR_AR_B$, $C(NR_B)R_A$, or $C(NR_B)OR_A$;
$R_5$ is H, halo, alkyl, alkoxy, or thioalkoxy;
$R_6$ is H, $NR_AR_B$, or $OR_A$;
each $R_A$ is independently H, alkyl, alkenyl, cycloalkyl, heterocyclic, aryl or heteroaryl, each of which may be optionally substituted;
each $R_B$ is independently H, alkyl, alkenyl, cycloalkyl, heterocyclic, aryl or heteroaryl, each of which may be optionally substituted;
or, for each occurrence of $NR_AR_B$, $R_A$ and $R_B$ are taken together with the nitrogen atom to which they are attached to form a 3-7 membered heterocycloalkyl ring;

each m is independently 0, 1, or 2; and
each n is independently 0 or 1.

In another aspect, the invention provides a pharmaceutical composition comprising a compound of formula I, or a pharmaceutically acceptable ester, salt, or prodrug thereof, together with a pharmaceutically acceptable carrier.

In one aspect, the invention provides a method of inhibiting a b-raf kinase in a subject, comprising administering to the subject a compound of formula I.

In another aspect, the invention provides a method of treating a disease related to kinase modulation in a subject comprising administering to the subject a compound or pharmaceutically acceptable salt of formula I;
wherein the kinase is selected from b-raf, Abl, Csf1R, EGFR, EphA8, FGFR1,2,3,4, FLT3, KIT, Lok, MAP4K1, MUSK, p38alpha, beta, PDGFRalpha, beta, Ret, Taok3, TNNI3K, Fes, Lyn SRPK1, STK36, TIE2, DDR1, EPHA2, ROIK1, RIOK3, NKF1LK, Src, Tak1, BLK, EphA4, EphB2, Fgr, FLT4, MAP4K2, ANKK1, Frk, Lck, Map4K5, Erbb4, Map4k4, MKNK2, Tec, Flt1, Hck, Tnk2, Txk, BTK, SLK, RiPK1, RIPK2, BIKE, CIT, CDKL2, DRAK, EphB1, JNK2, MLK1, MYLK2, TrkA, B, C, VEGFR2, IKKalpha, PTK2B, MAP4K3, Tie2, Fyn, Zak, DDR2, AurC, Lyn, Hpk1, Gck.

In another aspect, the invention provides a method of treating a disease related to b-raf or b-raf mutation modulation in a subject comprising administering to the subject a compound or pharmaceutically acceptable salt of formula I.

In other aspects, the invention provides a method of treating a disease related to b-raf or b-raf mutation modulation in a subject comprising: administering to the subject identified as in need thereof a compound or pharmaceutically acceptable salt of formula I.

In another aspect, the invention provides a method of treating a disease related to b-raf or b-raf mutation modulation in a subject, wherein the disease is resistant to drug resistant mutations in b-raf, comprising administering to the subject a compound or pharmaceutically acceptable salt of formula I.

In another aspect, the invention provides a method of treating cancer in a subject, wherein the cancer comprises b-raf activated tumors, comprising administering to the subject a compound or pharmaceutically acceptable salt of formula I.

In certain aspects, the invention provides a method of treating cancer in a subject, cancer comprises b-raf activated tumors, wherein the subject is identified as being in need of b-raf inhibition for the treatment of cancer, comprising administering to the subject a compound or pharmaceutically acceptable salt of formula I.

In another aspect, the invention provides a use of a compound of the invention for the preparation of a medicament for the treatment of cancer.

In another aspect, the invention provides a kit comprising a compound or pharmaceutically acceptable salt of formula I capable of inhibiting b-raf or b-raf mutation activity; and instructions for use in treating cancer.

DESCRIPTION OF THE DRAWINGS

FIGS. 1A to 1E: Table 1 shows compounds synthesized using a method described in Example 1.
FIGS. 2A to 2B: Table 2 shows compounds synthesized using a method described in Example 2.
FIGS. 3A to 3E: Table 3 shows compounds synthesized using a method described in Example 3.
FIGS. 4A to 4C: Table 4 shows compounds synthesized using a method described in Example 4.
FIGS. 5A to 5G: Table 5 shows compounds synthesized using a method described in Example 5.

FIGS. 6A to 6B: Table 6 shows compounds synthesized using a method described in Example 6.

FIGS. 7A to 7D: Table 7 shows compounds synthesized using a method described in Example 7.

FIG. 8: Table 8 shows compounds synthesized using a method described in Example 8.

FIGS. 9A to 9C: Table 9 shows compounds synthesized using a method described in Example 9.

FIGS. 10A to 10B: Table 10 shows compounds synthesized using a method described in Example 10.

FIGS. 11A to 11B: Table 11 shows compounds synthesized using a method described in Example 11.

FIGS. 12A to 12D: Table 12 shows compounds synthesized using a method described in Example 12.

FIG. 13: Table 13 shows compounds synthesized using a method described in Example 13.

FIG. 14A shows the dose response IC50 calculation for XI-1 compared to reference Raf inhibitors; FIG. 14B shows the compound IC50 values on b-raf V600E transformed Ba/F3 cells.

FIGS. 15A to 15B: Summary of antiproliferative activity of XI-1 against a variety of cancer cell lines.

FIG. 16A shows kinase targets of XI-1; FIG. 16B shows additional kinase targets of XI-1.

FIGS. 17A to 17C: Additional targets of XI-1 determined using a chemical proteomics approach.

FIGS. 18A to 18B: XI-1 can suppress B-RAF the 'gatekeeper mutation' T529I, which confers resistance in other B-RAF inhibitors.

FIG. 19: Cellular proliferation $IC_{50}$ in micromolar of XI-1 against a panel of different cancer cell lines. $IC_{50}$s also shown for other reference kinase inhibitors in micromolar.

DETAILED DESCRIPTION OF THE INVENTION

Definitions

Figure 1E:
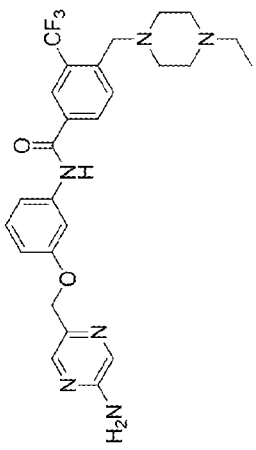
Figure 3D:
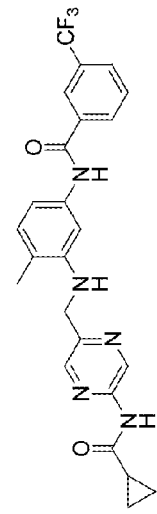
Figure 3E:
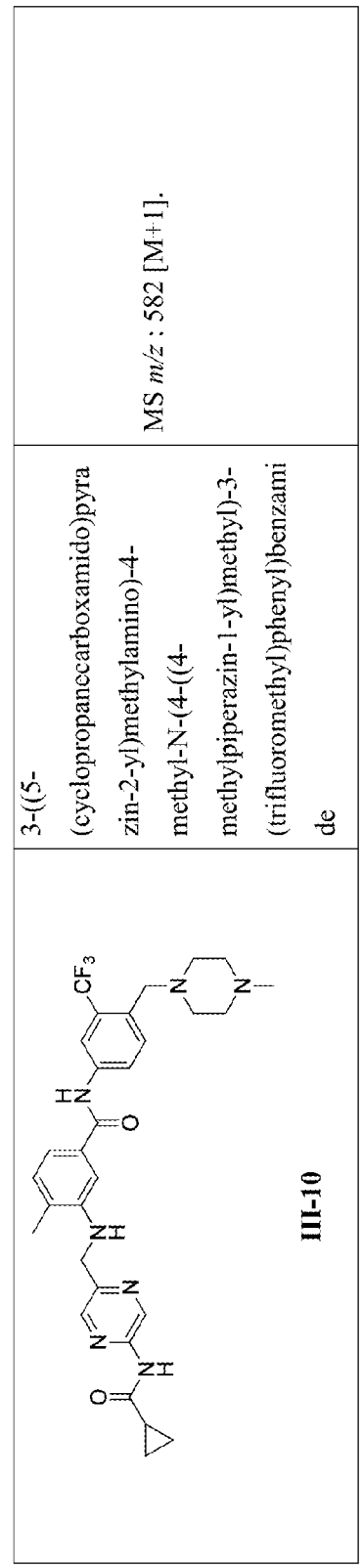

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or polycyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl" or "carbocyclic," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The terms "hal," "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. The term "optionally substituted," refers to groups that are substituted or unsubstituted by independent replacement of one, two, or three or more of the hydrogen atoms thereon with substituents including, but not limited to:

-alkyl, cycloalkyl, aryl, heteroaryl, aralkyl,

—F, —Cl, —Br, —I,

—OH, protected hydroxy,

—NO₂, —CN,

—NH₂, protected amino, —NH—C₁-C₁₂-alkyl, —NH—C₂-C₁₂-alkenyl, —NH—C₂-C₁₂-alkenyl, —NH—C₃-C₁₂-cycloalkyl, —NH-aryl, —NH-heteroaryl, —NH-heterocycloalkyl, -dialkylamino, -diarylamino, -diheteroarylamino, —O—C₁-C₁₂-alkyl, —O—C₂-C₁₂-alkenyl, —O—C₂-C₁₂-alkenyl, —O—C₃-C₁₂ cycloalkyl, -D-aryl, —O-heteroaryl, —O-heterocycloalkyl, —C(O)—C₁-C₁₂-alkyl, —C(O)—C₂-C₁₂-alkenyl, —C(O)—C₂-C₁₂-alkenyl, —C(O)—C₃-C₁₂-cycloalkyl, —C(O)-aryl, —C(O)-heteroaryl, —C(O)-heterocycloalkyl, —CONH₂, —CONH—C₁-C₁₂-alkyl, —CONH—C₂-C₁₂-alkenyl, —CONH—C₂-C₁₂-alkenyl, —CONH—C₃-C₁₂-cycloalkyl, —CONH-aryl, —CONH-heteroaryl, —CONH-heterocycloalkyl, —OCO₂—C₁-C₁₂-alkyl, —OCO₂—C₂-C₁₂-alkenyl, —OCO₂—C₂-C₁₂-alkenyl, —OCO₂—C₃-C₁₂-cycloalkyl, —OCO₂-aryl, —OCO₂-heteroaryl, —OCO₂-heterocycloalkyl, —OCONH₂, —OCONH—C₁-C₁₂-alkyl, —OCONH—C₂-C₁₂-alkenyl, —OCONH—C₂-C₁₂-alkenyl, —OCONH—C₃-C₁₂-cycloalkyl, —OCONH-aryl, —OCONH-heteroaryl, —OCONH-heterocycloalkyl, —NHC(O)—C₁-C₁₂-alkyl, —NHC(O)—C₂-C₁₂-alkenyl, —NHC(O)—C₂-C₁₂-alkenyl, —NHC(O)—C₃-C₁₂-cycloalkyl, —NHC(O)-aryl, —NHC(O)-heteroaryl, —NHC(O)-heterocycloalkyl, —NHCO₂—C₁-C₁₂-alkyl, —NHCO₂—C₂-C₁₂-alkenyl, —NHCO₂—C₂-C₁₂-alkenyl, —NHCO₂—C₃-C₁₂-cycloalkyl, —NHCO₂— aryl, —NHCO₂— heteroaryl, —NHCO₂— heterocycloalkyl, —NHC(O)NH₂, —NHC(O)NH—C₁-C₁₂-alkyl, —NHC(O)NH—C₂-C₁₂-alkenyl, —NHC(O)NH—C₂-C₁₂-alkenyl, —NHC(O)NH—C₃-C₁₂-cycloalkyl, —NHC(O)NH-aryl, —NHC(O)NH-heteroaryl, —NHC(O)NH-heterocycloalkyl, NHC(S)NH₂, —NHC(S)NH—C₁-C₁₂-alkyl, —NHC(S)NH—C₂-C₁₂-alkenyl, —NHC(S)NH—C₂-C₁₂-alkenyl, —NHC(S)NH—C₃-C₁₂-cycloalkyl, —NHC(S)NH-aryl, —NHC(S)NH-heteroaryl, —NHC(S)NH-heterocycloalkyl, —NHC(NH)NH₂, —NHC(NH)NH—C₁-C₁₂-alkyl, —NHC(NH)NH—C₂-C₁₂-alkenyl, —NHC(NH)NH—C₂-C₁₂-alkenyl, —NHC(NH)NH—C₃-C₁₂-cycloalkyl, —NHC(NH)NH-aryl, —NHC(NH)NH-heteroaryl, —NHC(NH)NH-heterocycloalkyl, —NHC(NH)—C₁-C₁₂-alkyl, —NHC(NH)—C₂-C₁₂-alkenyl, —NHC(NH)—C₂-C₁₂-alkenyl, —NHC(NH)—C₃-C₁₂-cycloalkyl, —NHC(NH)-aryl, —NHC(NH)-heteroaryl, —NHC(NH)-heterocycloalkyl, —C(NH)NH—C₁-C₁₂-alkyl, —C(NH)NH—C₂-C₁₂-alkenyl, —C(NH)NH—C₂-C₁₂-alkenyl, —C(NH)NH—C₃-C₁₂-cycloalkyl, —C(NH)NH-aryl, —C(NH)NH-heteroaryl, —C(NH)NH-heterocycloalkyl, —S(O)—C₁-C₁₂-alkyl, —S(O)—C₂-C₁₂-alkenyl, —S(O)—C₂-C₁₂-alkenyl, —S(O)—C₃-C₁₂-cycloalkyl, —S(O)-aryl, —S(O)-heteroaryl, —S(O)-heterocycloalkyl-SO₂NH₂, —SO₂NH—C₁-C₁₂-alkyl, —SO₂NH—C₂-C₁₂-alkenyl, —SO₂NH—C₂-C₁₂-alkenyl, —SO₂NH—C₃-C₁₂-Cycloalkyl, —SO₂NH-aryl, —SO₂NH— heteroaryl, —SO₂NH— heterocycloalkyl, —NHSO₂—C₁-C₁₂-alkyl, —NHSO₂—C₂-C₁₂-alkenyl, —NHSO₂—C₂-C₁₂-alkenyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, -aryl, -arylalkyl, -heteroaryl, -heteroarylalkyl, -heterocycloalkyl, —C₃-C₁₂-cycloalkyl, polyalkoxyalkyl, polyalkoxy, -methoxymethoxy, -methoxyethoxy, —SH, —S—C₁-C₁₂-alkyl, —S—C₂-C₁₂-alkenyl, —S—C₂-C₁₂-alkenyl, —S—C₃-C₁₂-cycloalkyl, —S-aryl, —S-heteroaryl, —S-heterocycloalkyl, or methylthiomethyl.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor (nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), myeloma, multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma; Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma)), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell;

lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Compounds of the Invention

In one aspect, the invention provides a compound of formula I:

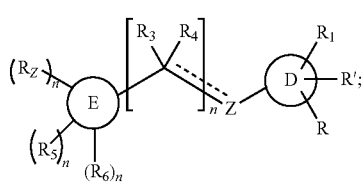

or a pharmaceutically acceptable salt, ester or prodrug thereof,
wherein,
ring D is aryl or heteroaryl;
R is H, halo, or -A-B;
A is $NR_AC(O)$, O, $S(O)_m$, C(O), C(O)O, $C(O)NR_A$, $NR_AC(O)NR_A$, or absent;
B is H, alkyl, alkoxy, cycloalkyl, or aryl, each of which is optionally substituted;
$R_1$ is hydroxyl, alkyl, alkoxy, $C(O)OR_A$, $C(O)NR_AR_B$, or $NR_AR_B$, each of which may be optionally substituted; or H or halo;
R' is absent, or R and R' together with the atoms to which each is attached, form a cycloalkyl, heterocycloalkyl, aryl, or heteroaryl ring, each of which is optionally substituted;
Z is $NR_A$, O, $NR_AC(O)$, $C(O)NR_A$, $CR_3R_4$ or $S(O)_m$;
$R_3$ is H or alkyl;
$R_4$ is H, alkyl, or absent;
or $R_3$ and $R_4$ together with the carbon to which each is attached form C(O);
ring E is monocyclic or bicyclic heteroaryl;
$R_Z$ is $NR_AR_2$;
$R_2$ is H, optionally substituted aryl, optionally substituted heteroaryl, optionally substituted heterocycloalkyl, $C(O)R_A$, $C(O)OR_A$, $C(O)NR_AR_B$, $C(NR_B)R_A$, or $C(NR_B)OR_A$;
$R_5$ is H, halo, alkyl, alkoxy, or thioalkoxy;
$R_6$ is H, $NR_AR_B$, or $OR_A$;
each $R_A$ is independently H, alkyl, alkenyl, cycloalkyl, heterocyclic, aryl or heteroaryl, each of which may be optionally substituted;
each $R_B$ is independently H, alkyl, alkenyl, cycloalkyl, heterocyclic, aryl or heteroaryl, each of which may be optionally substituted;
or, for each occurrence of $NR_AR_B$, $R_A$ and $R_B$ are taken together with the nitrogen atom to which they are attached to form a 3-7 membered heterocycloalkyl ring;
each m is independently 0, 1, or 2; and
each n is independently 0 or 1.

In certain embodiments, ring D is selected from phenyl, naphthyl, tetrahydronaphthyl, indanyl, idenyl, pyridinyl, pyrazinyl, pyrimidinyl, pyrrolyl, pyrazolyl, pyrrolo pyridinyl, thiazolo pyridinyl, imidazolyl, thiazolyl, oxazolyl, isooxazolyl, thiadiazolyl, oxadiazolyl, thiophenyl, furanyl, indazolyl, indolonyl, quinolinyl, isoquinolinyl, benzimidazolyl, benzooxazolyl, and quinoxalinyl.

In a further embodiment, ring D is selected from phenyl, naphthyl, pyrazinyl, pyrimidinyl, pyrrolo pyridinyl, thiazolo pyridinyl, indazolyl, indolonyl, and quinolinyl.

In another embodiment, ring E is selected from phenyl, naphthyl, tetrahydronaphthyl, indanyl, idenyl, pyridinyl, pyrazinyl, pyrimidinyl, pyrrolyl, pyrazolyl, imidazolyl, thiazolyl, oxazolyl, isooxazolyl, thiophenyl, furanyl, indazolyl, indolonyl, quinolinyl, isoquinolinyl, quinazolinyl, 1H-pyrrolo[2,3-b]pyridine, 9H-purine, 7H-pyrrolo[2,3-d]pyrimidine, 1H-pyrazolo[3,4-d]pyrimidine, and quinoxalinyl.

In a further embodiment, ring E is selected from phenyl, naphthyl, pyridinyl, pyrazinyl, and pyrimidinyl.

In a first embodiment, the invention provides a compound of formula II:

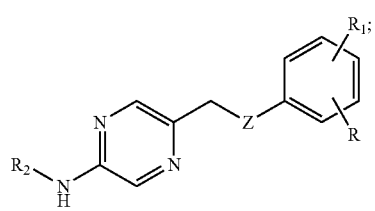

or a pharmaceutically acceptable salt, ester or prodrug thereof,
wherein,
Z is NH or O;
R is H or -A-B;
A is $NR_AC(O)$, O, $S(O)_m$, C(O), C(O)O, $C(O)NR_A$, or absent;
B is alkyl, alkoxy, or aryl, each of which is optionally substituted;
$R_1$ is H, alkyl, alkoxy, or halo; each of which may be optionally substituted;
$R_2$ is H, $C(O)R_A$, $C(O)OR_A$, $C(O)NR_AR_B$, $C(NR_B)R_A$, or $C(NR_B)OR_A$;
each $R_A$ is independently H, alkyl, alkenyl, cycloalkyl, heterocyclic, aryl or heteroaryl, each of which may be optionally substituted;
each $R_B$ is independently H, alkyl, alkenyl, cycloalkyl, heterocyclic, aryl or heteroaryl, each of which may be optionally substituted; and
m is 0, 1, or 2.

In certain embodiments, $R_2$ is H, $C(O)R_A$, $C(O)OR_A$, or $C(O)NR_AR_B$.

In a further embodiment, each $R_A$ is independently H, alkyl, or cycloalkyl, each of which may be optionally substituted; and $R_B$ is H.

In other embodiments, $R_2$ is H,

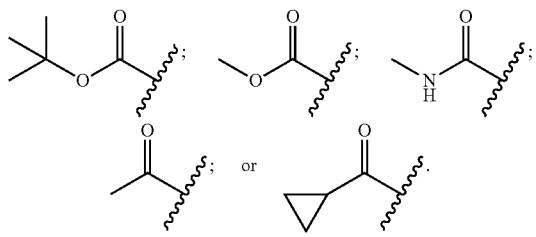

In certain embodiments, $R_1$ is H, alkyl, alkoxy, or halo.

In a further embodiment, $R_1$ is H, methyl, methoxy, or chloro.

In other embodiments, R is H or -A-B; A is $NR_AC(O)$, C(O), C(O)O, $C(O)NR_A$, or absent; and B is alkyl, alkoxy, or aryl, each of which is optionally substituted.

In a further embodiment, A is NHC(O), C(O)O, C(O)NH, or absent.

In a further embodiment, B is phenyl, methyl, or methoxy; each of which is optionally substituted.

In other further embodiments, B is optionally substituted with alkyl, alkenyl, alkynyl, haloalkyl, alkoxy, cycloalkyl, heterocycloalkyl, aryl, heteroaryl, or hydroxyl, each of which is optionally substituted.

In certain embodiments, R is selected from H, methyl, methoxy,

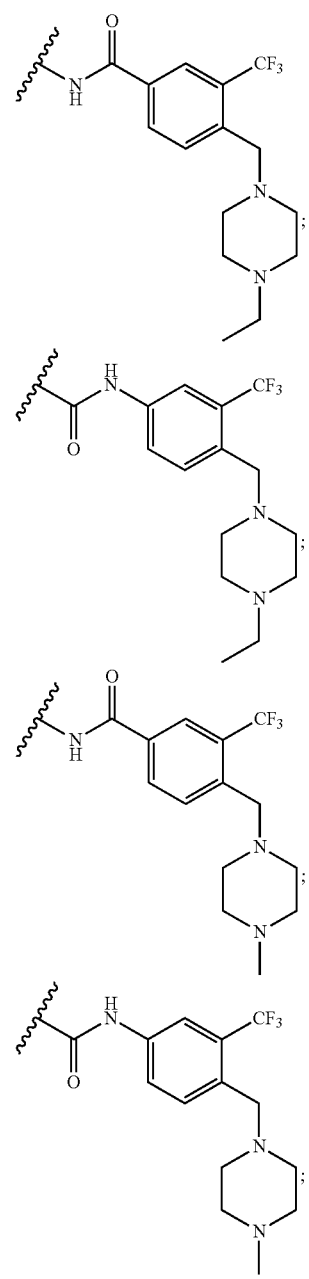

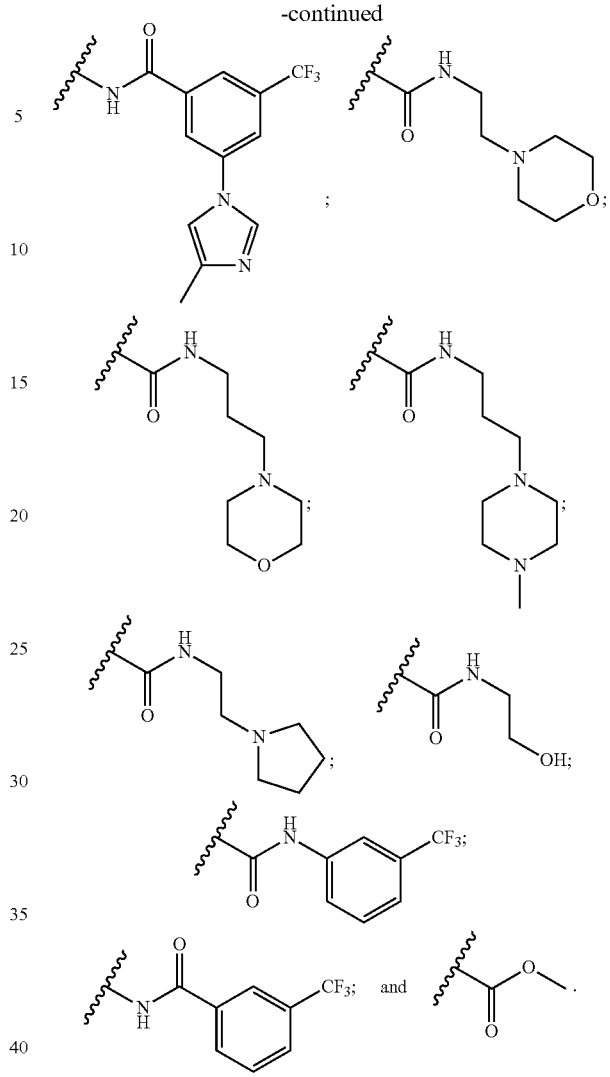

In a second embodiment, the invention provides a compound of formula III:

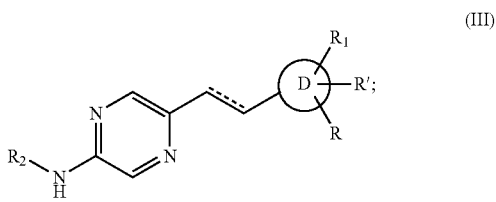

or a pharmaceutically acceptable salt, ester or prodrug thereof, wherein,
ring D is aryl or heteroaryl;
R is H, halo, or -A-B;
A is $NR_AC(O)$, O, $S(O)_m$, C(O), C(O)O, $C(O)NR_A$, or absent;
B is H, alkyl, cycloalkyl, or aryl, each of which is optionally substituted;
$R_1$ is H, hydroxyl, alkyl, alkoxy, $C(O)OR_A$, $C(O)NR_AR_B$, $NR_AR_B$, or halo; each of which may be optionally substituted;

R' is absent, or R and R' together with the atoms to which each is attached, form a cycloalkyl, heterocycloalkyl, aryl, or heteroaryl ring, each of which is optionally substituted;

$R_2$ is H, optionally substituted aryl, optionally substituted heteroaryl, optionally substituted heterocycloalkyl, $C(O)R_A$, $C(O)OR_A$, $C(O)NR_AR_B$, $C(NR_B)R_A$, or $C(NR_B)OR_A$;

each $R_A$ is independently H, alkyl, alkenyl, cycloalkyl, heterocyclic, aryl or heteroaryl, each of which may be optionally substituted;

each $R_B$ is independently H, alkyl, alkenyl, cycloalkyl, heterocyclic, aryl or heteroaryl, each of which may be optionally substituted; and m is 0, 1, or 2.

In certain embodiments, $R_2$ is H, optionally substituted aryl, or optionally substituted heteroaryl.

In other embodiments, $R_2$ is H, phenyl, pyridyl, pyrimidinyl, each of which is optionally substituted.

In a further embodiment, $R_2$ is H,

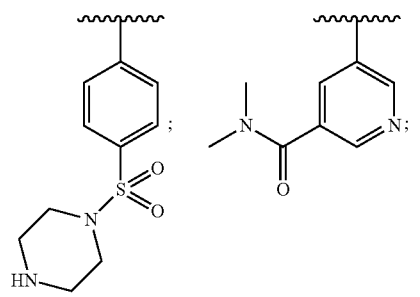

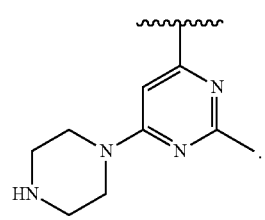

In various embodiments, ring D is phenyl, pyrrolo pyridine, benzothiazole, indazole, pyrazine, or indolinone.

In other embodiments, $R_1$ is H, hydroxyl, alkyl, $NR_AR_B$, or halo; each of which may be optionally substituted.

In other embodiments, R is H, halo, or -A-B; A is $NR_AC(O)$, O, $S(O)_m$, C(O), C(O)O, $C(O)NR_A$, or absent; and B is alkyl, cycloalkyl, or aryl, each of which is optionally substituted.

In various embodiments, A is NHC(O), C(O)O, C(O)NH, or absent.

In a further embodiment, B is H, alkyl, cycloalkyl, or aryl, each of which is optionally substituted.

In another further embodiment, B is optionally substituted with alkyl, alkenyl, alkynyl, haloalkyl, alkoxy, cycloalkyl, heterocycloalkyl, aryl, heteroaryl, halo, or hydroxyl, each of which is optionally substituted.

In other embodiments, R is H, methyl, Cl, F, COOH, C(O)NHCH$_3$,

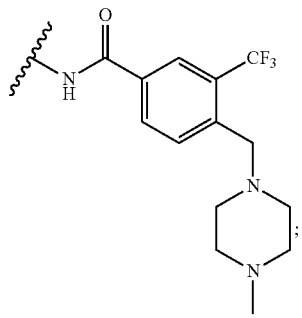

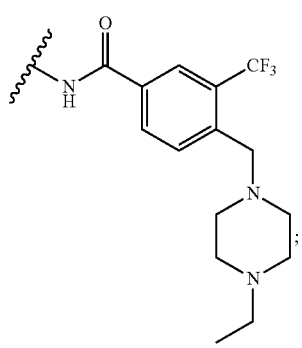

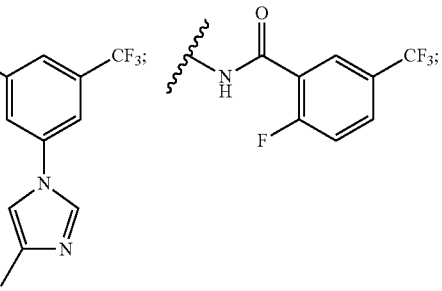

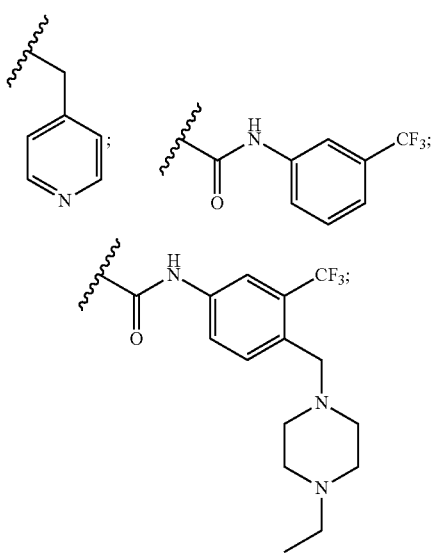

-continued

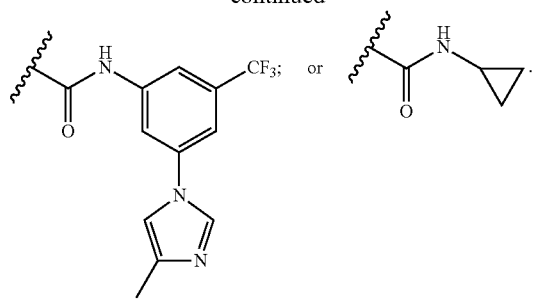

In a third embodiment, the invention provides a compound of formula IV:

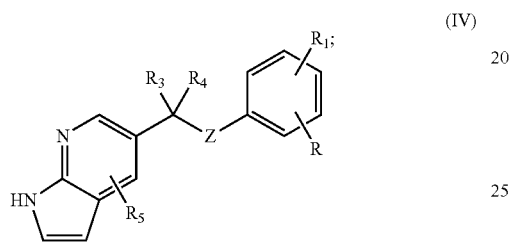

or a pharmaceutically acceptable salt, ester or prodrug thereof,
wherein,
R is H or -A-B;
A is $NR_AC(O)$, O, $S(O)_m$, C(O), C(O)O, $C(O)NR_A$, or absent;
B is alkyl or aryl, each of which is optionally substituted;
$R_1$ is H, alkyl, alkoxy, or halo; each of which may be optionally substituted;
Z is $NR_A$, O, or $S(O)_m$;
$R_3$ is H or alkyl;
$R_4$ is H or alkyl;
or $R_3$ and $R_4$ together with the carbon to which each is attached form C(O);
$R_5$ is H, halo, alkoxy, or thioalkoxy,
each $R_A$ is independently H, alkyl, alkenyl, cycloalkyl, heterocyclic, aryl or heteroaryl, each of which may be optionally substituted; and
each m is independently 0, 1, or 2.

In one embodiment, Z is $NR_A$ or O; $R_3$ is H; $R_4$ is H; or $R_3$ and $R_4$ together with the carbon to which each is attached form C(O).

In a further embodiment, Z is NH or O.

In certain embodiments, $R_5$ is H, halo, alkoxy, or thioalkoxy.

In a further embodiment, $R_5$ is H, Cl, methoxy, or S(i-Pr).

In other embodiments, $R_1$ is H, alkyl, or alkoxy; each of which may be optionally substituted.

In another embodiment, R is -A-B; A is $NR_AC(O)$ or $C(O)NR_A$; and B is alkyl or aryl, each of which is optionally substituted.

In various embodiments, A is NHC(O) or C(O)NH.

In other embodiments, B is alkyl or aryl, each of which is optionally substituted.

In a further embodiment, B is optionally substituted with alkyl, alkenyl, alkynyl, haloalkyl, alkoxy, cycloalkyl, heterocycloalkyl, aryl, heteroaryl, halo, or hydroxyl, each of which is optionally substituted.

In another embodiment, R is

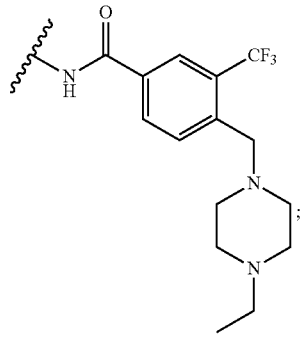

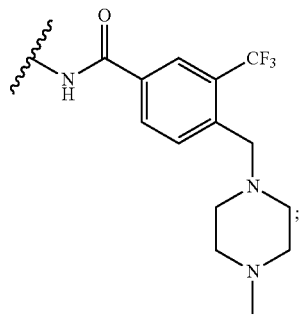

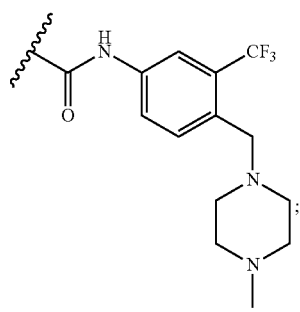

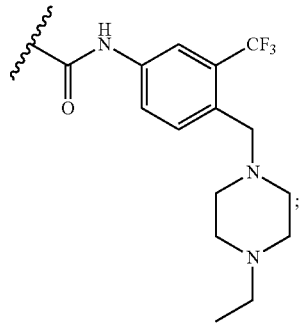

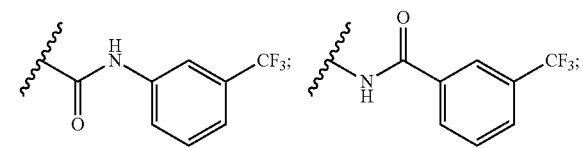

19

-continued

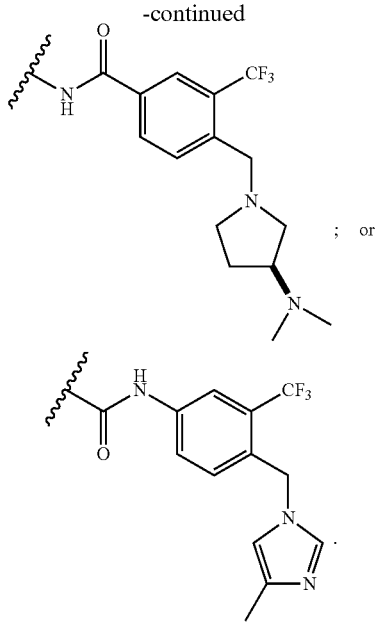

; or

In a fourth embodiment, the invention provides a compound of formula V:

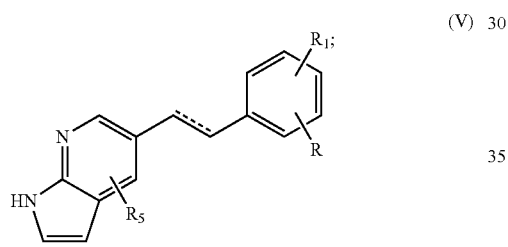

(V)

or a pharmaceutically acceptable salt, ester or prodrug thereof,
wherein,
R is H or -A-B;
A is NR$_A$C(O), O, S(O)$_m$, C(O), C(O)O, C(O)NR$_A$, or absent;
B is alkyl or aryl, each of which is optionally substituted;
R$_1$ is H, alkyl, alkoxy, or halo; each of which may be optionally substituted;
R$_5$ is H, halo, alkoxy, or thioalkoxy,
each R$_A$ is independently H, alkyl, alkenyl, cycloalkyl, heterocyclic, aryl or heteroaryl, each of which may be optionally substituted; and
m is 0, 1, or 2.
In one embodiment, R$_5$ is halo or alkoxy.
In a further embodiment, R$_5$ is Cl or methoxy.
In other embodiments, R$_1$ is alkyl, which may be optionally substituted.
In certain embodiments, R is -A-B; A is NR$_A$C(O) or C(O)NR$_A$; and B is alkyl or aryl, each of which is optionally substituted.
In a further embodiment, A is NHC(O) or C(O)NH.
In a further embodiment, B is alkyl or aryl, each of which is optionally substituted.
In a further embodiment, B is optionally substituted with alkyl, alkenyl, alkynyl, haloalkyl, alkoxy, cycloalkyl, heterocycloalkyl, aryl, heteroaryl, halo, or hydroxyl, each of which is optionally substituted.

20

In certain embodiments, R is

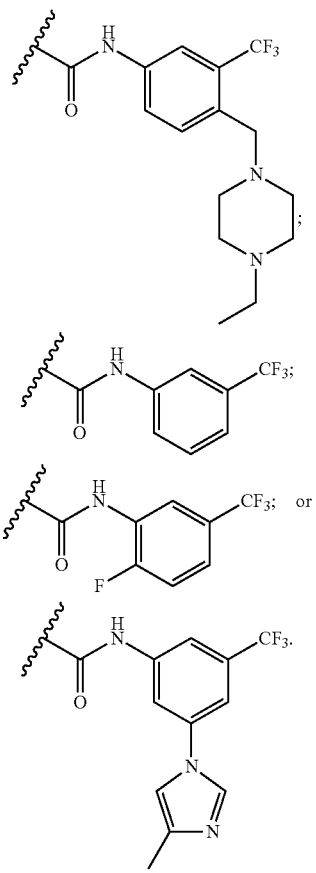

In a fifth embodiment, the invention provides a compound of formula VI:

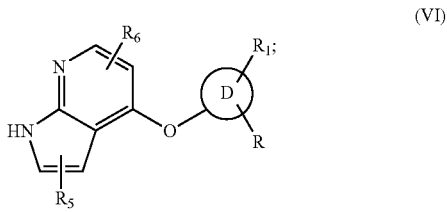

(VI)

or a pharmaceutically acceptable salt, ester or prodrug thereof,
wherein,
ring D is aryl or heteroaryl;
R is H, halo, or -A-B;
A is NR$_A$C(O), O, S(O)$_m$, C(O), C(O)O, C(O)NR$_A$, or absent;
B is alkyl, cycloalkyl, or aryl, each of which is optionally substituted;
R$_1$ is H, hydroxyl, alkyl, alkoxy, C(O)OR$_A$, C(O)NR$_A$R$_B$, NR$_A$R$_B$, or halo; each of which may be optionally substituted;
R$_6$ is H, NR$_A$R$_B$, or OR$_A$;
R$_5$ is H, halo, alkoxy, or thioalkoxy,
each R$_A$ is independently H, alkyl, alkenyl, cycloalkyl, heterocyclic, aryl or heteroaryl, each of which may be optionally substituted;

each $R_B$ is independently H, alkyl, alkenyl, cycloalkyl, heterocyclic, aryl or heteroaryl, each of which may be optionally substituted; and m is 0, 1, or 2.

In one embodiment, $R_6$ is H or $NR_AR_B$.

In certain embodiments, $R_A$ is an optionally substituted aryl and $R_B$ is H.

In other embodiments, $R_5$ is H or Cl.

In another embodiment, ring D is phenyl, naphthyl, indolonyl, or quinolinyl.

In a further embodiment, $R_1$ is H.

In another further embodiment, R is -A-B; A is $NR_AC(O)$ or $C(O)NR_A$; and B is alkyl or aryl, each of which is optionally substituted.

In a further embodiment, A is NHC(O) or C(O)NH.

In another further embodiment, B is alkyl or phenyl, each of which is optionally substituted.

In a further embodiment, B is optionally substituted with alkyl, alkenyl, alkynyl, haloalkyl, alkoxy, cycloalkyl, heterocycloalkyl, aryl, heteroaryl, halo, or hydroxyl, each of which is optionally substituted.

In certain embodiments, R is

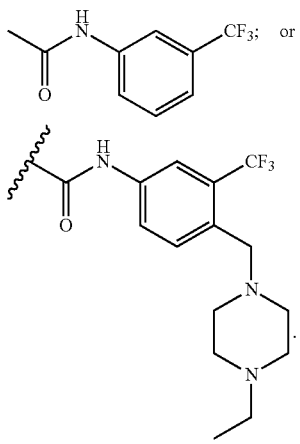

In certain embodiments, the invention provides a compound of formula VII:

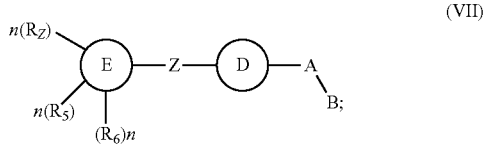

(VII)

or a pharmaceutically acceptable salt, ester or prodrug thereof,
wherein,
ring D is aryl;
A is $NR_AC(O)$, O, $S(O)_m$, C(O), C(O)O, $C(O)NR_A$, $NR_AC(O)NR_A$, or absent;
B is H, alkyl, alkoxy, cycloalkyl, or aryl, each of which is optionally substituted;
Z is $NR_A$, O, $NR_AC(O)$, $C(O)NR_A$, or $S(O)_m$;
ring E is monocyclic or bicyclic heteroaryl;
$R_Z$ is $NR_AR_2$;
$R_2$ is H, optionally substituted aryl, optionally substituted heteroaryl, optionally substituted heterocycloalkyl, $C(O)R_A$, $C(O)OR_A$, $C(O)NR_AR_B$, $C(NR_B)R_A$, or $C(NR_B)OR_A$;

$R_5$ is H, halo, alkyl, alkoxy, or thioalkoxy;
$R_6$ is H, $NR_AR_B$, or $OR_A$;
each $R_A$ is independently H, alkyl, alkenyl, cycloalkyl, heterocyclic, aryl or heteroaryl, each of which may be optionally substituted;
each $R_B$ is independently H, alkyl, alkenyl, cycloalkyl, heterocyclic, aryl or heteroaryl, each of which may be optionally substituted; and
each n is independently 0 or 1.

In another aspect, the invention provides a pharmaceutical composition comprising a compound of formula I, or a pharmaceutically acceptable ester, salt, or prodrug thereof, together with a pharmaceutically acceptable carrier.

Representative compounds of the invention include, but are not limited to, the following compounds found in FIGS. 1A to 13 (and Tables 1-13) and the Examples below.

The invention also provides for a pharmaceutical composition comprising a compound of formula I, or a pharmaceutically acceptable ester, salt, or prodrug thereof, together with a pharmaceutically acceptable carrier.

In another aspect, the invention provides a method of method of synthesizing a compound of formula I.

The synthesis of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3.sup.rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In one aspect, the invention provides a method of inhibiting a b-raf kinase in a subject, comprising administering to the subject a compound of formula I.

In one embodiment, the b-raf kinase is a mutation.

In another embodiment, the b-raf kinase mutation is V600E, T529I, or V600E/T529I.

In another aspect, the invention provides a method of treating a disease related to kinase modulation in a subject comprising administering to the subject a compound or pharmaceutically acceptable salt of formula I;
wherein the kinase is selected from b-raf, Abl, Csf1R, EGFR, EphA8, FGFR1,2,3,4, FLT3, KIT, Lok, MAP4K1, MUSK, p38alpha, beta, PDGFRalpha, beta, Ret, Taok3, TNNI3K, Fes, Lyn SRPK1, STK36, TIE2, DDR1, EPHA2, ROIK1, RIOK3, NKF1LK, Src, Tak1, BLK, EphA4, EphB2, Fgr, FLT4, MAP4K2, ANKK1, Frk, Lck, Map4K5, Erbb4, Map4k4, MKNK2, Tec, Flt1, Hck, Tnk2, Txk, BTK, SLK, RiPK1, RIPK2, BIKE, CIT, CDKL2, DRAK, EphB1, JNK2, MLK1, MYLK2, TrkA,B,C, VEGFR2, IKKalpha, PTK2B, MAP4K3, Tie2, Fyn, Zak, DDR2, AurC, Lyn, Hpk1, and Gck.

In one embodiment, the kinase is selected from b-raf b-raf, Abl, Csf1R, EGFR, EphA8, FGFR1,2,3,4, FLT3, KIT, Lok, MAP4K1, MUSK, p38alpha, beta, PDGFRalpha, beta, Ret, Taok3, TNNI3K, Fes, Lyn SRPK1, STK36, TIE2, DDR1, EPHA2, ROIK1, RIOK3, NKF1LK, Src, Tak1, BLK, EphA4, EphB2, Fgr, FLT4, MAP4K2, ANKK1, Frk, Lck, Map4K5, Erbb4, Map4k4, MKNK2, Tec, Flt1, Hck, Tnk2, Txk, BTK, SLK, RiPK1, RIPK2, BIKE, CIT, CDKL2, DRAK, EphB1, JNK2, MLK1, MYLK2, TrkA,B,C, VEGFR2, IKKalpha, PTK2B, MAP4K3, Tie2, Fyn, Zak, DDR2, AurC, Lyn, Hpk1, and Gck.

In another aspect, the invention provides a method of treating a disease related to b-raf or b-raf mutation modulation in a subject comprising administering to the subject a compound or pharmaceutically acceptable salt of formula I.

In other aspects, the invention provides a method of treating a disease related to b-raf or b-raf mutation modulation in a subject comprising: administering to the subject identified as in need thereof a compound or pharmaceutically acceptable salt of formula I.

In various embodiments, the modulation is inhibition.

In other embodiments, the b-raf mutation is V600E, T529I, or V600E/T529I.

In certain embodiments, the disease is cancer or a proliferation disease.

In a further embodiment, the disease is melanoma, lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In certain embodiments, the subject is administered an additional therapeutic agent.

In a further embodiment, the compound and the additional therapeutic agent are administered simultaneously or sequentially.

In various embodiments, the additional therapeutic is a b-raf inhibitor.

In one embodiment, the additional therapeutic is a clinical b-raf inhibitor that directly targets the b-raf ATP site.

In a further embodiment, the additional therapeutic is sorafenib, Raf265, AZ628, PLX-4032, PLX-4720, gefitinib, erlotinib, lapatinib, XL-647, HKI-272, BIBW2992, AV-412, CI-1033, PF00299804, BMS 690514, cetuximab, panitumumab, or matuzumab.

In another aspect, the invention provides a method of treating a disease related to b-raf or b-raf mutation modulation in a subject, wherein the disease is resistant to drug resistant mutations in b-raf, comprising administering to the subject a compound or pharmaceutically acceptable salt of formula I.

In certain embodiments, the b-raf mutation is V600E, T529I, or V600E/T529I.

In another aspect, the invention provides a method of treating cancer in a subject, wherein the cancer comprises b-raf activated tumors, comprising administering to the subject a compound or pharmaceutically acceptable salt of formula I.

In certain aspects, the invention provides a method of treating cancer in a subject, cancer comprises b-raf activated tumors, wherein the subject is identified as being in need of b-raf inhibition for the treatment of cancer, comprising administering to the subject a compound or pharmaceutically acceptable salt of formula I.

In various embodiments, the disease is melanoma, lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In certain embodiments, the invention provides a method as described above wherein the subject is a human.

In another aspect, the invention provides a kit comprising a compound or pharmaceutically acceptable salt of formula I capable of inhibiting b-raf or b-raf mutation activity; and instructions for use in treating cancer.

In certain aspects, the invention provides type II kinase inhibitors that target the mutant (V600E) b-raf pathway. Such compounds are weak direct inhibitors of b-raf and predominantly target a number of kinases upstream of b-raf. Thus, the compounds of the invention are b-raf pathway inhibitors.

In another embodiment, the present invention provides a method for treating or lessening the severity of a kinase disease, condition, or disorder where inhibition of a kinase is implicated in the treatment of the disease, wherein the kinase is selected from ABL1, ABL2, BRAF, CSF1R, EGFR, EPHA8, FGFR4, FLT3, KIT, LOK, MAP4K1, MUSK, p38-beta, PDGFRA, PDGFRB, RET, TAOK3, or TNNI3K.

In other embodiments, present invention provides a method for treating or lessening the severity of a kinase disease, condition, or disorder where inhibition of a kinase is implicated in the treatment of the disease, wherein the kinase is selected from FES, LYN, p38-alpha, SRPK1, STK36, TIE2, DDR1, EPHA2, RIOK1, RIOK3, SNF1LK, SRC, TAK1, BLK, EPHA4, EPHB2, FGR, FLT4, MAP4K2, ANKK1, FRK, LCK, MAP4K5, EGFR, ERBB4, MAP4K4, MKNK2, TEC, FLT1, HCK, TNK2, TXK, BTK, SLK, RIPK1, RIPK2, BIKE, CIT, CDKL2, DRAK1, EPHB1, JNK2, BRAF, MLK1, MYLK2, TRKB, VEGFR2, YES, IKK-alpha, PTK2B, MAP4K3, TIE1, FYN, FGFR1, ZAK, DDR2, RAF1, or AURKC.

In other embodiments, present invention provides a method for treating or lessening the severity of a kinase disease, condition, or disorder where inhibition of a kinase is implicated in the treatment of the disease, wherein the kinase is selected from LYN, CSK, ABL1/2, TAO1/3, HPK1, FGR, p38a, FES, FER, TAO2, KHS1/2, AurA/B/C, MAP3K2, PYK2, MPSK1, p38a, NEK9, PKD1/2, LOK, IRAK4, MST2, NEK9, PLK1, MST1, CK2a2, GSK3A, CDK7, AMPKa1/2, IRE1, AurA, MARK3, p38d/g, KSER, PIP5K2a, STLK5, MAP2K4, PITSLRE, CDK2, RSK1/2/3, PHKg2, PLK2, CDK10, Erk1/2, CaMK2g, NEK6/7, DYRK1B, CDK6, CDK5, CHK1, SYK, GSK3B, Wnk1/2/4, RPS6KCl, p38d, DMPK1, PKCa/b, SMG1, ROCK1/2, MAP3K5, CHED, BARK1/2, MST4, YSK1, CK1a, BRAF, PKR, PKN2, LKB1, or STLK5.

In another aspect, the present invention provides a method for treating or lessening the severity of a kinase disease, condition, or disorder where inhibition of b-raf is implicated in the treatment of the disease.

As inhibitors of b-raf kinases, the compounds and compositions of this invention are particularly useful for treating or lessening the severity of a disease, condition, or disorder where b-raf is implicated in the disease, condition, or disorder. In one aspect, the present invention provides a method for treating or lessening the severity of a disease, condition, or disorder where related to b-raf. In one embodiment, the disease is related to a mutant b-raf such as V600E.

In another aspect, the present invention provides a method for treating or lessening the severity of a kinase disease, condition, or disorder where inhibition of b-raf is implicated in the treatment of the disease.

In other aspects, the invention is directed towards provides a method for treating or lessening the severity of a b-raf related disease, condition, or disorder wherein b-raf mutations have provided for resistance to known drugs. In one embodiment, the mutation is T529I.

In a further embodiment, the disease is melanoma, lung cancer, colon cancer, breast cancer, prostate cancer, liver cancer, pancreas cancer, brain cancer, kidney cancer, ovarian cancer, stomach cancer, skin cancer, melanoma, leukemia, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, solid tumors, colorectal cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, bladder cancer, cervical cancer, squamous cell and/or basal cell cancers, prostate cancer, renal cell carcinoma, or other known cancers that affect epithelial cells throughout the body.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intraepithelial tissue.

In other embodiments, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or Canine B-Cell Lymphoma.

In a further embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, or lymphoma.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

In certain embodiments, the disease is cancer. In a further embodiment, the disease is melanoma.

In certain embodiments, the invention provides a method of treatment of any of the disorders described herein, wherein the subject is a human.

As inhibitors of b-raf kinases and b-raf mutations thereof, the compounds and compositions of this invention are also useful in biological samples. One aspect of the invention relates to inhibiting b-raf kinase activity in a biological sample, which method comprises contacting said biological sample with a compound of the invention or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of b-raf kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of b-raf kinases, and mutations thereof, in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as b-raf kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Combination Therapy

Compounds of the invention can be administered in therapeutically effective amounts in combination with one or more therapeutic agents (pharmaceutical combinations). For example, synergistic effects can occur with other anti-proliferative, anti-cancer, immunomodulatory or anti-inflammatory substances. Where the compounds of the invention are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect, the present invention provides a method for treating or lessening the severity of a kinase disease, condition, or disorder where inhibition of b-raf is implicated in the treatment of the disease, and the use of a b-raf inhibitor compound of the invention is used in combination with any current clinical b-raf inhibitor that directly targets the b-raf ATP site. Such compounds include Sorafenib, Raf265, SB-590885, PLX4032, PLX4720, or AZ628, some of which are provided below:

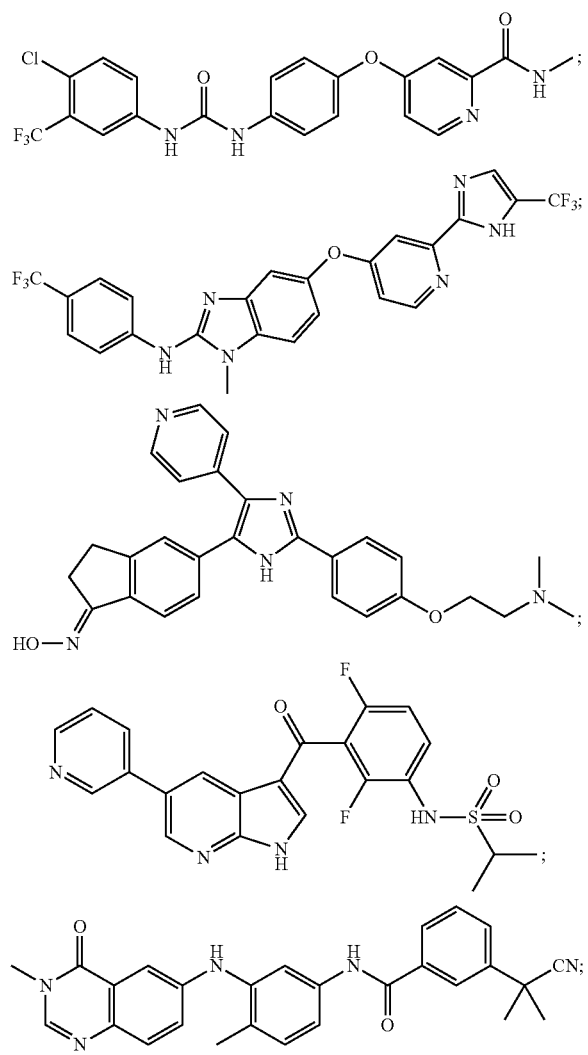

-continued

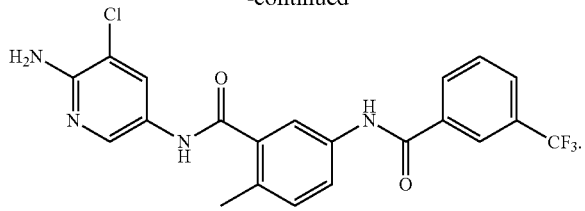

In one aspect of the invention, the compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43.sup.abl, ARG); BTK (e.g. ITK/EMT, TEC); CSK, FAK, FPS, JAK, SRC, BMX, FER, CDK and SYK.

In another aspect of the invention, the subject compounds may be administered in combination with one or more agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Irinotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor a; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

In certain embodiments, these compositions optionally further comprise one or more additional therapeutic agents. For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept18 and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, antileukemic agents, and growth factors; and agents for treating immunodeficiency disorders such as gamma globulin.

Pharmaceutical Compositions

In another aspect, the invention provides a pharmaceutical composition comprising a compound of formula I, or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The compounds of the invention may be formulated into pharmaceutical compositions for administration to animals or humans.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

N-(3-((5-aminopyrazin-2-yl)methylamino)-4-methylphenyl)-4-((4-ethylpiperazin-1-yl)methyl)-3-(trifluoromethyl)benzamide

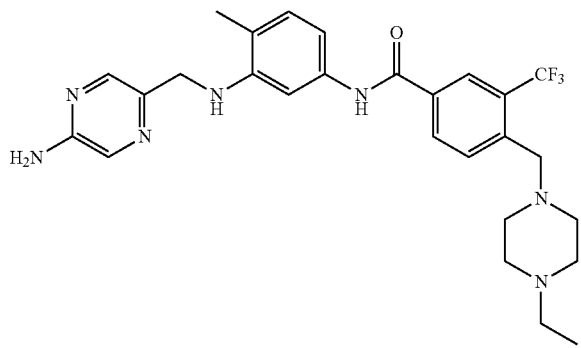 [SMILES: CCN1CCN(Cc2ccc(C(=O)Nc3ccc(C)c(NCc4cnc(N)cn4)c3)cc2C(F)(F)F)CC1]

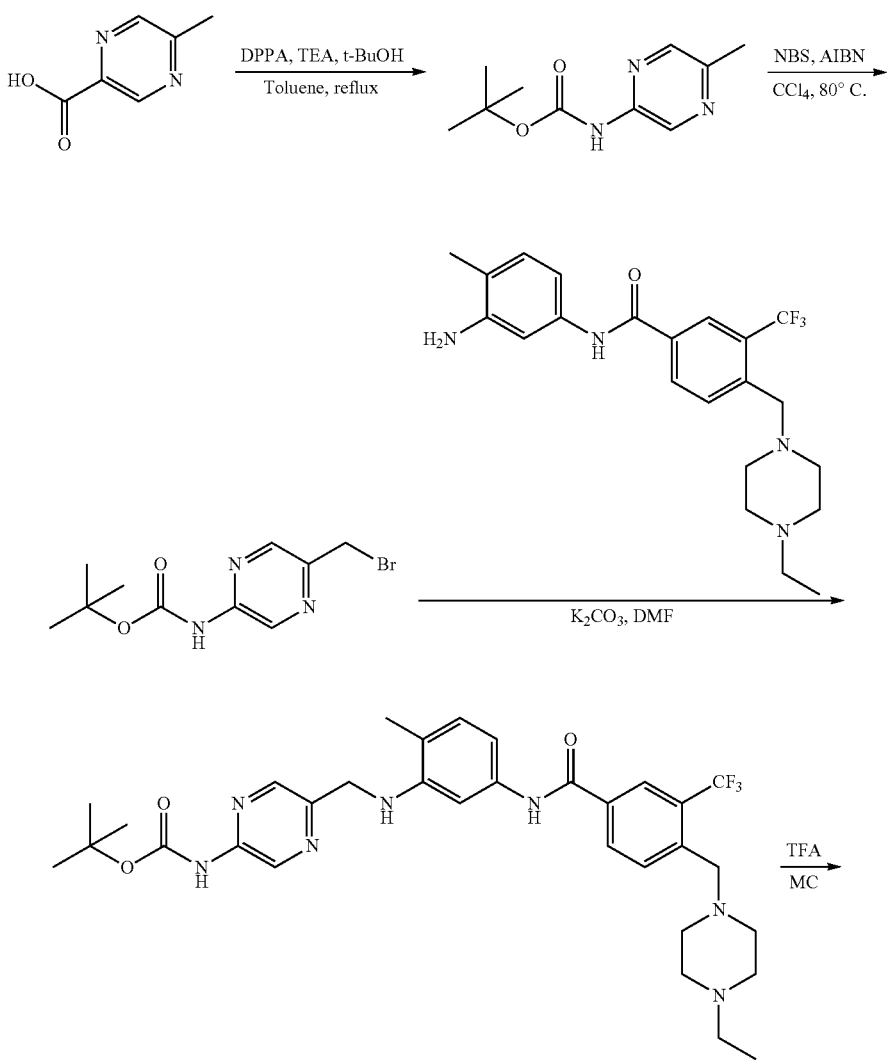

Scheme 1.

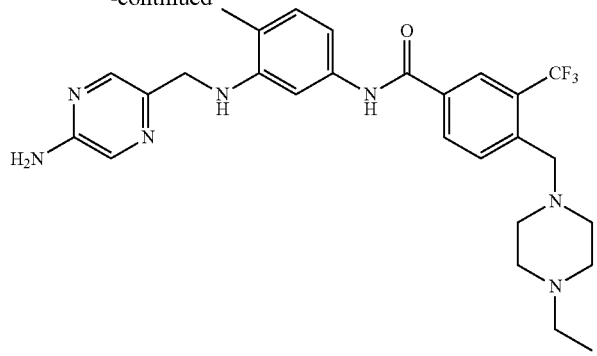

A. tert-butyl 5-methylpyrazin-2-ylcarbamate

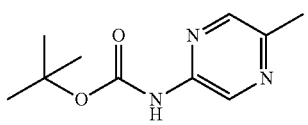

To a solution of 5-methylpyrazine-2-carboxylic acid (500 mg, 3.62 mmol) in toluene (12 mL) were added DPPA (0.85 mL, 3.98 mmol), TEA (1.01 mL, 7.24 mmol) and tert-butanol (3.4 mL, 36.2 mmol). The reaction mixture was refluxed for 6 hours after which, it was partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product was purified by flash chromatography using (10% Ethyl acetate/Hexane) as a solvent to afford title compound (530 mg, 70% yield). $^1$H NMR (600 MHz, CDCl$_3$) δ 9.15 (s, 1H), 8.08 (s, 1H), 7.61 (s, 1H), 2.50 (s, 3H), 1.55 (s, 9H). MS m/z: 210 [M+1].

B. tert-butyl 5-(bromomethyl)pyrazin-2-ylcarbamate

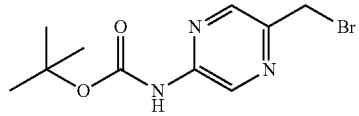 [SMILES: CC(C)(C)OC(=O)Nc1cnc(CBr)cn1]

To a solution tert-butyl 5-methylpyrazin-2-ylcarbamate (500 mg, 2.39 mmol) in CCl$_4$ (8.0 mL) were added NBS (446 mg, 2.51 mmol) and AIBN (117 mg, 0.72 mmol). The reaction mixture was stirred for 4 hours at 80° C. after which, it was partitioned between CH$_2$Cl$_2$ and water. The organic layer was separated and the aqueous layer was extracted with CH$_2$Cl$_2$. The combined organic extracts were washed with brine, dried over MgSO$_4$, celite filtered and concentrated under reduced pressure. The crude product was purified by flash chromatography using (10% Ethyl acetate/Hexane) as a solvent to afford title compound (520 mg, 75% yield). $^1$H NMR (600 MHz, CDCl$_3$) δ 9.29 (s, 1H), 8.95 (s, 1H), 8.37 (s, 1H), 4.38 (s, 2H), 1.57 (s, 9H). MS m/z: 288 [M+1].

C. tert-butyl 5-((5-(4-((4-ethylpiperazin-1-yl)methyl)-3-(trifluoromethyl)benzamido)-2-methylphenylamino)methyl)pyrazin-2-ylcarbamate

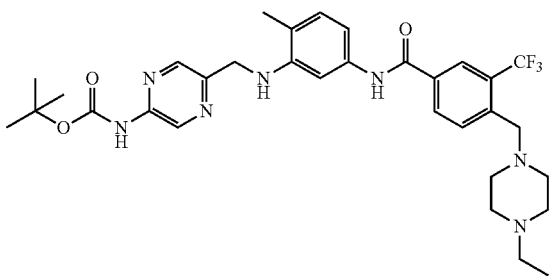 [SMILES: CCN1CCN(Cc2ccc(C(=O)Nc3ccc(C)c(NCc4cnc(NC(=O)OC(C)(C)C)cn4)c3)cc2C(F)(F)F)CC1]

To a solution N-(3-amino-4-methylphenyl)-4-((4-ethylpiperazin-1-yl)methyl)-3-(trifluoromethyl)benzamide (70 mg, 0.17 mmol) in DMF (0.5 mL) were added K$_2$CO$_3$ (69 mg, 0.50 mmol) and tert-butyl 5-(bromomethyl)pyrazin-2-ylcarbamate (48 mg, 0.17 mmol). The reaction mixture was stirred for 8 hours at room temperature after which, it was partitioned between ethyl acetate and water. The organic layer was separated and the aqueous layer was extracted with ethyl acetate. The combined organic extracts were washed with brine, dried over MgSO$_4$, filtered and concentrated. The crude product was purified by flash chromatography using (5% MeOH/CH$_2$Cl$_2$) as a solvent to afford title compound (50 mg, 47% yield). MS m/z: 628 [M+1].

D. N-(3-((5-aminopyrazin-2-yl)methylamino)-4-methylphenyl)-4-((4-ethylpiperazin-1-yl)methyl)-3-(trifluoromethyl)benzamide

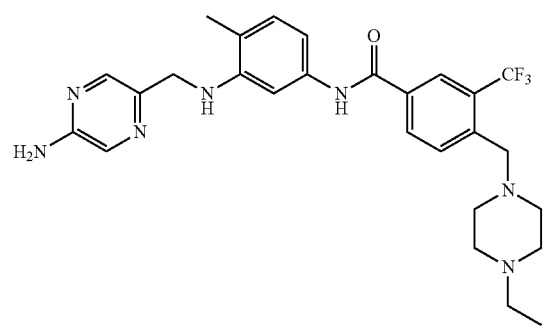

I-1

To a solution tert-butyl 5-((5-(4-((4-ethylpiperazin-1-yl)methyl)-3-(trifluoromethyl)benzamido)-2-methylphenylamino)methyl)pyrazin-2-ylcarbamate (30 mg, 0.05 mmol) in CH$_2$Cl$_2$ (0.3 ml) was added TFA (18 μL, 0.24 mmol). The reaction mixture was stirred for 4 hours at room temperature after which, it was concentrated under reduced pressure. The crude product was purified by Prep HPLC and acetonitrile was removed under reduced pressure. The remained water was freeze-dried to afford TFA salt formed title compound (22 mg, 74% yield). $^1$H NMR (600 MHz, DMSO-d$_6$) δ 10.22 (s, 1H), 8.17 (d, J=2.4 Hz, 1H), 8.01 (d, J=7.8 Hz, 1H), 7.85 (s, 1H), 7.82 (d, J=1.2 Hz, 1H), 7.65 (s, J=9.0 Hz, 1H), 7.14 (dd, J=1.8, 7.8 Hz, 2H), 7.03 (d, J=1.8 Hz, 1H), 6.23 (s, 2H), 5.64 (t, J=6.0 Hz, 1H), 4.32 (d, J=5.4 Hz, 2H), 3.6 (brs, 2H), 3.40-3.25 (brs, 10H), 2.18 (s, 3H), 1.15 (t, J=7.2 Hz, 3H). MS m/z: 528 [M+1].

Additional compounds made by the synthetic route of Example 1 are found in FIGS. 1A to 1E.

Example 2

3-((5-aminopyrazin-2-yl)methylamino)-N,4-dimethylbenzamide

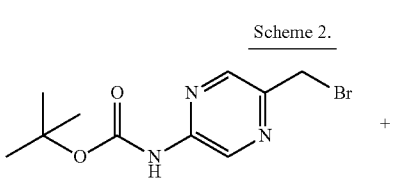

Scheme 2.

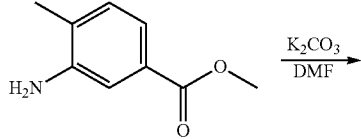

A. Methyl 3-((5-(tert-butoxycarbonylamino)pyrazin-2-yl)methylamino)-4-methylbenzoate Methyl 3-((5-(tert-butoxycarbonylamino)pyrazin-2-yl)methylamino)-4-methylbenzoate (650 mg, 57% yield) was prepared as described for Example 1-C starting from methyl 3-amino-4-methylbenzoate (500 mg, 3.03 mmol). $^1$H NMR (600 MHz, CDCl$_3$) δ 9.26 (s, 1H), 8.25 (s, 1H), 7.52 (s, 1H), 7.38 (d, J=7.2 Hz, 1H), 7.29 (s, 1H), 7.14 (d, J=7.2 Hz, 1H), 4.52 (s, 2H), 3.88 (s, 3H), 2.26 (s, 3H), 1.55 (s, 9H). MS m/z: 373 [M+1].

B. 3-((5-(tert-butoxycarbonylamino)pyrazin-2-yl)methylamino)-4-methylbenzoic acid

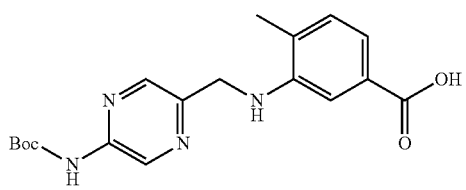 [SMILES: Cc1ccc(C(=O)O)cc1NCc1cnc(NC(=O)OC(C)(C)C)cn1]

Methyl 3-((5-(tert-butoxycarbonylamino)pyrazin-2-yl)methylamino)-4-methylbenzoate (600 mg, 1.61 mmol) in THF (2 mL) and MeOH (2 mL) was added LiOH.H$_2$O (338 mg, 8.06 mmol) in water (2 mL). The reaction mixture was stirred for overnight at room temperature. The organic solvent was removed under reduced pressure and water (4 mL) was added to the reaction mixture. To a reaction mixture was added 1N HCl solution to produce solid. The solid product was filtered and dried with nitrogen gas flow. The title product (460 mg, 79% yield) was used next reaction without further purification. MS m/z: 359 [M+1].

C. tert-butyl 5-((2-methyl-5-(methylcarbamoyl)phenylamino)methyl)pyrazin-2-ylcarbamate

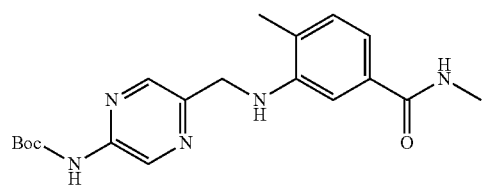 [SMILES: CNC(=O)c1ccc(C)c(NCc2cnc(NC(=O)OC(C)(C)C)cn2)c1]

To a solution of 3-((5-(tert-butoxycarbonylamino)pyrazin-2-yl)methylamino)-4-methylbenzoic acid (30 mg, 0.08 mmol) in DMF (1 mL) were added HATU (95 mg, 0.25 mmol), DIEA (74 □L, 0.42 mmol) and methylamine hydrochloride (9 mg, 0.13 mmol). The reaction mixture was stirred for overnight at room temperature after which, it was partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product (29 mg, 93% yield) was used without further purification. MS m/z: 372 [M+1].

D. 3-((5-aminopyrazin-2-yl)methylamino)-N,4-dimethylbenzamide

II-1

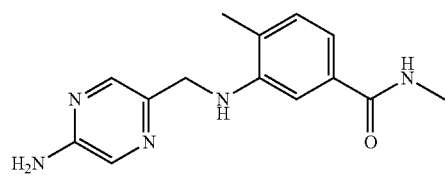

3-((5-aminopyrazin-2-yl)methylamino)-N,4-dimethylbenzamide (21 mg, 70% yield) was prepared as described for Example 1-D starting from tert-butyl 5-((2-methyl-5-(methylcarbamoyl)phenylamino)methyl)pyrazin-2-ylcarbamate (29 mg, 0.08 mmol). $^1$H NMR (600 MHz, DMSO-d$_6$) δ 8.10 (s, 1H), 7.81 (s, 2H), 7.01-6.90 (m, 3H), 6.21 (s, 2H), 5.40 (s, 1H), 4.29 (s, 2H), 2.71 (s, 3H), 2.14 (s, 3H). MS m/z: 272 [M+1].

Additional compounds made by the synthetic route of Example 2 are found in FIGS. 2A to 2B.

Example 3

N-(3-((5-acetamidopyrazin-2-yl)methylamino)-4-methylphenyl)-4-((4-ethylpiperazin-1-yl)methyl)-3-(trifluoromethyl)benzamide

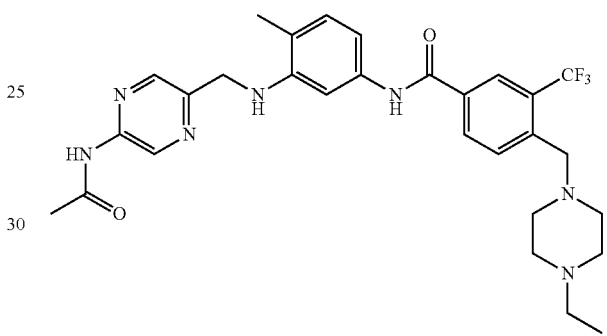

Scheme 3.

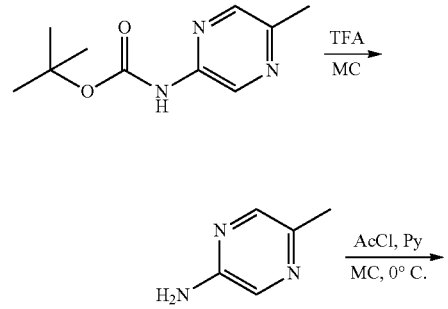

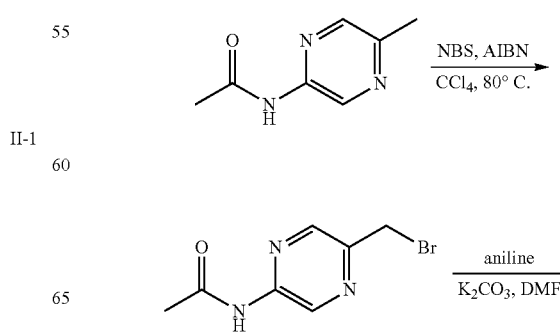

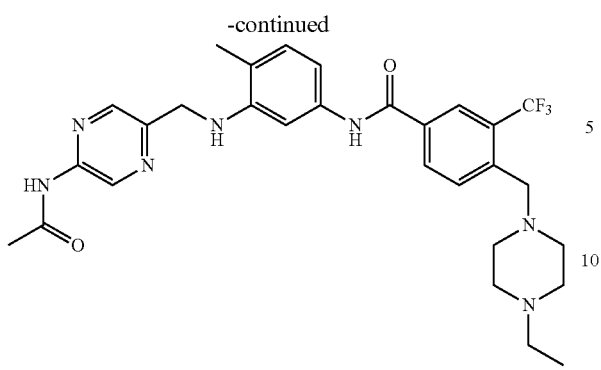

A. 5-methylpyrazin-2-amine

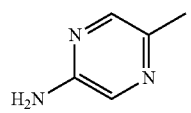

To a solution tert-butyl 5-methylpyrazin-2-ylcarbamate (1.5 g, 7.17 mmol) in $CH_2Cl_2$ (20 ml) was added TFA (2.6 mL, 35.86 mmol). The reaction mixture was stirred for 4 hours at room temperature after which, it was concentrated under reduced pressure. The reaction mixture was diluted with $CH_2Cl_2$ and neutralized with sat.$NaHCO_3$ solution. The organic layer was separated and the aqueous layer was extracted with $CH_2Cl_2$. The combined organic extracts were washed with brine, dried over $MgSO_4$, celite filtered and concentrated under reduced pressure. The crude product was purified by flash chromatography using (30% to 50% Ethyl acetate/Hexane) as a solvent to afford title compound (580 mg, 74% yield). MS m/z: 110 [M+1].

B. N-(5-methylpyrazin-2-yl)acetamide

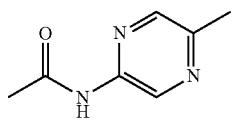

To a solution of 5-methylpyrazin-2-amine (300 mg, 2.75 mmol) in dried THF (9 mL) were added acetyl chloride (0.21 mL, 2.89 mmol) and TEA (0.75 mL, 5.50 mmol). The reaction mixture was stirred for 3 hours after which, it was partitioned between ethyl acetate and water. The organic layer was separated and the aqueous layer was extracted with ethyl acetate. The combined organic extracts were washed with brine, dried over $MgSO_4$, celite filtered and concentrated under reduced pressure. The crude product was purified by flash chromatography using (10% to 30% Ethyl acetate/Hexane) as a solvent to afford title compound (360 mg, 86% yield). MS m/z: 152 [M+1].

C. N-(5-(bromomethyl)pyrazin-2-yl)acetamide

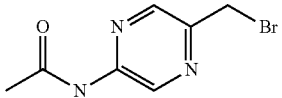

N-(5-(bromomethyl)pyrazin-2-yl)acetamide (420 mg, 51% yield) was prepared as described for Example 1-B starting from N-(5-methylpyrazin-2-yl)acetamide (330 mg, 2.18 mmol). MS m/z: 231 [M+1].

D. N-(3-((5-acetamidopyrazin-2-yl)methylamino)-4-methylphenyl)-4-((4-ethylpiperazin-1-yl)methyl)-3-(trifluoromethyl)benzamide

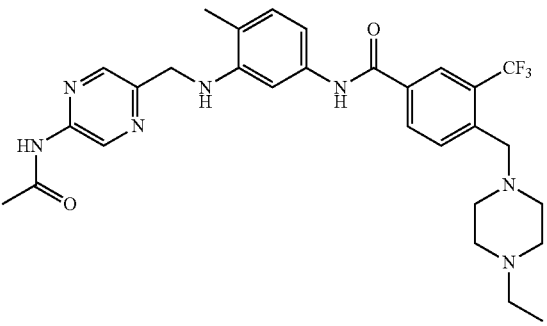 [SMILES: CCN1CCN(Cc2ccc(C(=O)Nc3ccc(C)c(NCc4cnc(NC(C)=O)cn4)c3)cc2C(F)(F)F)CC1]

III-1

To a solution N-(3-amino-4-methylphenyl)-4-((4-ethylpiperazin-1-yl)methyl)-3-(trifluoromethyl)benzamide (50 mg, 0.12 mmol) in acetonitrile (0.5 mL) were added $K_2CO_3$ (49 mg, 0.36 mmol) and N-(5-(bromomethyl)pyrazin-2-yl)acetamide (44 mg, 0.12 mmol). The reaction mixture was filtered with celite and concentrated under reduced pressure. The crude product was purified by Prep HPLC and acetonitrile was removed under reduced pressure. The remained water was freeze-dried to afford TFA salt formed title compound (40 mg, 49% yield). $^1$H NMR (600 MHz, $CD_3OD$) δ 9.49 (d, J=1.2 Hz, 1H), 8.53 (d, J=1.2 Hz, 1H), 8.12 (d, J=1.8 Hz, 1H), 7.94 (dd, J=1.8, 8.4 Hz, 1H), 7.74 (d, J=8.4 Hz, 1H), 7.24 (d, J=1.8 Hz, 1H), 7.17 (dd, J=1.8, 7.8 Hz, 1H), 7.12 (d, J=7.8 Hz, 1H), 4.72 (s, 2H), 3.84 (s, 2H), 3.68-3.64 (m, 2H), 3.55-3.46 (m, 4H), 3.02-2.99 (m, 2H), 2.90-2.87 (m, 2H), 2.21 (s, 6H), 1.49 (t, 7.2 Hz, 3H). MS m/z: 570 [M+1].

Additional compounds made by the synthetic route of Example 3 are found in FIGS. 3A to 3E.
Example 4
(E)-N-(3-(2-(5-aminopyrazin-2-yl)vinyl)-4-methylphenyl)-4-((4-methylpiperazin-1-yl)methyl)-3-(trifluoromethyl)benzamide
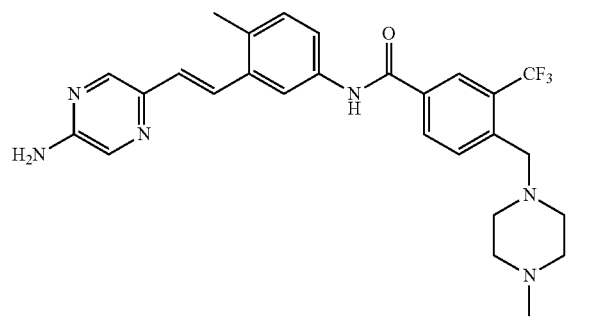 [SMILES: Cc1ccc(NC(=O)c2ccc(CN3CCN(C)CC3)c(C(F)(F)F)c2)cc1/C=C/c1cnc(N)cn1]
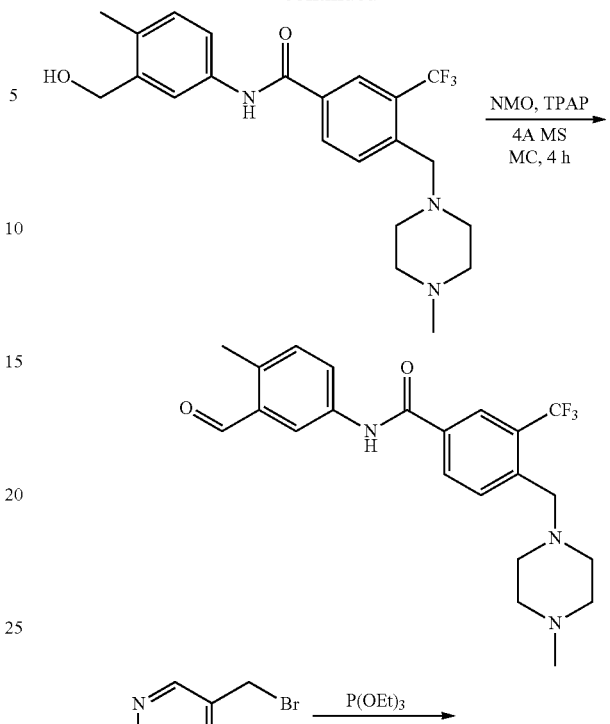
Scheme 4.
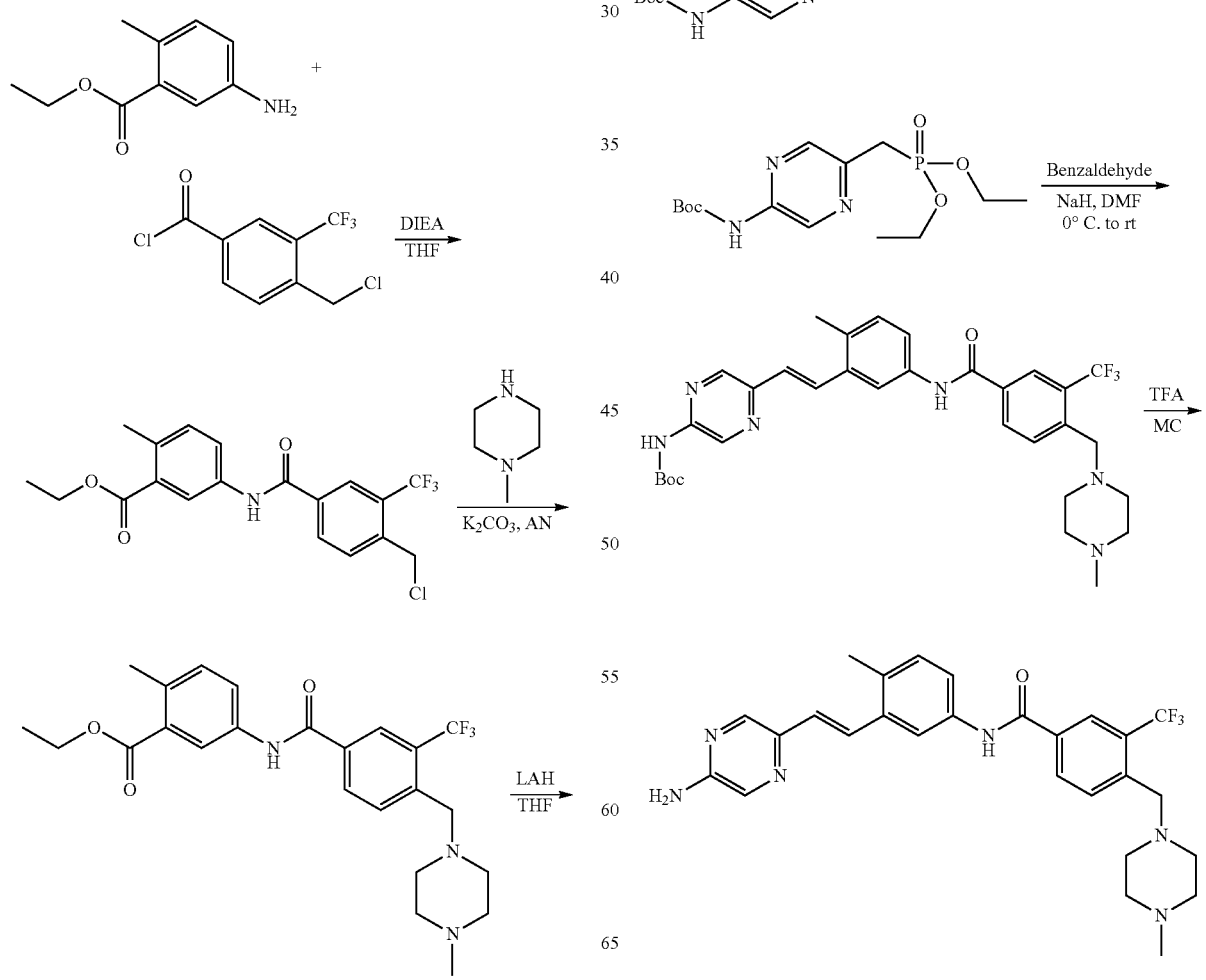

A. Ethyl 2-methyl-5-(4-((4-methylpiperazin-1-yl)methyl)-3-(trifluoromethyl)benzamido)benzoate

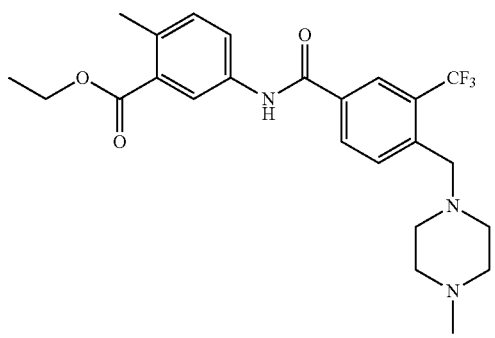 [SMILES: CCOC(=O)c1cc(NC(=O)c2ccc(CN3CCN(C)CC3)c(C(F)(F)F)c2)ccc1C]

To a solution of ethyl 5-amino-2-methylbenzoate (500 mg, 2.79 mmol) and TEA (0.78 mL, 5.58 mmol) in dried THF (9 mL) was added 4-(chloromethyl)-3-(trifluoromethyl)benzoyl chloride (714 mg, 2.79 mmol). The reaction mixture was stirred for 5 hours at room temperature after which, it was concentrated under reduced pressure. To a solution of the reaction mixture in acetonitrile (10 mL) were added methyl piperazine (558 mg, 5.58 mmol) and $K_2CO_3$ (1.1 g, 8.38 mmol). The reaction mixture was stirred for 8 hours at room temperature. The reaction mixture was partitioned between ethyl acetate and water. The organic layer was separated and the aqueous layer was extracted with ethyl acetate. The combined organic extracts were washed with brine, dried over $MgSO_4$, celite filtered and concentrated under reduced pressure. The crude product was purified by flash chromatography using (3% to 7% Methanol/$CH_2Cl_2$) as a solvent to afford title compound (820 mg, 63% yield). MS m/z: 464 [M+1].

B. N-(3-(hydroxymethyl)-4-methylphenyl)-4-((4-methylpiperazin-1-yl)methyl)-3-(trifluoromethyl)benzamide

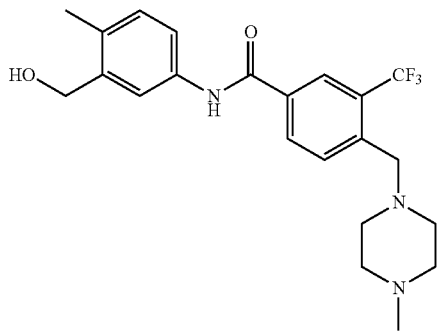 [SMILES: Cc1ccc(NC(=O)c2ccc(CN3CCN(C)CC3)c(C(F)(F)F)c2)cc1CO]

To a solution Ethyl 2-methyl-5-(4-((4-methylpiperazin-1-yl)methyl)-3-(trifluoromethyl)benzamido)benzoate (300 mg, 0.65 mmol) in dried THF (2.2 mL) was added Lithium aluminium hydride 2.0M THF solution (0.48 mL, 0.98 mmol) at 0° C. The reaction mixture was stirred for 2 hours at room temperature. When the reaction was completed, the reaction mixture was diluted with ethyl ether (2.0 mL) and added water very slowly to decompose the excess of the reagent. To a reaction mixture was added $MgSO_4$, celite filtered and concentrated under reduced pressure. The title compound (230 mg, 84% yield) was used next step without further purification. MS m/z: 422 [M+1].

C. N-(3-formyl-4-methylphenyl)-4-((4-methylpiperazin-1-yl)methyl)-3-(trifluoromethyl)benzamide

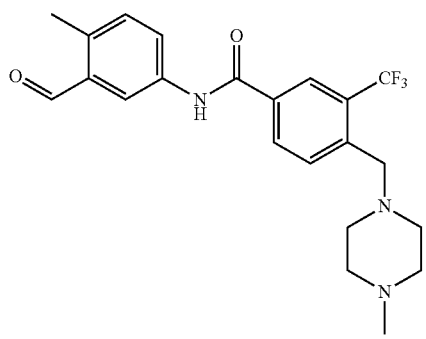 [SMILES: Cc1ccc(NC(=O)c2ccc(CN3CCN(C)CC3)c(C(F)(F)F)c2)cc1C=O]

To a stirred solution of N-(3-(hydroxymethyl)-4-methylphenyl)-4-((4-methylpiperazin-1-yl)methyl)-3-(trifluoromethyl)benzamide (200 mg, 0.47 mmol) in $CH_2Cl_2$ (2 mL) was added freshly dried 4 Å MS and NMO (83 mg, 0.71 mmol). The mixture was stirred for 10 min before TPAP (17 mg, 0.05 mmol) was added, and the resulting reaction mixture was stirred 12 hours at room temperature. The reaction mixture was filtered through celite, concentrated under reduced pressure, and purified by flash column chromatography (3% to 7% MeOH/$CH_2Cl_2$) to afford title product (175 g, 88% yield). MS m/z: 420 [M+1].

D. tert-butyl 5-((diethoxyphosphoryl)methyl)pyrazin-2-ylcarbamate

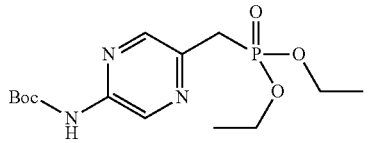 [SMILES: CCOP(=O)(Cc1cnc(NC(=O)OC(C)(C)C)cn1)OCC]

tert-butyl 5-(bromomethyl)pyrazin-2-ylcarbamate (2.5 g, 8.71 mmol) and triethylphosphite (1.8 ml, 10.45 mmol) were placed in a 25 mL round bottom flask. A distillation apparatus was attached to collect the poisonous ethyl bromide formed during the reaction. The reaction mixture was heated to 140° C. for 30 minutes and then cooled to room temperature. The reaction mixture was purified by flash column chromatography (10% to 30% Ethyl acetate/Hexane) to afford title product (1.8 g, 60% yield). $^1$H NMR (600 MHz, $CDCl_3$) δ 9.19 (s, 1H), 8.22 (t, J=1.8 Hz, 1H), 7.37 (s, 1H), 4.12-4.07 (m, 4H), 3.38 (s, 1H), 3.34 (s, 1H), 1.54 (s, 9H), 1.29 (t, J=7.2 Hz, 6H). MS m/z: 346 [M+1].

E. (E)-tert-butyl 5-(2-methyl-5-(4-((4-methylpiperazin-1-yl)methyl)-3-(trifluoromethyl)benzamido)styryl)pyrazin-2-ylcarbamate

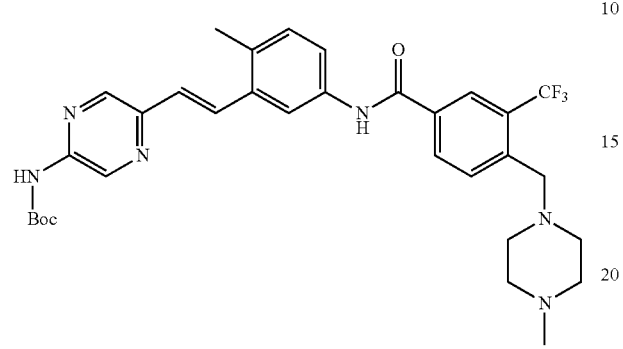

tert-butyl 5-((diethoxyphosphoryl)methyl)pyrazin-2-ylcarbamate (35 mg, 0.10 mmol) in dried DMF (0.5 mL) was added NaH (5 mg, 0.12 mmol) at 0° C. After 20 minutes, a solution N-(3-formyl-4-methylphenyl)-4-((4-methylpiperazin-1-yl)methyl)-3-(trifluoromethyl)benzamide (44 mg, 0.10 mmol) in dried DMF (0.5 mL) was added slowly into the reaction mixture. The reaction mixture was stirred overnight at room temperature and quenched by adding water. The reaction mixture was partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product was purified by flash chromatography using (3% to 7% MeOH/CH$_2$Cl$_2$) as a solvent to afford title compound (40 mg, 64% yield). MS m/z: 611 [M+1].

F. (E)-N-(3-(2-(5-aminopyrazin-2-yl)vinyl)-4-methylphenyl)-4-((4-methylpiperazin-1-yl)methyl)-3-(trifluoromethyl)benzamide

IV-1

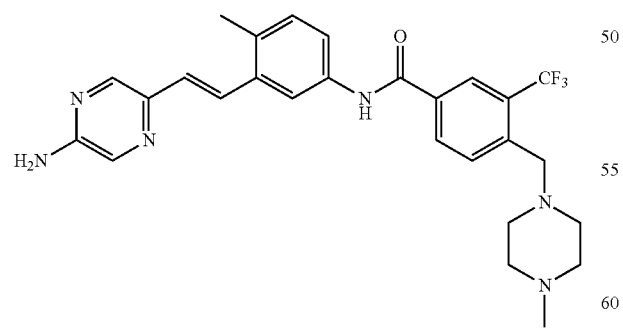

(E)-N-(3-(2-(5-aminopyrazin-2-yl)vinyl)-4-methylphenyl)-4-((4-methylpiperazin-1-yl)methyl)-3-(trifluoromethyl)benzamide (25 mg, 81% yield) was prepared as described for Example 1-D starting from (E)-tert-butyl 5-(2-methyl-5-(4-((4-methylpiperazin-1-yl)methyl)-3-(trifluoromethyl)benzamido)styryl)pyrazin-2-ylcarbamate (30 mg, 0.05 mmol). MS m/z: 511 [M+1].

Figure 4C:
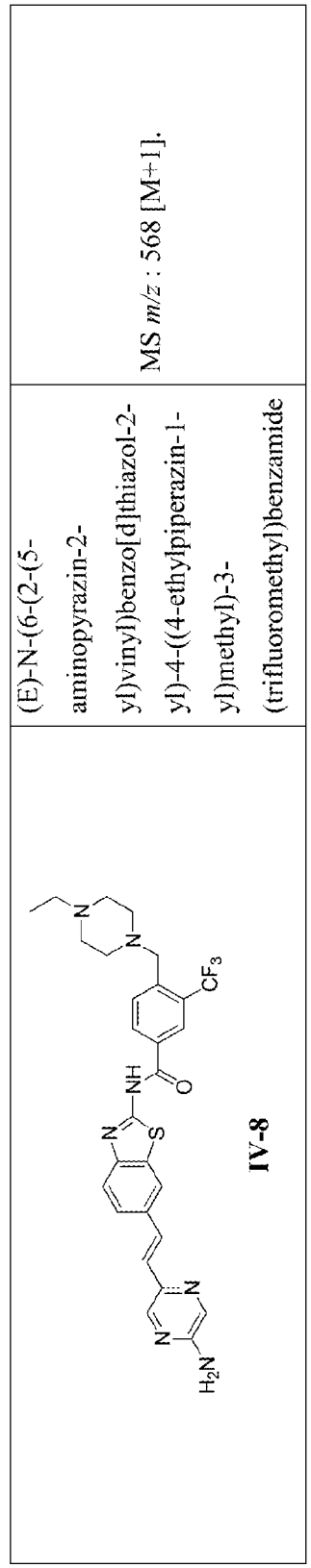
Figure 5E:
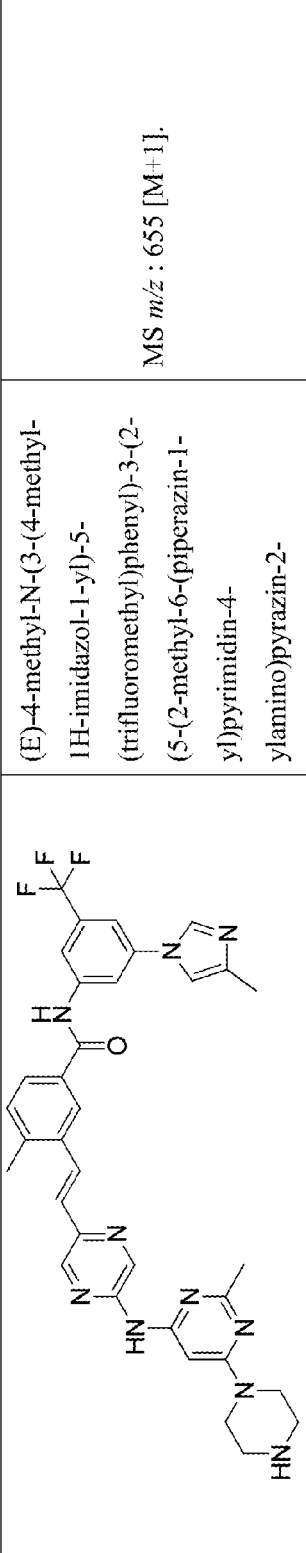
Figure 7B:
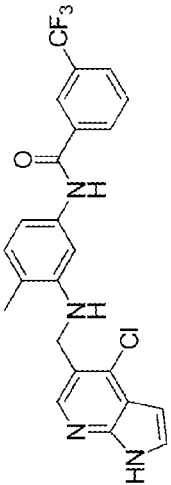
Figure 12C:
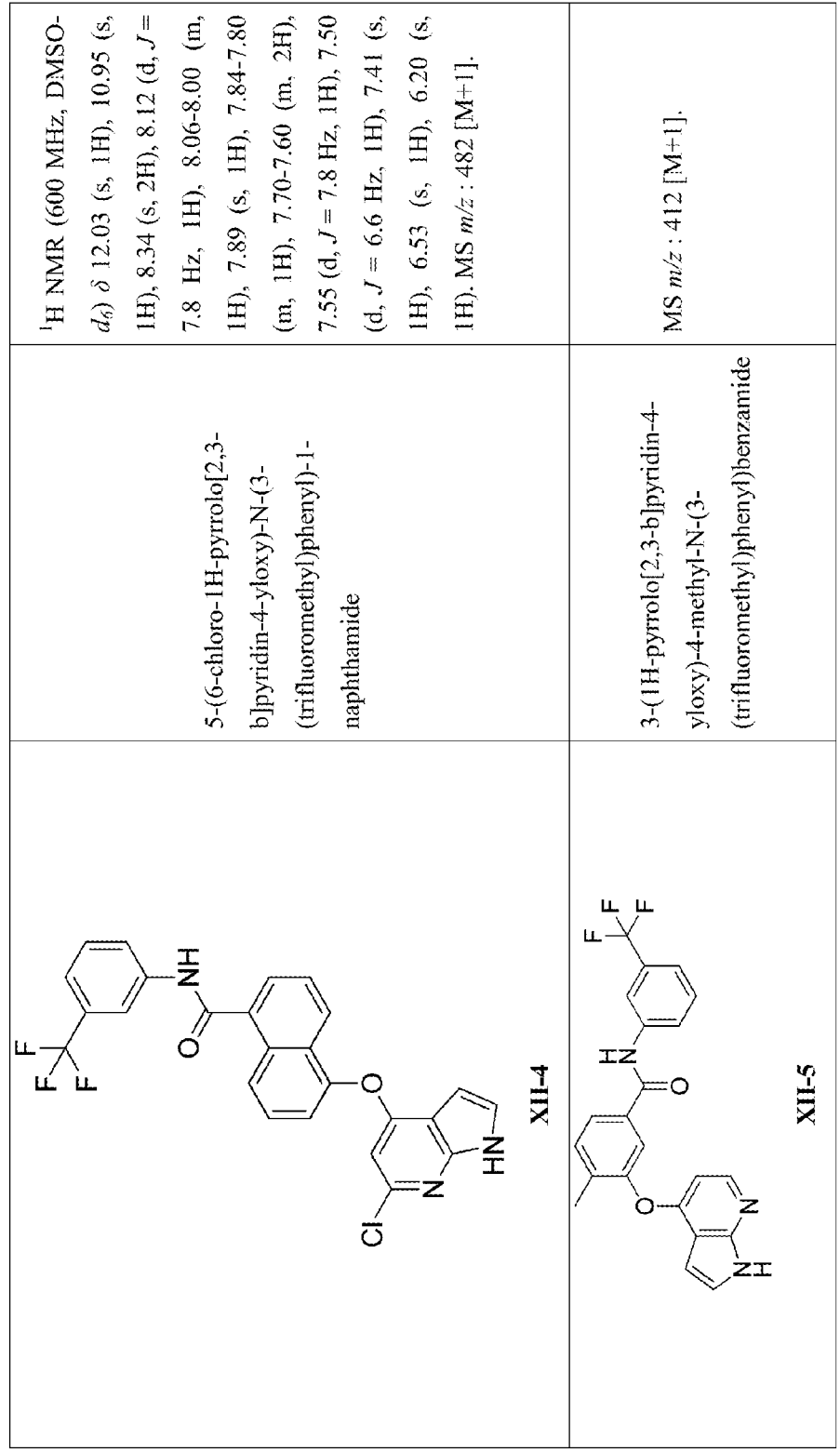
Figure 18B:
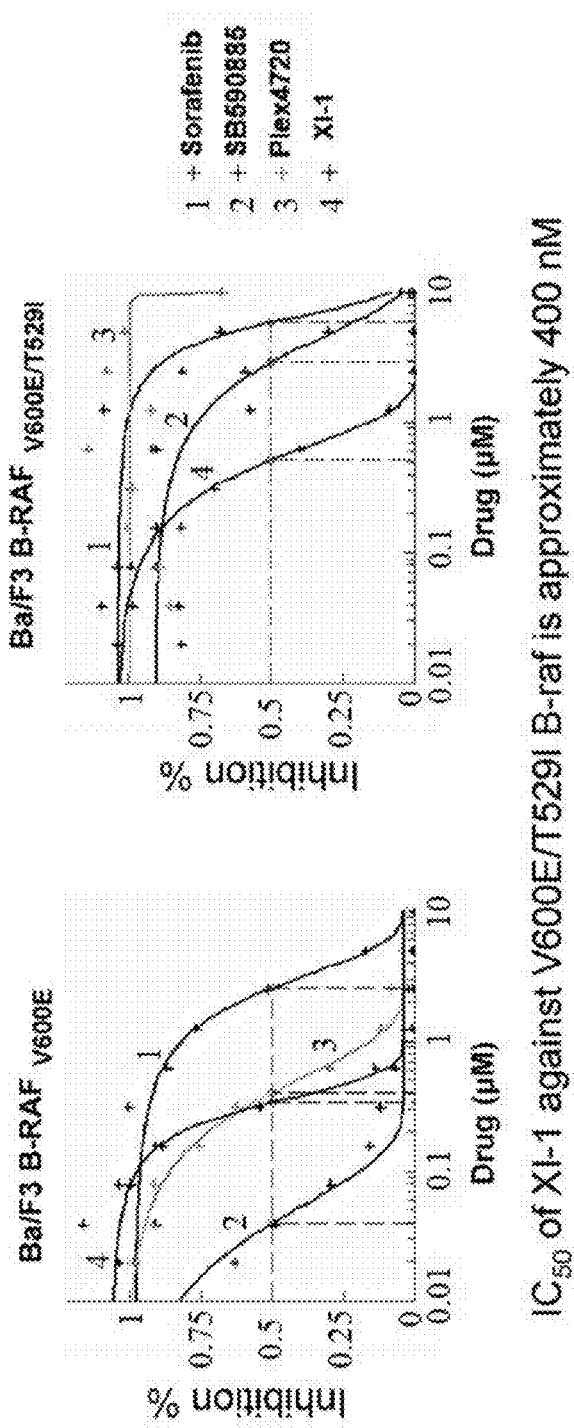

Additional compounds made by the synthetic route of Example 4 are found in FIGS. 4A to 4C.

Example 5

(E)-3-(2-(5-(4-(piperazin-1-ylsulfonyl)phenylamino)pyrazin-2-yl)vinyl)phenol

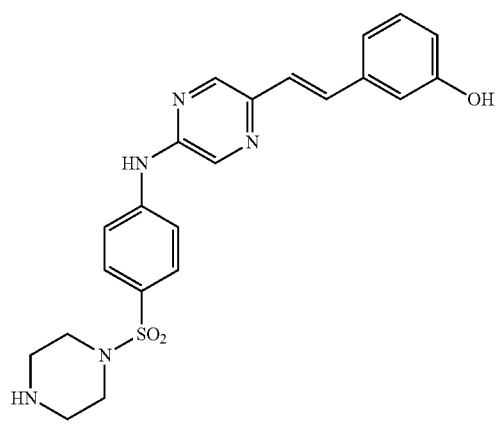 [SMILES: O=S(=O)(c1ccc(Nc2cnc(/C=C/c3cccc(O)c3)cn2)cc1)N1CCNCC1]

Scheme 5.

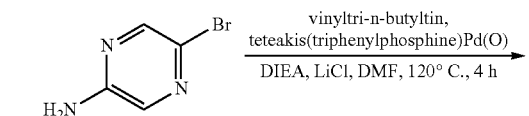

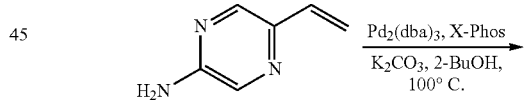

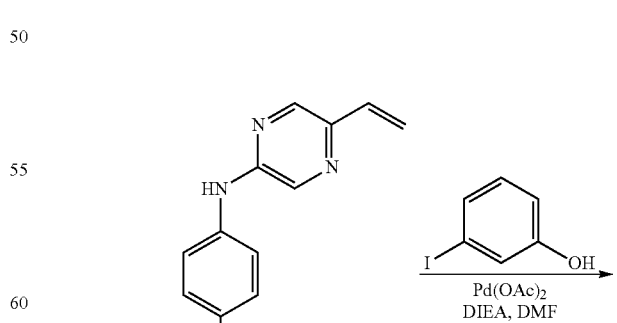

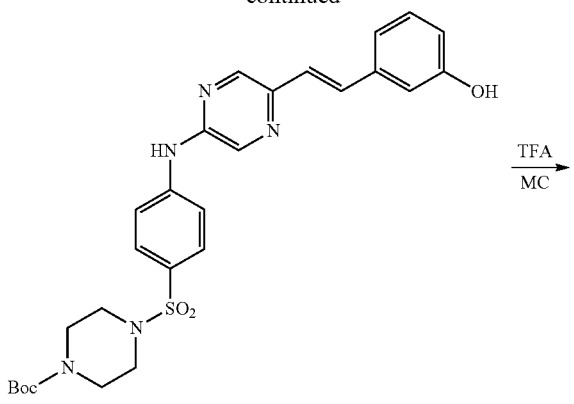

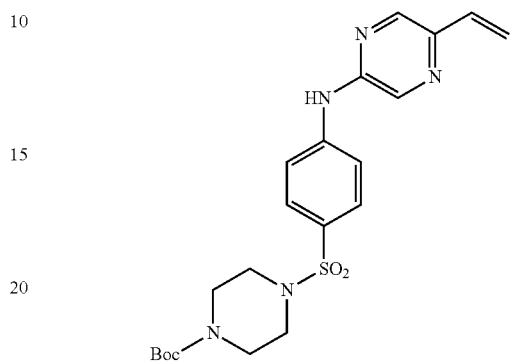

B. tert-butyl 4-(4-(5-vinylpyrazin-2-ylamino)phenyl-sulfonyl)piperazine-1-carboxylate To a solution of 5-vinylpyrazin-2-amine (150 mg, 1.24 mmol) in 2-buOH (4 mL) were added $K_2CO_3$ (512 mg, 3.71 mmol), and tert-butyl 4-(4-aminophenylsulfonyl)piperazine-1-carboxylate (421 mg, 1.24 mmol). The reaction mixture was degassed for 10 minutes. To a mixture were added $Pd_2(dba)_3$ (76 mg, 0.07 mmol) and X-phos (53 mg, 0.11 mmol). The reaction mixture was heated to 100° C. for 6 hours after which, it was filtered with a pad of celite and partitioned between ethyl acetate and water. The organic layer was separated and the aqueous layer was extracted with ethyl acetate. The combined organic extracts were washed with brine, dried over $MgSO_4$, celite filtered and concentrated under reduced pressure. The crude product was purified by flash chromatography using (20% to 30% Ethyl acetate/Hexane) as a solvent to afford title compound (360 mg, 65% yield). MS m/z: 446 [M+1].

C. (E)-tert-butyl 4-(4-(5-(3-hydroxystyryl)pyrazin-2-ylamino)phenylsulfonyl)piperazine-1-carboxylate A. 5-vinylpyrazin-2-amine

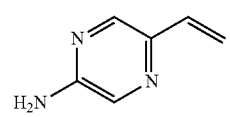

To a mixture of 5-bromopyrazin-2-amine (1.0 g, 5.78 mmol) and vinyltri-n-butyltin (2.01 g, 6.36 mmol) in DMF (19 mL) were added LiCl (269 mg, 6.36 mmol) and DIEA (1.1 mL, 6.36 mmol). After degassing for 20 minutes, Pd(PPh$_3$)$_4$ (400 mg, 0.35 mmol) was added to the reaction mixture. And then the mixture was refluxed for 4 hours under Ar atmosphere. The reaction mixture was cooled to room temperature and stirred with a 10% aqueous solution of potassium fluoride for 1 hour. The resulting solution was filtered through a pad of celite and washed with ethyl acetated. The aqueous layer was separated and extracted with ethyl acetate. The combined organic layer was dried over MgSO$_4$ and concentrated under reduced pressure. The crude product was purified by flash column chromatography (30% to 50% Ethyl acetate/Hexane) to afford title product (540 mg, 77% yield). MS m/z: 122 [M+1].

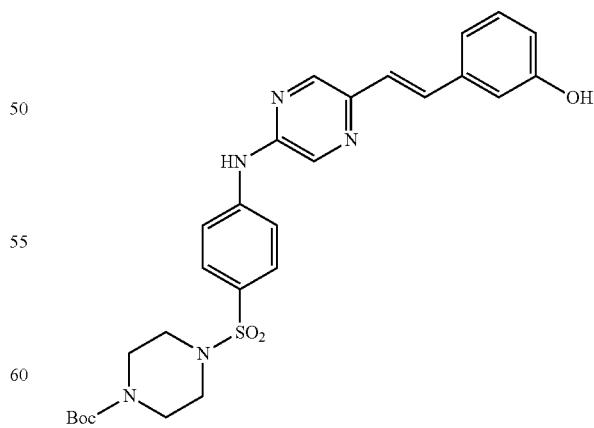

A mixture of tert-butyl 4-(4-(5-vinylpyrazin-2-ylamino)phenylsulfonyl)piperazine-1-carboxylate (40 mg, 0.09 mmol), 3-iodophenol (19 mg, 0.09 mmol), Pd(OAc)$_2$ (1.2 mg, 0.005 mmol), tri-p-tolylphosphine (2.5 mg, 0.008 mmol), and DIEA (31 µL, 0.18 mmol) in DMF (3 ml) was heated at 120° C. for 18 h after which, it was filtered with a pad of celite and partitioned between ethyl acetate and water. The organic layer was separated and the aqueous layer was extracted with ethyl acetate. The combined organic extracts were washed with brine, dried over $MgSO_4$, celite filtered and concentrated under reduced pressure. The crude product was purified by flash chromatography using (20% to 40% Ethyl acetate/Hexane) as a solvent to afford title compound (38 mg, 78% yield). MS m/z: 538 [M+1].

D. (E)-3-(2-(5-(4-(piperazin-1-ylsulfonyl)phenylamino)pyrazin-2-yl)vinyl)phenol

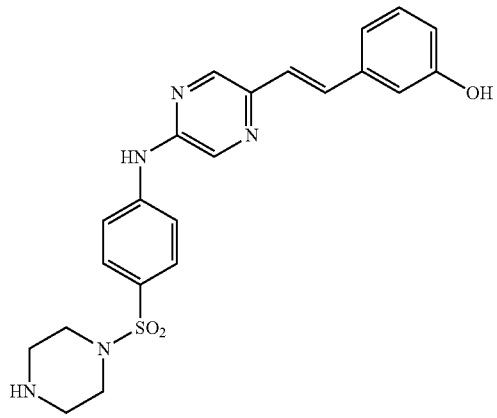 [SMILES: O=S(=O)(c1ccc(Nc2cnc(/C=C/c3cccc(O)c3)cn2)cc1)N1CCNCC1]

(E)-3-(2-(5-(4-(piperazin-1-ylsulfonyl)phenylamino)pyrazin-2-yl)vinyl)phenol (26 mg, 84% yield) was prepared as described for Example 1-D starting from (E)-tert-butyl 4-(4-(5-(3-hydroxystyryl)pyrazin-2-ylamino)phenylsulfonyl)piperazine-1-carboxylate (30 mg, 0.06 mmol). MS m/z: 438 [M+1].

Additional compounds made by the synthetic route of Example 5 are found in FIGS. 5A to 5G.

Example 6

4-chloro-N-(5-(4-((4-ethylpiperazin-1-yl)methyl)-3-(trifluoromethyl)benzamido)-2-methylphenyl)-1H-pyrrolo[2,3-b]pyridine-5-carboxamide

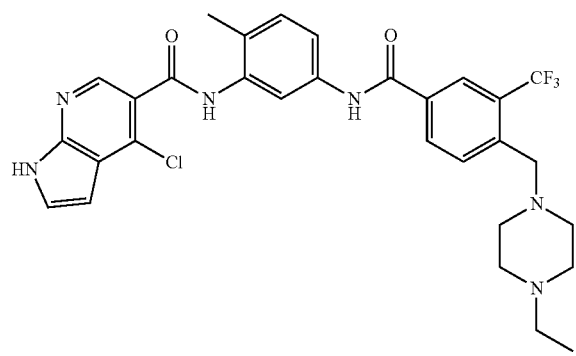

Scheme 6.

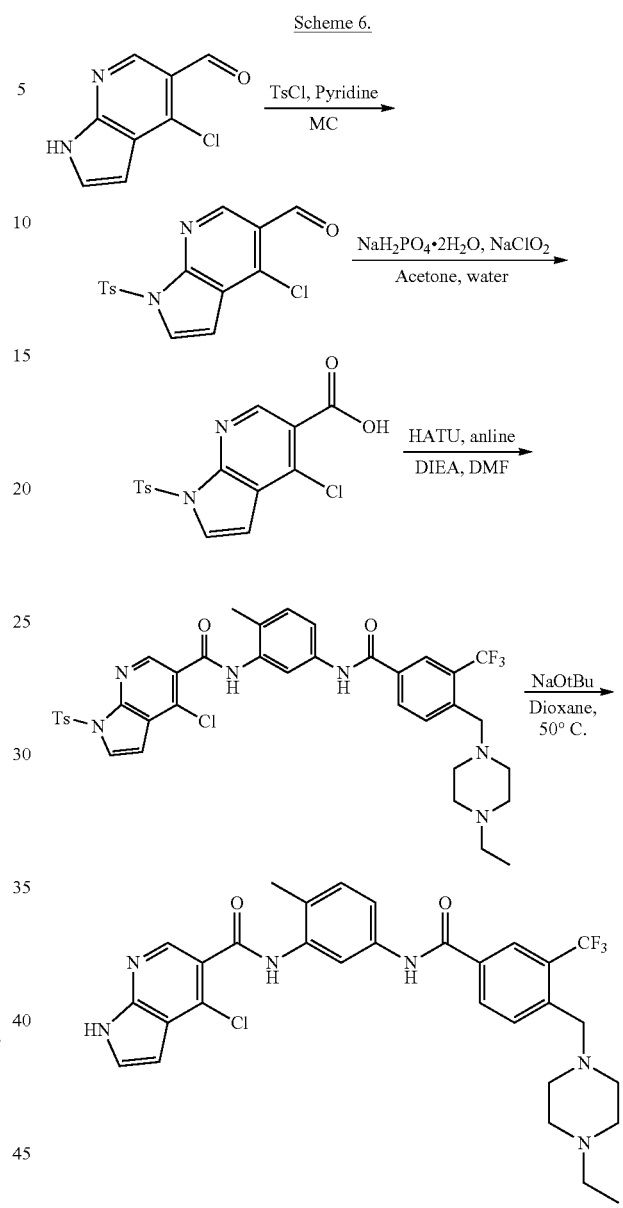

A. 4-chloro-1-tosyl-1H-pyrrolo[2,3-b]pyridine-5-carbaldehyde

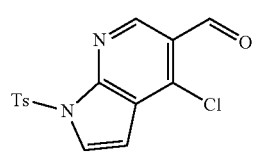 [SMILES: Cc1ccc(S(=O)(=O)n2ccc3c(Cl)c(C=O)cnc32)cc1]

To a solution 4-chloro-1H-pyrrolo[2,3-b]pyridine-5-carbaldehyde (500 mg, 2.78 mmol) in MC (9 mL) were added TsCl (556 mg, 2.91 mmol) and DMAP (509 mg, 4.17 mmol). The reaction mixture stirred for 8 hours at room temperature. The produced precipitated was filtered, washed with water and dried with nitrogen gas flow. The title product (810 mg, 87% yield) was used without further purification. MS m/z: 335 [M+1].

B. 4-chloro-1-tosyl-1H-pyrrolo[2,3-b]pyridine-5-carboxylic acid

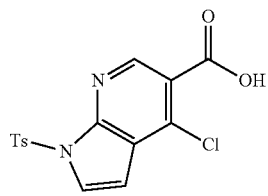 [SMILES: Cc1ccc(S(=O)(=O)n2ccc3c(Cl)c(C(=O)O)cnc32)cc1]

To a stirred solution of NaH$_2$PO$_4$·2H$_2$O (513 mg, 3.3 mmol) in water (3 ml), was added a solution of 4-chloro-1-tosyl-1H-pyrrolo[2,3-b]pyridine-5-carbaldehyde (500 mg, 1.50 mmol) in acetone (6 ml) at 0° C. A solution of NaClO$_2$ (541 mg, 5.98 mmol) in water (3 ml) was added to the reaction mixture at 0° C. and the reaction mixture was warmed to room temperature spontaneously. After 2 hours, 1N HCl solution was added to reach pH=5. The produced solid was filtered and dried with nitrogen gas flow. The title product (440 mg, 84% yield) was used next reaction without further purification. MS m/z: 351 [M+1].

C. 4-chloro-N-(5-(4-((4-ethylpiperazin-1-yl)methyl)-3-(trifluoromethyl)benzamido)-2-methylphenyl)-1-tosyl-1H-pyrrolo[2,3-b]pyridine-5-carboxamide

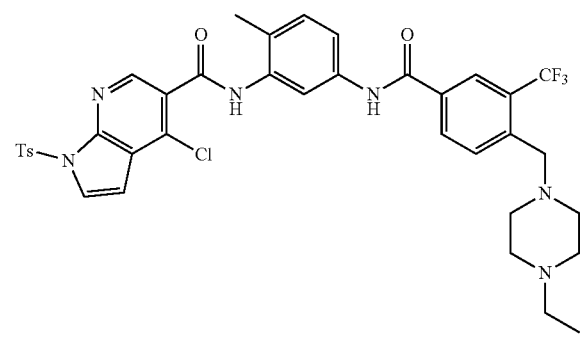 [SMILES: CCN1CCN(Cc2ccc(C(=O)Nc3ccc(C)c(NC(=O)c4cnc5c(ccn5S(=O)(=O)c5ccc(C)cc5)c4Cl)c3)cc2C(F)(F)F)CC1]

To a solution of 4-chloro-1-tosyl-1H-pyrrolo[2,3-b]pyridine-5-carboxylic acid (50 mg, 0.14 mmol) in DMF (1 mL) were added HATU (162 mg, 0.43 mmol), DIEA (0.12 mL, 0.71 mmol) and N-(3-amino-4-methylphenyl)-4-((4-ethylpiperazin-1-yl)methyl)-3-(trifluoromethyl)benzamide (60 mg, 0.14 mmol). The reaction mixture was stirred for overnight at room temperature after which, it was poured to water and the produced solid was filtered. The crude solid was dried with nitrogen gas flow. The title compound (85 mg, 0.11 mmol) was used next reaction without further purification. MS m/z: 753 [M+1].

D. 4-chloro-N-(5-(4-((4-ethylpiperazin-1-yl)methyl)-3-(trifluoromethyl)benzamido)-2-methylphenyl)-1H-pyrrolo[2,3-b]pyridine-5-carboxamide

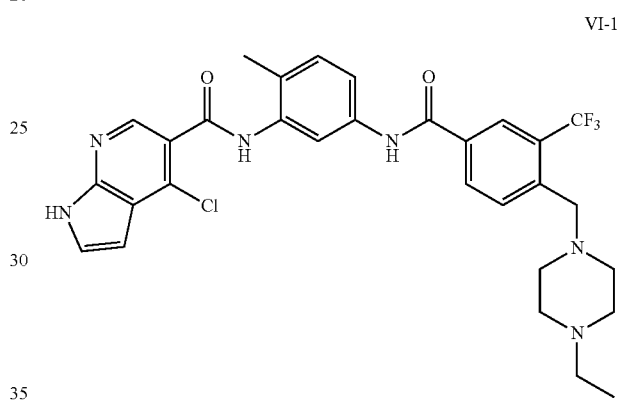

VI-1

To a solution of 4-chloro-N-(5-(4-((4-ethylpiperazin-1-yl)methyl)-3-(trifluoromethyl)benzamido)-2-methylphenyl)-1-tosyl-1H-pyrrolo[2,3-b]pyridine-5-carboxamide (40 mg, 0.053 mmol) in dioxane (1 mL) was added NaOt-Bu (25 mg, 0.27 mmol). The reaction mixture was stirred for 6 hours at 50° C. after which, it was filtered with a pad of celite and partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product was purified by Prep HPLC and acetonitrile was removed under reduced pressure. The remained water was freeze-dried to afford TFA salt formed title compound (29 mg, 76% yield). $^1$H NMR (600 MHz, DMSO-d$_6$) δ 11.89 (s, 1H), 10.21 (s, 1H), 9.33 (brs, 1H), 8.13 (s, 1H), 8.10 (s, 1H), 7.96 (d, J=7.8 Hz, 1H), 7.60 (d, J=8.4 Hz, 1H), 7.50 (t, J=3.0 Hz, 1H), 7.12 (d, J=7.2 Hz, 1H), 7.10 (d, J=7.8 Hz, 1H), 6.98 (s, 1H), 6.43 (s, 1H), 4.55 (s, 2H), 3.65-3.55 (m, 2H), 3.10-3.02 (m, 2H), 2.95-2.80 (m, 4H), 2.35-2.30 (m, 2H), 2.17 (s, 3H), 1.14 (t, J=7.2 Hz, 3H). MS m/z: 599 [M+1].

Additional compounds made by the synthetic route of Example 6 are found in FIGS. 6A to 6B.

Example 7

3-((4-chloro-1H-pyrrolo[2,3-b]pyridin-5-yl)methylamino)-4-methyl-N-(3-(trifluoromethyl)phenyl)benzamide

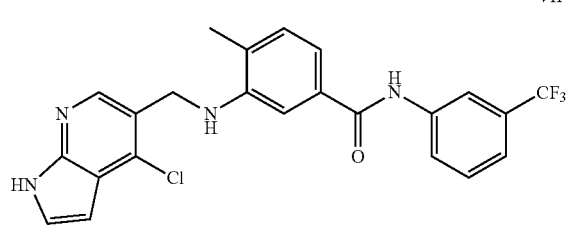

VII-1

Scheme 7.

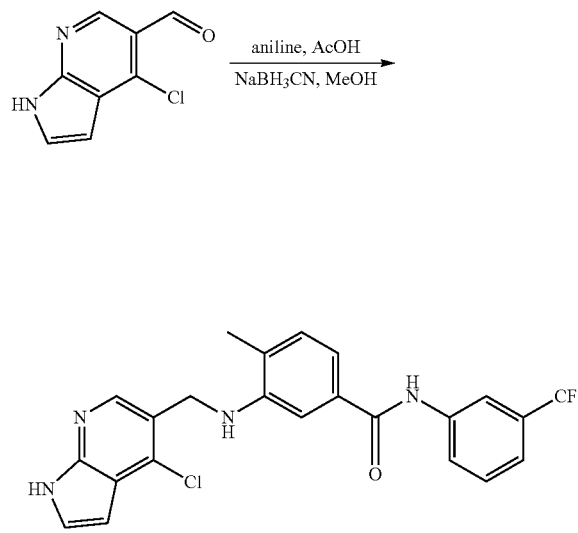

To a solution of 4-chloro-1H-pyrrolo[2,3-b]pyridine-5-carbaldehyde (30 mg, 0.17 mmol) in MeOH (1 mL) were added NaBH$_3$CN (52 mg, 0.83 mmol) and AcOH (29 μL, 0.50 mmol). The reaction mixture was stirred overnight at room temperature. The organic solvent was removed under reduced pressure. The reaction mixture was neutralized with sat. NaHCO3 and the aqueous layer was extracted with ethyl acetate. The organic extracts were washed with brine, dried over MgSO$_4$, celite filtered and concentrated under reduced pressure. The crude product was purified by Prep HPLC and acetonitrile was removed under reduced pressure. The remained water was freeze-dried to afford TFA salt formed title compound (42 mg, 44% yield). $^1$H NMR (600 MHz, DMSO-d$_6$) δ 11.91 (s, 1H), 10.25 (s, 1H), 8.18 (d, J=12.0 Hz, 2H), 7.97 (d, J=7.8 Hz, 1H), 7.52-7.50 (m, 2H), 7.36 (d, J=6.6 Hz, 1H), 7.18 (d, J=7.8 Hz, 1H), 7.13 (d, J=7.8 Hz, 1H), 7.04 (s, 1H), 6.47 (s, 1H), 4.60 (d, J=4.8 Hz, 2H), 3.15 (d, J=4.2 Hz, 1H), 2.22 (s, 3H). MS m/z: 459 [M+1].

Additional compounds made by the synthetic route of Example 7 are found in FIGS. 7A to 7D.

Example 8

N-(3-((1H-pyrrolo[2,3-b]pyridin-5-yl)methylamino)-4-methylphenyl)-4-((4-methylpiperazin-1-yl)methyl)-3-(trifluoromethyl)benzamide

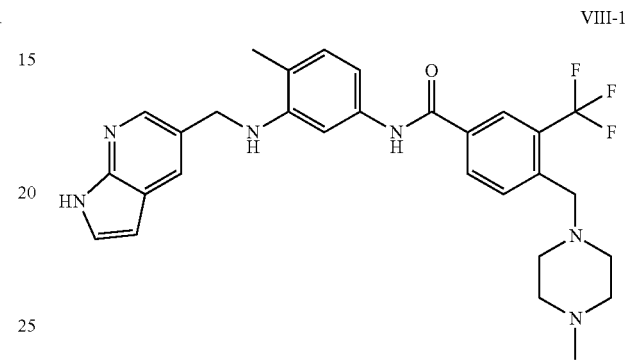

VIII-1

Scheme 8.

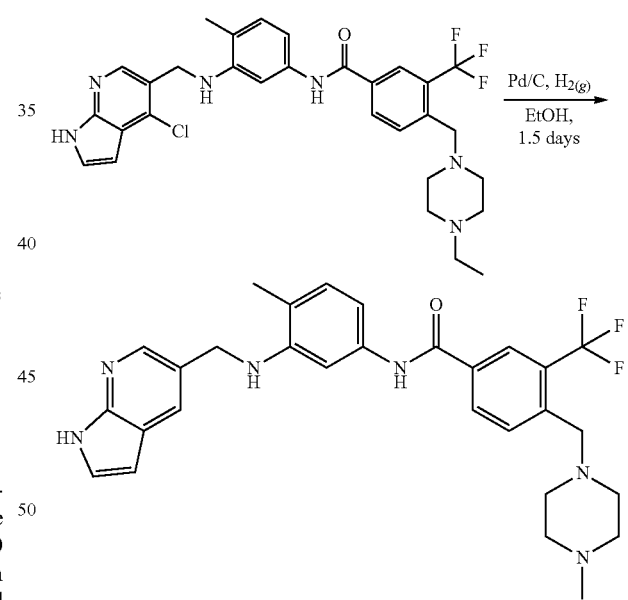

To a solution N-(3-((4-chloro-1H-pyrrolo[2,3-b]pyridin-5-yl)methylamino)-4-methylphenyl)-4-((4-methylpiperazin-1-yl)methyl)-3-(trifluoromethyl)benzamide (10 mg, 0.017 mmol) in EtOH (1.0 mL) was added 10% Pd/C (2 mg). After two vacuum/H$_2$ cycles to replace air inside the reaction flask with hydrogen balloon, the reaction mixture was stirred at room temperature for 36 hours. The reaction mixture was filtered with a pad of celite and concentrated under reduced pressure. The crude product was purified by Prep HPLC and acetonitrile was removed under reduced pressure. The remained water was freeze-dried to afford TFA salt formed title compound (4 mg, 35% yield). MS m/z: 537 [M+1].

Additional compounds made by the synthetic route of Example 8 are found in FIG. 8.
Example 9
4-((4-ethylpiperazin-1-yl)methyl)-N-(3-(((4-methoxy-1H-pyrrolo[2,3-b]pyridin-5-yl)methylamino)-4-methylphenyl)-3-(methylphenyl)-3-(trifluoromethyl) benzamide
IX-1
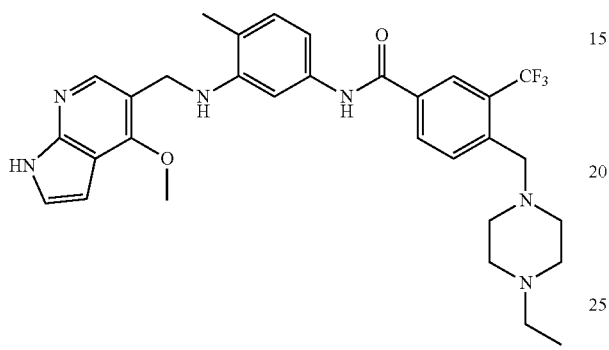
Scheme 9.
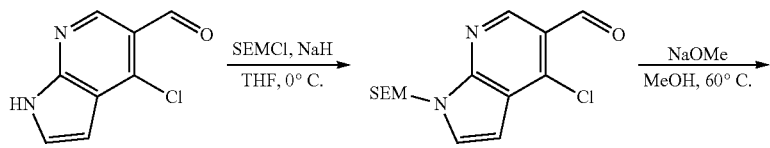
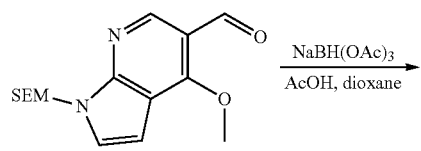
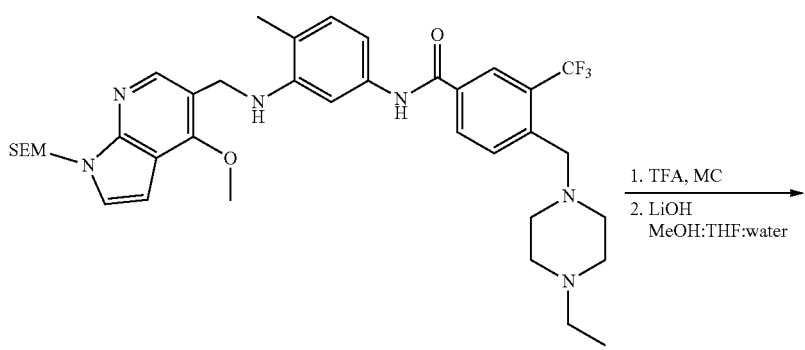

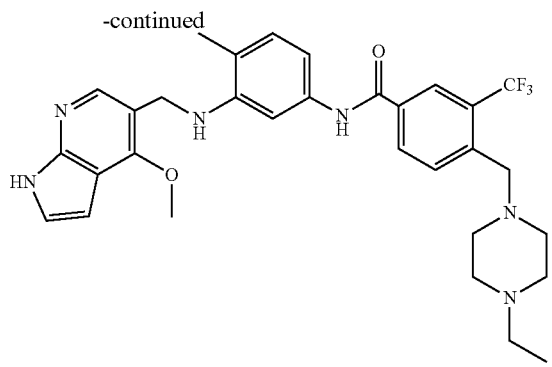

A. 4-chloro-1-((2-(trimethylsilyl)ethoxy)methyl)-1H-pyrrolo[2,3-b]pyridine-5-carbaldehyde

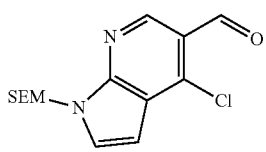 [SMILES: C[Si](C)(C)CCOCn1ccc2c(Cl)c(C=O)cnc21]

To a solution of 4-chloro-1H-pyrrolo[2,3-b]pyridine-5-carbaldehyde (500 mg, 2.78 mmol) in THF (9 mL) was added NaH (136 mg, 3.42 mmol) at 0° C. After 10 minutes, SEMCl (0.59 mL. 3.33 mmol) was added slowly to the reaction mixture at 0° C. The reaction mixture was warmed to room temperature and stirred for 2 hours after which, it was partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product was purified by flash chromatography using (5% to 20% Ethyl acetate/Hexane) as a solvent to afford title compound (810 mg, 94% yield). $^1$H NMR (600 MHz, CDCl$_3$) δ 10.62 (s, 1H), 8.90 (s, 1H), 7.52 (d, J=3.6 Hz, 1H), 6.84 (d, J=4.2 Hz, 1H), 5.76 (s, 2H), 3.60 (t, J=8.4 Hz, 2H), 0.97 (t, J=8.4 Hz, 2H), 0 (s, 9H).

B. 4-methoxy-1-((2-(trimethylsilyl)ethoxy)methyl)-1H-pyrrolo[2,3-b]pyridine-5-carbaldehyde

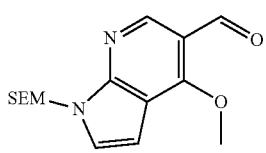 [SMILES: COc1c(C=O)cnc2c1ccn2COCC[Si](C)(C)C]

Na (370 mg, 16.12 mmol) was dissolved in MeOH (5 mL) and 4-chloro-1-((2-(trimethylsilyl)ethoxy)methyl)-1H-pyrrolo[2,3-b]pyridine-5-carbaldehyde (500 mg, 1.61 mmol) was added to the sodium methoxide solution. The reaction mixture was stirred for 8 hours for 60° C. The reaction mixture was quenched with water and the organic solvent was removed under reduced pressure. The resulting mixture was partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product was purified by flash chromatography using (5% to 20% Ethyl acetate/Hexane) as a solvent to afford title compound (380 mg, 77% yield). $^1$H NMR (600 MHz, CDCl$_3$) δ 10.51 (s, 1H), 8.74 (s, 1H), 7.36 (d, J=3.6 Hz, 1H), 6.90 (d, J=4.2 Hz, 1H), 5.72 (s, 2H), 4.48 (s, 3H), 3.60 (t, J=7.8 Hz, 2H), 0.97 (t, J=8.4 Hz, 2H), 0 (s, 9H). MS m/z: 307 [M+1].

C. 4-((4-ethylpiperazin-1-yl)methyl)-N-(3-((4-methoxy-1-((2-(trimethylsilyl)ethoxy)methyl)-1H-pyrrolo[2,3-b]pyridin-5-yl)methylamino)-4-methylphenyl)-3-(trifluoromethyl)benzamide

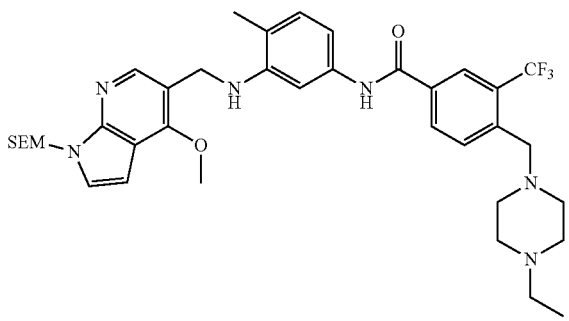 [SMILES: CCN1CCN(Cc2ccc(C(=O)Nc3ccc(C)c(NCc4cnc5c(ccn5COCC[Si](C)(C)C)c4OC)c3)cc2C(F)(F)F)CC1]

To a solution of 4-methoxy-1-((2-(trimethylsilyl)ethoxy)methyl)-1H-pyrrolo[2,3-b]pyridine-5-carbaldehyde (30 mg, 0.10 mmol) in dioxane (1 mL) were added NaBH(OAc)$_3$ (103 mg, 0.83 mmol) and AcOH (6 μL, 0.10 mmol). The reaction mixture was stirred overnight at room temperature. The reaction mixture was neutralized with sat. NaHCO$_3$ and the aqueous layer was extracted with ethyl acetate. The organic extracts were washed with brine, dried over MgSO$_4$, celite filtered and concentrated under reduced pressure. The crude product was purified by flash chromatography using (1% to 7% MeOH/CH$_2$Cl$_2$) as a solvent to afford title compound (43 mg, 61% yield). MS m/z: 711 [M+1].

D. 4-((4-ethylpiperazin-1-yl)methyl)-N-(3-((4-methoxy-1H-pyrrolo[2,3-b]pyridin-5-yl)methylamino)-4-methylphenyl)-3-(trifluoromethyl)benzamide

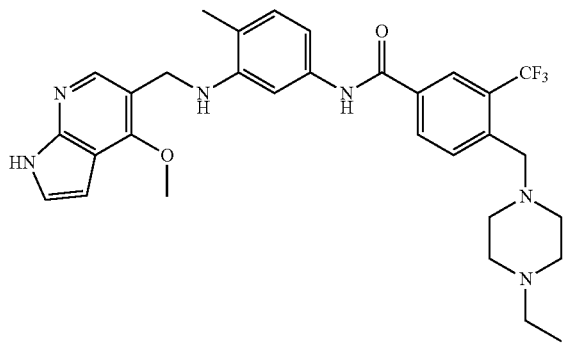 [SMILES: CCN1CCN(Cc2ccc(C(=O)Nc3ccc(C)c(NCc4cnc5[nH]ccc5c4OC)c3)cc2C(F)(F)F)CC1]

To a solution of 4-((4-ethylpiperazin-1-yl)methyl)-N-(3-((4-methoxy-1-((2-(trimethylsilyl)ethoxy)methyl)-1H-pyrrolo[2,3-b]pyridin-5-yl)methylamino)-4-methylphenyl)-3-(trifluoromethyl)benzamide (40 mg, 0.042 mmol) in CH$_2$Cl$_2$ (1 mL) was added TFA (16 □L). The reaction mixture was stirred for 1 hour and the organic solvent was concentrated under reduced pressure. To a solution of the resulting mixture in THF (0.3 mL) and MeOH (0.3 mL) was added LiOH.H$_2$O (17 mg, 0.42 mmol) in water (0.3 mL). The reaction mixture was stirred for 2 hours at room temperature. The organic solvent was removed under reduced pressure and the aqueous layer was extracted with ethyl acetate. The organic extracts were washed with brine, dried over MgSO$_4$, celite filtered and concentrated under reduced pressure. The crude product was purified by Prep HPLC and acetonitrile was removed under reduced pressure. The remained water was freeze-dried to afford TFA salt formed title compound (21 mg, 71% yield). MS m/z: 581 [M+1].

Additional compounds made by the synthetic route of Example 9 are found in FIGS. 9A to 9C.

Example 10

4-((4-ethylpiperazin-1-yl)methyl)-N-(3-((4-(isopropylthio)-1H-pyrrolo[2,3-b]pyridin-5-yl)methylamino)-4-methylphenyl)-3-(trifluoromethyl)benzamide

X-1

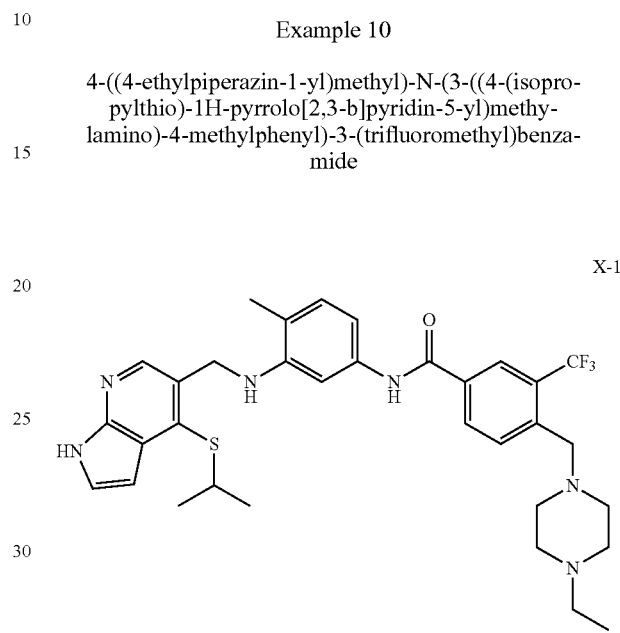

Scheme 10

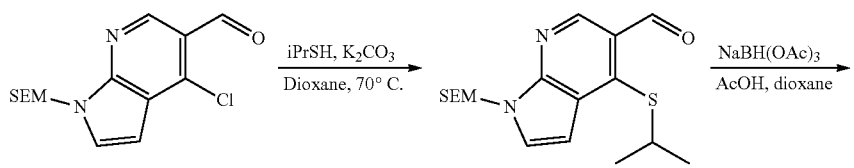

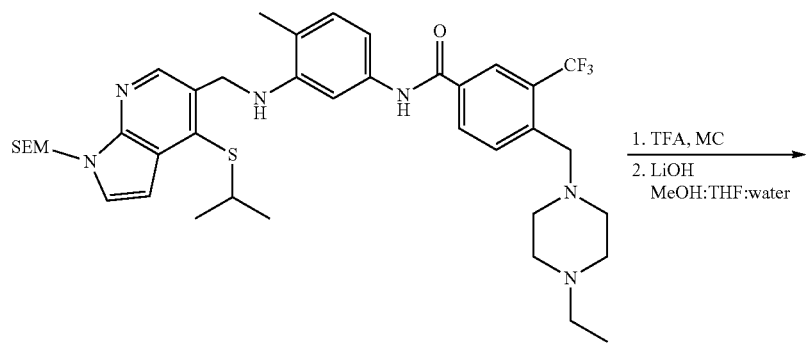

-continued

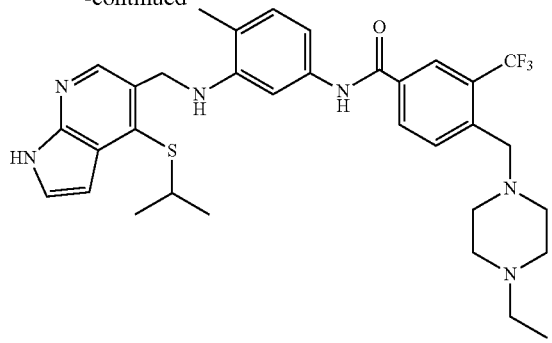
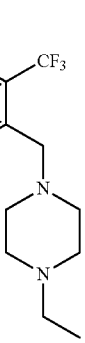

A. 4-(isopropylthio)-1-((2-(trimethylsilyl)ethoxy)methyl)-1H-pyrrolo[2,3-b]pyridine-5-carbaldehyde

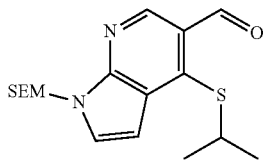

To a solution of 4-chloro-1-((2-(trimethylsilyl)ethoxy)methyl)-1H-pyrrolo[2,3-b]pyridine-5-carbaldehyde (500 mg, 1.61 mmol) in dioxane (5 mL) were added $K_2CO_3$ (668 mg, 4.83 mmol) and 2-propanethiol (0.3 mL, 3.22 mmol). The reaction mixture was stirred for overnight for 70° C. The reaction mixture was partitioned between ethyl acetate and water. The organic layer was separated and the aqueous layer was extracted with ethyl acetate. The combined organic extracts were washed with brine, dried over $MgSO_4$, celite filtered and concentrated under reduced pressure. The crude product was purified by flash chromatography using (5% to 20% Ethyl acetate/Hexane) as a solvent to afford title compound (320 mg, 56% yield). MS m/z: [M+1].

B. 4-((4-ethylpiperazin-1-yl)methyl)-N-(3-((4-(isopropylthio)-1-((2-(trimethylsilyl)ethoxy)methyl)-1H-pyrrolo[2,3-b]pyridin-5-yl)methylamino)-4-methylphenyl)-3-(trifluoromethyl)benzamide

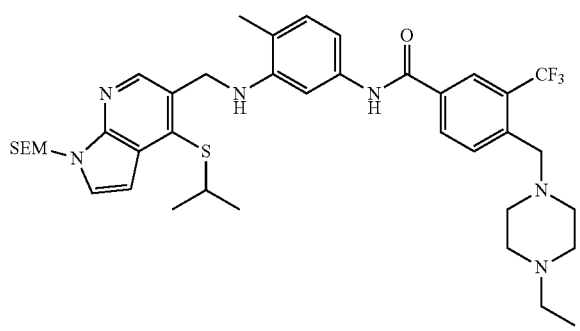 [SMILES: CCN1CCN(Cc2ccc(C(=O)Nc3ccc(C)c(NCc4cnc5c(ccn5COCC[Si](C)(C)C)c4SC(C)C)c3)cc2C(F)(F)F)CC1]

4-((4-ethylpiperazin-1-yl)methyl)-N-(3-((4-(isopropylthio)-1-((2-(trimethylsilyl)ethoxy)methyl)-1H-pyrrolo[2,3-b]pyridin-5-yl)methylamino)-4-methylphenyl)-3-(trifluoromethyl)benzamide (46 mg, 71% yield) was prepared as described for Example 9-C starting from 4-(isopropylthio)-1-((2-(trimethylsilyl)ethoxy)methyl)-1H-pyrrolo[2,3-b]pyridine-5-carbaldehyde (30 mg, 0.085 mmol). MS m/z: 755 [M+1].

C. 4-((4-ethylpiperazin-1-yl)methyl)-N-(3-((4-(isopropylthio)-1H-pyrrolo[2,3-b]pyridin-5-yl)methylamino)-4-methylphenyl)-3-(trifluoromethyl)benzamide

IX-1

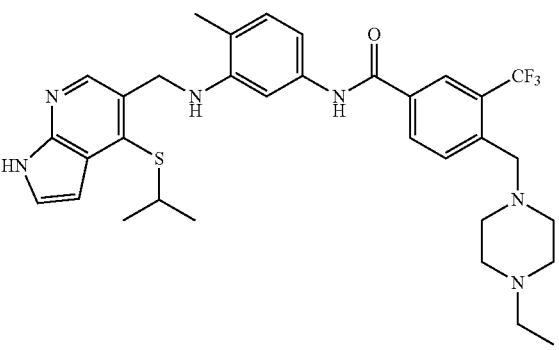

4-((4-ethylpiperazin-1-yl)methyl)-N-(3-((4-(isopropylthio)-1H-pyrrolo[2,3-b]pyridin-5-yl)methylamino)-4-methylphenyl)-3-(trifluoromethyl)benzamide (18 mg, 52% yield) was prepared as described for Example 9-D starting from 4-((4-ethylpiperazin-1-yl)methyl)-N-(3-((4-(isopropylthio)-1-((2-(trimethylsilyl)ethoxy)methyl)-1H-pyrrolo[2,3-b]pyridin-5-yl)methylamino)-4-methylphenyl)-3-(trifluoromethyl)benzamide (35 mg, 0.046 mmol). MS m/z: 625 [M+1].

Additional compounds made by the synthetic route of Example 10 are found in FIGS. 10A to 10B.

Example 11

(E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide

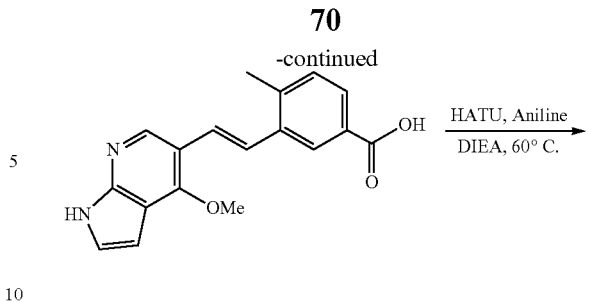

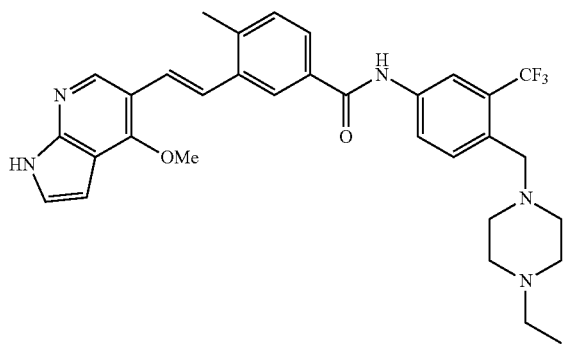

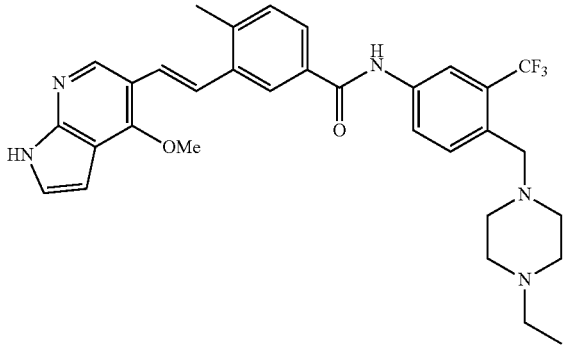

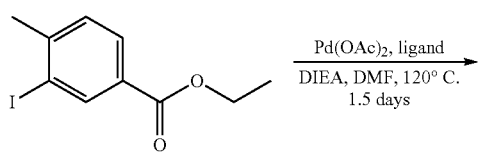

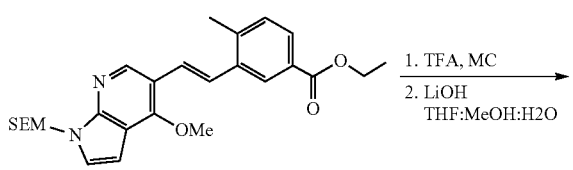

A. 4-methoxy-1-((2-(trimethylsilyl)ethoxy)methyl)-5-vinyl-1H-pyrrolo[2,3-b]pyridine

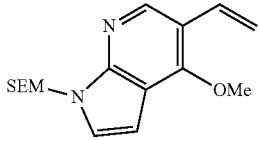 [SMILES: C=Cc1cnc2c(ccn2COCC[Si](C)(C)C)c1OC]

To a solution methyltriphenylphosphonium iodide (782 mg, 1.93 mmol) in dried THF (5 mL) was added 2.5 M n-BuLi in Hexane (0.74 mL, 1.85 mmol) at −78° C. After 10 minutes, 4-methoxy-1-((2-(trimethylsilyl)ethoxy)methyl)-1H-pyrrolo[2,3-b]pyridine-5-carbaldehyde (493 mg, 1.61 mmol) was added to the reaction mixture. The reaction mixture was warmed to room temperature spontaneously. After 2 hours, the reaction mixture was quenched with water and was partitioned between ethyl acetate and water. The organic layer was separated and the aqueous layer was extracted with ethyl acetate. The combined organic extracts were washed with brine, dried over MgSO$_4$, celite filtered and concentrated under reduced pressure. The crude product was purified by flash chromatography using (5% to 15% Ethyl acetate/Hexane) as a solvent to afford title compound (371 mg, 76% yield). $^1$H NMR (600 MHz, CDCl$_3$) δ 8.40 (s, 1H), 7.27 (d, J=3.6 Hz, 1H), 7.07 (dd, J=11.4, 18 Hz, 1H), 6.78 (d, J=3.6 Hz, 1H), 5.78 (d, J=18 Hz, 1H), 5.70 (s, 2H), 5.30 (d, J=11.4 Hz, 1H), 4.38 (s, 3H), 3.60 (t, J=8.4 Hz, 2H), 0.97 (t, J=8.4 Hz, 2H), 0 (s, 9H). MS m/z: 305 [M+1].

B. (E)-ethyl 3-(2-(4-methoxy-1-((2-(trimethylsilyl) ethoxy)methyl)-1H-pyrrolo[2,3-b]pyridin-5-yl)vinyl)-4-methylbenzoate D. (E)-N-(4-((4-ethylpiperazin-1-yl)methyl)-3-(trifluoromethyl)phenyl)-3-(2-(4-methoxy-1H-pyrrolo[2,3-b]pyridin-5-yl)vinyl)-4-methylbenzamide

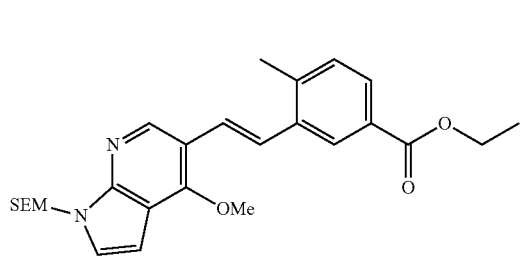 [SMILES: CCOC(=O)c1ccc(C)c(/C=C/c2cnc3c(ccn3COCC[Si](C)(C)C)c2OC)c1]

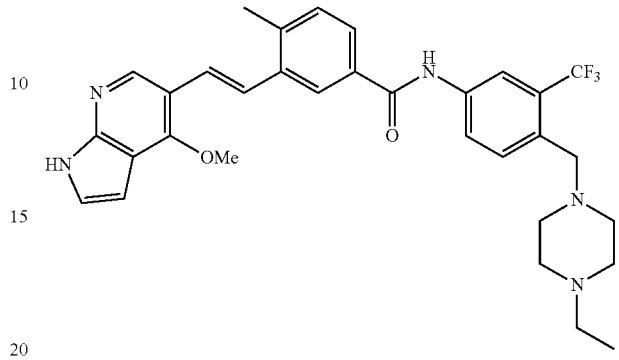

(E)-ethyl 3-(2-(4-methoxy-1-((2-(trimethylsilyl)ethoxy)methyl)-1H-pyrrolo[2,3-b]pyridin-5-yl)vinyl)-4-methylbenzoate (302 mg, 58% yield) was prepared as described for Example 5-C starting from 4-methoxy-1-((2-(trimethylsilyl) ethoxy)methyl)-5-vinyl-1H-pyrrolo[2,3-b]pyridine (340 mg, 1.12 mmol) and ethyl 3-iodo-4-methylbenzoate (360 mg, 1.24 mmol). $^1$H NMR (600 MHz, CDCl$_3$) δ 8.52 (s, 1H), 8.35 (d, J=1.2 Hz, 1H), 7.87 (dd, J=1.8, 7.8 Hz, 1H), 7.45 (d, J=16.2 Hz, 1H), 7.34 (d, J=16.2 Hz, 1H), 7.31-7.27 (m, 2H), 6.81 (d, J=3.6 Hz, 1H), 5.71 (s, 2H), 4.45 (q, J=7.2 Hz, 2H), 4.43 (s, 3H), 3.62 (t, J=8.4 Hz, 2H), 2.51 (s, 3H), 1.46 (t, J=7.2 Hz, 3H), 0.97 (t, J=8.4 Hz, 2H), 0 (s, 9H). MS m/z: 467 [M+1].

C. (E)-3-(2-(4-methoxy-1H-pyrrolo[2,3-b]pyridin-5-yl)vinyl)-4-methylbenzoic acid

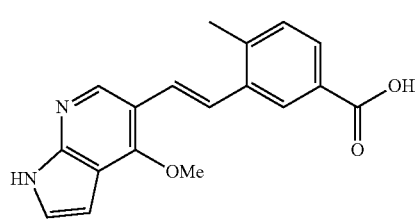 [SMILES: COc1c(/C=C/c2cc(C(=O)O)ccc2C)cnc2[nH]ccc12]

To a solution of (E)-ethyl 3-(2-(4-methoxy-1-((2-(trimethylsilyl)ethoxy)methyl)-1H-pyrrolo[2,3-b]pyridin-5-yl)vinyl)-4-methylbenzoate (298 mg, 0.64 mmol) in CH$_2$Cl$_2$ (2 mL) was added TFA (0.24 mL, 3.19 mmol). The reaction mixture was stirred for 1 hour and the organic solvent was concentrated under reduced pressure. To a solution of the resulting mixture in THF (2 mL) and MeOH (2 mL) was added LiOH.H$_2$O (535 mg, 0.42 mmol) in water (2 mL). The reaction mixture was stirred for 8 hours at room temperature. To a reaction mixture was added 1N HCl solution to produce solid. The solid product was filtered and dried with nitrogen gas flow. The title product (128 mg, 65% yield) was used without further purification. MS m/z: 309 [M+1].

To a solution of (E)-3-(2-(4-methoxy-1H-pyrrolo[2,3-b] pyridin-5-yl)vinyl)-4-methylbenzoic acid (20 mg, 0.064 mmol) in DMF (1 mL) were added HATU (73 mg, 0.19 mmol), DIEA (56 □L, 0.32 mmol) and 4-((4-ethylpiperazin-1-yl)methyl)-3-(trifluoromethyl)benzenamine (18 mg, 0.064 mmol). The reaction mixture was stirred for overnight at 60° C. after which, it was partitioned between ethyl acetate and water. The organic layer was separated and the aqueous layer was extracted with ethyl acetate. The combined organic extracts were washed with brine, dried over MgSO$_4$, filtered and concentrated. The crude product was purified by Prep HPLC and acetonitrile was removed under reduced pressure. The remained water was freeze-dried to afford TFA salt formed title compound (23 mg, 51% yield). $^1$H NMR (600 MHz, CD$_3$OD) δ 8.31 (s, 1H), 8.17 (d, J=1.8 Hz, 1H), 8.10 (d, J=2.4 Hz, 1H), 7.91 (dd, J=1.8, 8.4 Hz, 1H), 7.71-7.67 (m, 2H), 7.41 (d, J=16.8 Hz, 1H), 7.32 (d, J=16.2 Hz, 1H), 7.25 (d, J=7.8 Hz, 1H), 7.23 (d, J=3.6 Hz, 1H), 6.78 (d, J=3.6 Hz, 1H), 4.35 (s, 3H), 3.61 (s, 2H), 2.60-2.40 (m, 13H), 1.08 (t, J=7.2 Hz, 3H). MS m/z: 578 [M+1].

Additional compounds made by the synthetic route of Example 11 are found in FIGS. 11A to 11B.

Example 12

5-(1H-pyrrolo[2,3-b]pyridin-4-yloxy)-N-(3-(trifluoromethyl)phenyl)-1-naphthamide

XXI-1

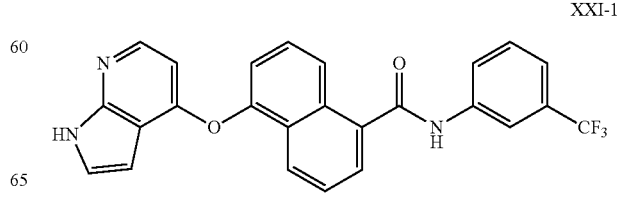

Scheme 12.

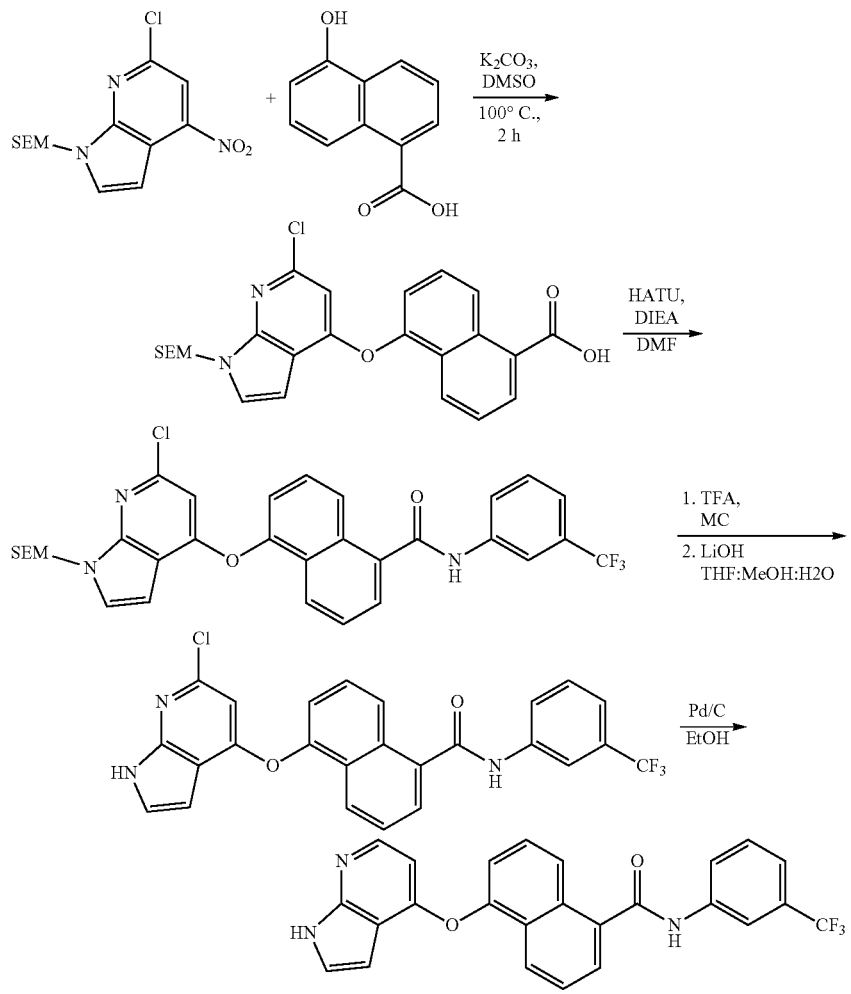

A. 5-(6-chloro-1-((2-(trimethylsilyl)ethoxy)methyl)-1H-pyrrolo[2,3-b]pyridin-4-yloxy)-1-naphthoic acid

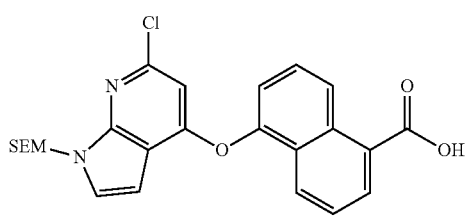 [SMILES: C[Si](C)(C)CCOCn1ccc2c(Oc3cccc4c(C(=O)O)cccc34)cc(Cl)nc21]

To a solution of 6-chloro-4-nitro-1-((2-(trimethylsilyl)ethoxy)methyl)-1H-pyrrolo[2,3-b]pyridine (400 mg, 1.22 mmol) in DMSO (4 mL) were added $K_2CO_3$ (507 mg, 3.67 mmol) and 5-hydroxy-1-naphthoic acid (230 mg, 1.22 mmol). The reaction mixture was stirred for overnight at 100° C. after which, It was cooled to room temperature. To the reaction mixture was added 1N HCl solution to reach pH=5. The produced solid was filtered and dried nitrogen gas flow.

The title compound (380 mg, 66% yield) was used next reaction without further purification. MS m/z: 469 [M+1].

B. 5-(6-chloro-1-((2-(trimethylsilyl)ethoxy)methyl)-1H-pyrrolo[2,3-b]pyridin-4-yloxy)-N-(3-(trifluoromethyl)phenyl)-1-naphthamide

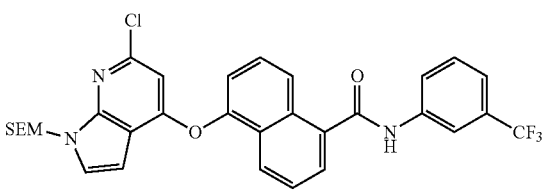 [SMILES: C[Si](C)(C)CCOCn1ccc2c(Oc3cccc4c(C(=O)Nc5cccc(C(F)(F)F)c5)cccc34)cc(Cl)nc21]

5-(6-chloro-1-((2-(trimethylsilyl)ethoxy)methyl)-1H-pyrrolo[2,3-b]pyridin-4-yloxy)-N-(3-(trifluoromethyl)phenyl)-1-naphthamide (92 mg, 88% yield) was prepared as described for Example 11-D starting from 5-(6-chloro-1-((2-(trimethylsilyl)ethoxy)methyl)-1H-pyrrolo[2,3-b]pyridin-4-yloxy)-

1-naphthoic acid (80 mg, 0.17 mmol) and 3-(trifluoromethyl)benzenamine (55 mg, 0.34 mmol). MS m/z: 612 [M+1].

C. 5-(6-chloro-1H-pyrrolo[2,3-b]pyridin-4-yloxy)-N-(3-(trifluoromethyl)phenyl)-1-naphthamide

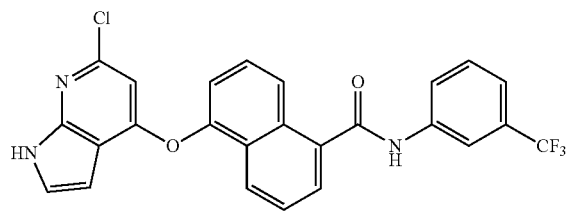 [SMILES: O=C(Nc1cccc(C(F)(F)F)c1)c1cccc2c(Oc3cc(Cl)nc4[nH]ccc34)cccc12]

5-(6-chloro-1H-pyrrolo[2,3-b]pyridin-4-yloxy)-N-(3-(trifluoromethyl)phenyl)-1-naphthamide (48 mg, 71% yield) was prepared as described for Example 9-D starting from 5-(6-chloro-1-((2-(trimethylsilyl)ethoxy)methyl)-1H-pyrrolo[2,3-b]pyridin-4-yloxy)-N-(3-(trifluoromethyl)phenyl)-1-naphthamide (85 mg, 0.14 mmol). MS m/z: 482 [M+1].

D. 5-(1H-pyrrolo[2,3-b]pyridin-4-yloxy)-N-(3-(trifluoromethyl)phenyl)-1-naphthamide

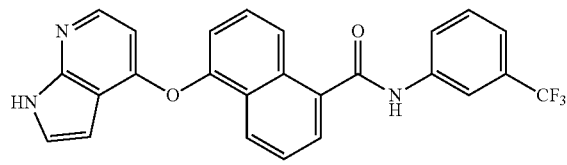 [SMILES: O=C(Nc1cccc(C(F)(F)F)c1)c1cccc2c(Oc3ccnc4[nH]ccc34)cccc12]

5-(1H-pyrrolo[2,3-b]pyridin-4-yloxy)-N-(3-(trifluoromethyl)phenyl)-1-naphthamide (9 mg, 32% yield) was prepared as described for Example 8 starting from 5-(6-chloro-1H-pyrrolo[2,3-b]pyridin-4-yloxy)-N-(3-(trifluoromethyl)phenyl)-1-naphthamide (30 mg, 0.062 mmol). MS m/z: 448 [M+1].

Additional compounds made by the synthetic route of Example 12 are found in FIGS. 12A to 12D.

Example 13

5-(6-(4-(piperazin-1-ylsulfonyl)phenylamino)-1H-pyrrolo[2,3-b]pyridin-4-yloxy)-N-(3-(trifluoromethyl)phenyl)-1-naphthamide

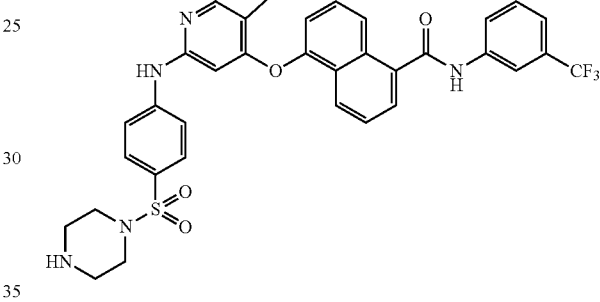

XIII-1

Scheme 13.

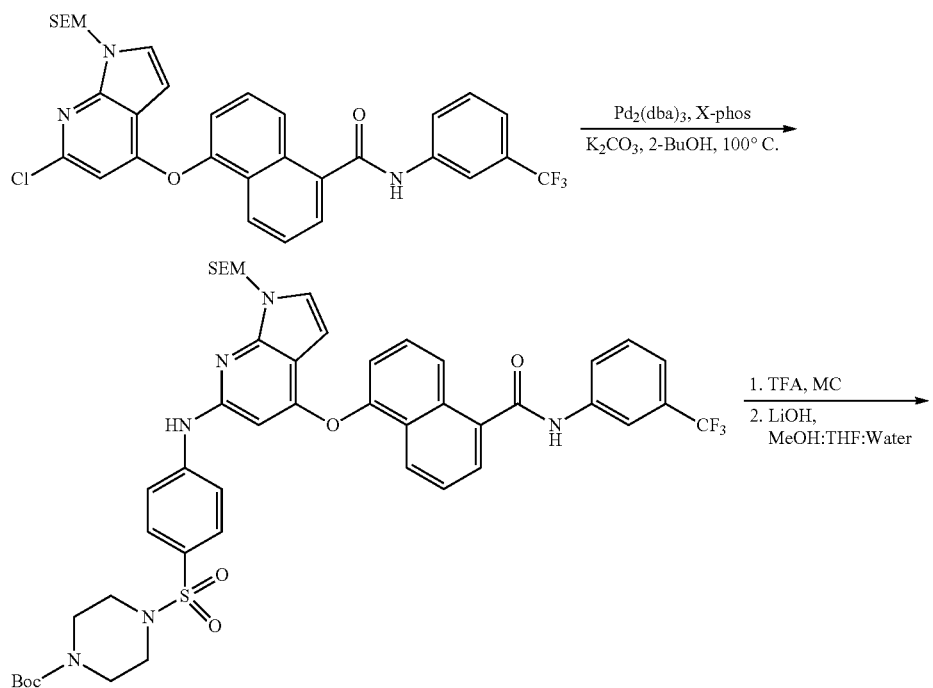

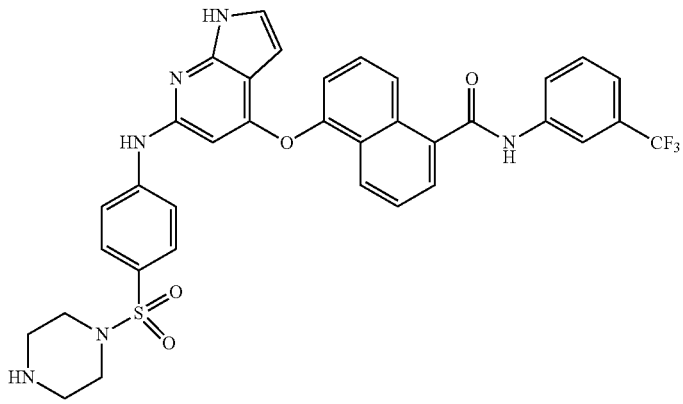

A. tert-butyl 4-(4-(4-(5-(3-(trifluoromethyl)phenyl-carbamoyl)naphthalen-1-yloxy)-1-((2-(trimethylsi-lyl)ethoxy)methyl)-1H-pyrrolo[2,3-b]pyridin-6-ylamino)phenylsulfonyl)piperazine-1-carboxylate

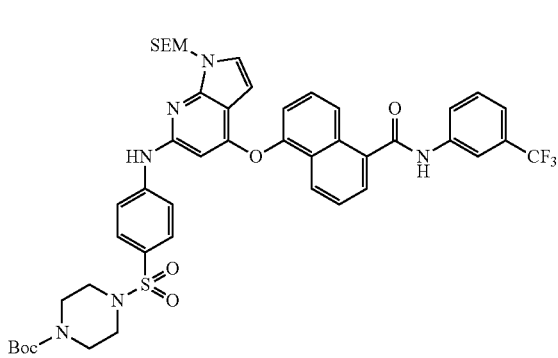 [SMILES: CC(C)(C)OC(=O)N1CCN(S(=O)(=O)c2ccc(Nc3cc(Oc4cccc5c(C(=O)Nc6cccc(C(F)(F)F)c6)cccc45)c4ccn(COCC[Si](C)(C)C)c4n3)cc2)CC1]

tert-butyl 4-(4-(4-(5-(3-(trifluoromethyl)phenylcarbam-oyl)naphthalen-1-yloxy)-1-((2-(trimethylsilyl)ethoxy)me-thyl)-1H-pyrrolo[2,3-b]pyridin-6-ylamino)phenylsulfonyl) piperazine-1-carboxylate (42 mg, 70% yield) was prepared as described for Example 5-B starting from 5-(6-chloro-1-((2-(trimethylsilyl)ethoxy)methyl)-1H-pyrrolo[2,3-b]pyridin-4-yloxy)-N-(3-(trifluoromethyl)phenyl)-1-naphthamide (40 mg, 0.065 mmol) and tert-butyl 4-(4-aminophenylsulfonyl) piperazine-1-carboxylate (22 mg, 0.065 mmol). MS m/z: 917 [M+1].

B. 5-(6-(4-(piperazin-1-ylsulfonyl)phenylamino)-1H-pyrrolo[2,3-b]pyridin-4-yloxy)-N-(3-(trifluorom-ethyl)phenyl)-1-naphthamide

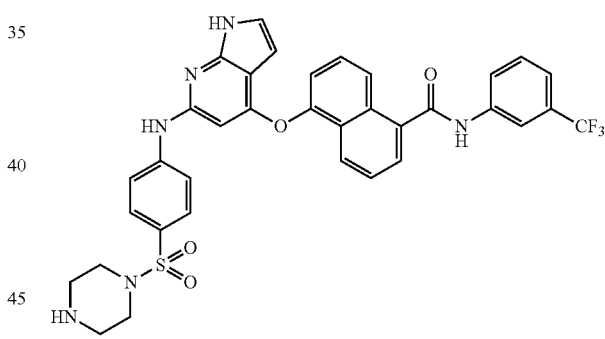

5-(6-(4-(piperazin-1-ylsulfonyl)phenylamino)-1H-pyr-rolo[2,3-b]pyridin-4-yloxy)-N-(3-(trifluoromethyl)phenyl)-1-naphthamide (22 mg, 64% yield) was prepared as described for Example 9-D starting from tert-butyl 4-(4-(4-(5-(3-(trif-luoromethyl)phenylcarbamoyl) naphthalen-1-yloxy)-1-((2-(trimethylsilyl)ethoxy)methyl)-1H-pyrrolo[2,3-b]pyridin-6-ylamino)phenylsulfonyl)piperazine-1-carboxylate (40 mg, 0.043 mmol). MS m/z: 687 [M+1].

Additional compounds made by the synthetic route of Example 13 are found in FIG. 13.

Example 14

Additional Compounds

The following compounds were made in a manner similar to the synthesis found in Example 6.

| Structure | Name | ¹H NMR, and or MS (m/z) |
|---|---|---|
| 1 | 4-methoxy-N-(2-methyl-5-((3-(trifluoromethyl)phenyl)-carbamoyl)phenyl)-1H-pyrrolo[2,3-b]pyridine-5-carboxamide | ¹H NMR (600 MHz, DMSO-d$_6$) δ 11.98 (s, 1H), 10.52 (s, 1H), 9.80 (s, 1H), 8.65 (s, 1H), 8.52 (s, 1H), 8.24 (s, 1H), 8.07 (d, J = 7.8 Hz, 1H), 7.72 (dd, J = 1.2, 7.8 Hz, 1H), 7.59 (t, J = 7.8 Hz, 1H), 7.47-7.43 (m, 3H), 6.93 (s, 1H), 4.46 (s, 3H), 2.41 (s, 3H). MS m/z: 469 [M + 1] |
| 2 | 4-methoxy-N-(2-methyl-5-((4-((4-methylpiperazin-1-yl)methyl)-3-(trifluoromethyl)phenyl)-carbamoyl)phenyl)-1H-pyrrolo[2,3-b]pyridine-5-carboxamide | MS m/z: 581 [M + 1] |
| 3 | N-(5-(4-((4-ethylpiperazin-1-yl)methyl)-3-(trifluoromethyl)benzamido)-2-methylphenyl)-4-methoxy-1H-pyrrolo[2,3-b]pyridine-5-carboxamide | MS m/z: 595 [M + 1] |
| 4 | 3-((1H-pyrrolo[2,3-b]pyridin-4-yl)oxy)-4-methyl-N-(3-(trifluoromethyl)phenyl)-benzamide | MS m/z: 412 [M + 1] |
| 5 | 3-((1H-pyrrolo[2,3-b]pyridin-4-yl)oxy)-4-methyl-N-(3-(4-methyl-1H-imidazol-1-yl)-5-(trifluoromethyl)phenyl)-benzamide | MS m/z: 492 [M + 1] |
| 6 | 3-((7H-pyrrolo[2,3-d]pyrimidin-4-yl)oxy)-N-(4-((4-ethylpiperazin-1-yl)methyl)-3-(trifluoromethyl)phenyl)-4-methylbenzamide | MS m/z: 539 [M + 1] |

-continued

| Structure | Name | ¹H NMR, and or MS (m/z) |
|---|---|---|
| 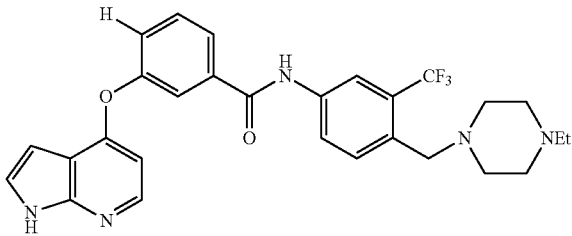 7 | 3-((1H-pyrrolo[2,3-b]pyridin-4-yl)oxy)-N-(4-((4-ethylpiperazin-1-yl)methyl)-3-(trifluoromethyl)phenyl)-benzamide | MS m/z: 524 [M + 1] |
| 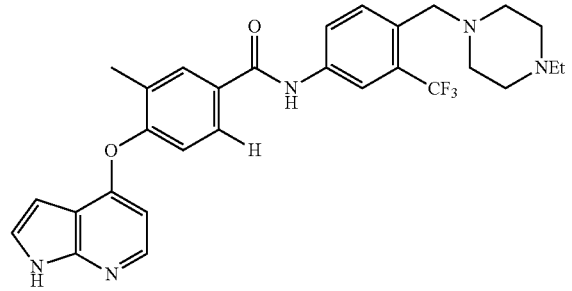 8 | 4-((1H-pyrrolo[2,3-b]pyridin-4-yl)oxy)-N-(4-((4-ethylpiperazin-1-yl)methyl)-3-(trifluoromethyl)phenyl)-3-methylbenzamide | MS m/z: 538 [M + 1] |
| 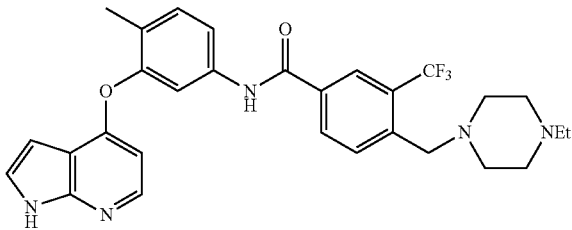 9 | N-(3-((1H-pyrrolo[2,3-b]pyridin-4-yl)oxy)-4-methylphenyl)-4-((4-ethylpiperazin-1-yl)methyl)-3-(trifluoromethyl)benzamide | MS m/z: 538 [M + 1] |
| 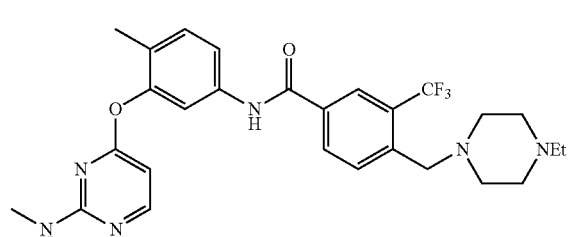 10 | N-(4-((4-ethylpiperazin-1-yl)methyl)-3-(trifluoromethyl)phenyl)-4-methyl-3-((2-(methylamino)pyrimidin-4-yl)oxy)benzamide | MS m/z: 529 [M + 1] |
| 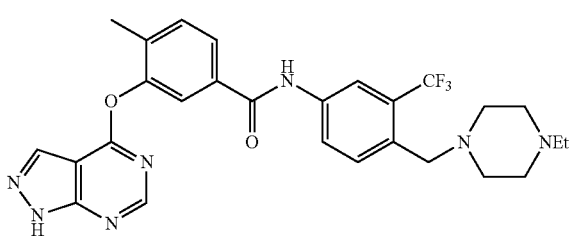 11 | 3-((1H-pyrazolo[3,4-d]pyrimidin-4-yl)oxy)-N-(4-((4-ethylpiperazin-1-yl)methyl)-3-(trifluoromethyl)phenyl)-4-methylbenzamide | MS m/z: 540 [M + 1] |

-continued

| Structure | Name | ¹H NMR, and or MS (m/z) |
|---|---|---|
| 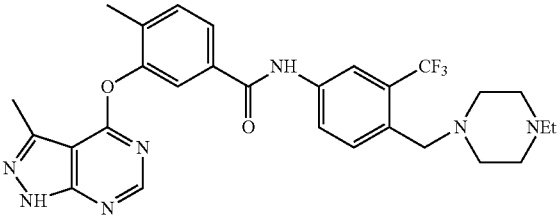 12 | N-(4-((4-ethylpiperazin-1-yl)methyl)-3-(trifluoromethyl)phenyl)-4-methyl-3-((3-methyl-1H-pyrazolo[3,4-d]pyrimidin-4-yl)oxy)benzamide | MS m/z: 554 [M + 1] |
| 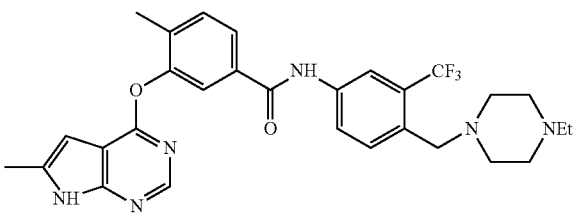 13 | N-(4-((4-ethylpiperazin-1-yl)methyl)-3-(trifluoromethyl)phenyl)-4-methyl-3-((6-methyl-7H-pyrrolo[2,3-d]pyrimidin-4-yl)oxy)benzamide | MS m/z: 553 [M + 1] |
| 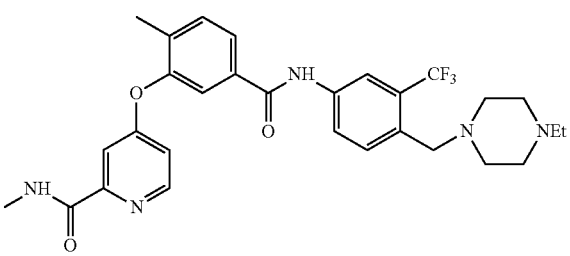 14 | 4-(5-((4-((4-ethylpiperazin-1-yl)methyl)-3-(trifluoromethyl)phenyl)carbamoyl)-2-methylphenoxy)-N-methylpicolinamide | MS m/z: 556 [M + 1] |
| 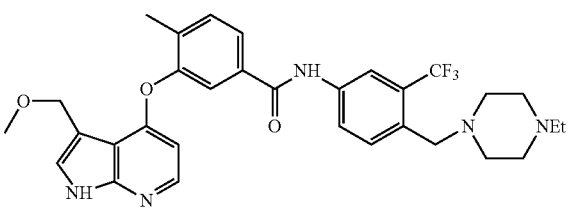 15 | N-(4-((4-ethylpiperazin-1-yl)methyl)-3-(trifluoromethyl)phenyl)-3-((3-(methoxymethyl)-1H-pyrrolo[2,3-b]pyridin-4-yl)oxy)-4-methylbenzamide | MS m/z: 582 [M + 1] |
| 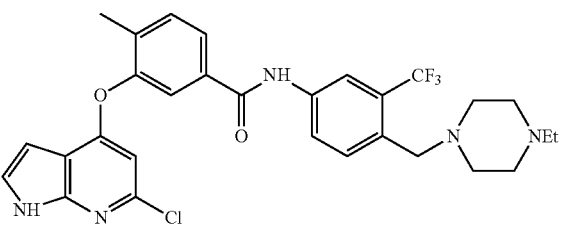 16 | 3-((6-chloro-1H-pyrrolo[2,3-b]pyridin-4-yl)oxy)-N-(4-((4-ethylpiperazin-1-yl)methyl)-3-(trifluoromethyl)phenyl)-4-methylbenzamide | MS m/z: 572 [M + 1] |
| 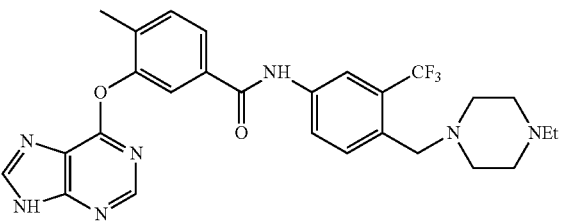 17 | 3-((9H-purin-6-yl)oxy)-N-(4-((4-ethylpiperazin-1-yl)methyl)-3-(trifluoromethyl)phenyl)-4-methylbenzamide | MS m/z: 540 [M + 1] |

-continued

| Structure | Name | ¹H NMR, and or MS (m/z) |
|---|---|---|
| 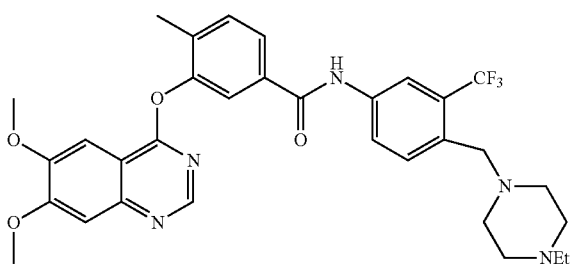 18 | 3-((6,7-dimethoxyquinazolin-4-yl)oxy)-N-(4-((4-ethylpiperazin-1-yl)methyl)-3-(trifluoromethyl)phenyl)-4-methylbenzamide | MS m/z: 610 [M + 1] |
| 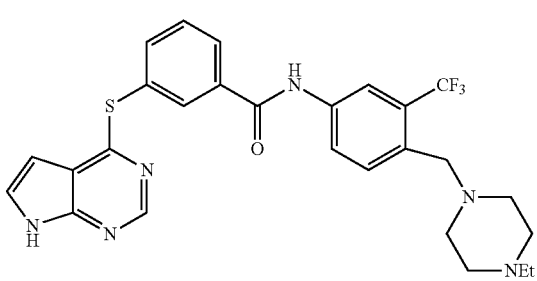 19 | 3-((7H-pyrrolo[2,3-d]pyrimidin-4-yl)thio)-N-(4-((4-ethylpiperazin-1-yl)methyl)-3-(trifluoromethyl)phenyl)-benzamide | MS m/z: 541 [M + 1] |
| 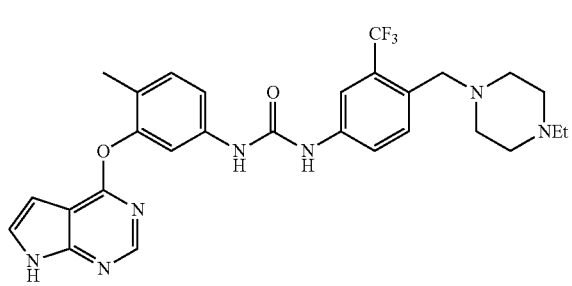 20 | 1-(3-((7H-pyrrolo[2,3-d]pyrimidin-4-yl)oxy)-4-methylphenyl)-3-(4-((4-ethylpiperazin-1-yl)methyl)-3-(trifluoromethyl)phenyl)-urea | MS m/z: 554 [M + 1] |
| 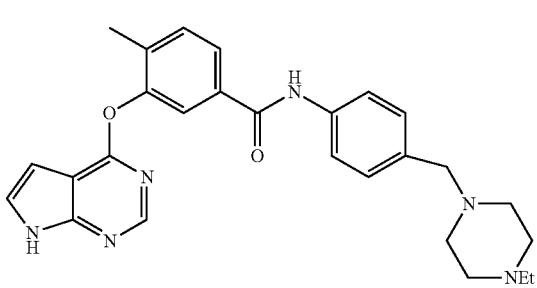 21 | 3-((7H-pyrrolo[2,3-d]pyrimidin-4-yl)oxy)-N-(4-((4-ethylpiperazin-1-yl)methyl)phenyl)-4-methylbenzamide | MS m/z: 471 [M + 1] |

| Structure | Name | $^1$H NMR, and or MS (m/z) |
|---|---|---|
| (structure 22) | 3-((7H-pyrrolo[2,3-d]pyrimidin-4-yl)oxy)-4-methyl-N-(3-methyl-4-((4-methylpiperazin-1-yl)methyl)phenyl)-benzamide | MS m/z: 471 [M + 1] |

Example 15

B-raf Cell Proliferation Assay

Ba/F3 cells and B-RAF transformed Ba/F3 cells were maintained in RPMI 1640 medium supplemented with 10% fetal bovine serum (FBS) in a 5% CO2 incubator at 37° C. The untransformed Ba/F3 cells are supplemented with 1.0 ng/ml of recombinant IL3. 4000 Ba/F3 cells per well were plated in quadruplicate in 384-well plates, in RPMI 1640 media supplemented with 10% FBS and various concentrations of IL3. After 48 h of growth, Brightglo reagent (Promega, Wis.) was added to each well. Luminescent was read as counts/sec. XL-fit was used for IC50 analysis.

XI-1 Inhibits Phosphorylation of JNK and p38 but not Erk1/2 Following Stimulation with Anisomycin.

AZD628 is a potent pan-b-raf inhibitor, PLX4720 is a selective b-raf inhibitor,
BAY61-3036 is a reported Syk kinase inhibitor
Phosphorylation Analysis The phosphorylation levels of Erk, JNK, and p38 were assessed by western blotting using phospho-specific antibodies (results not shown). In brief, cells were treated for 15 min with/without 2 uM anicomycin to stimulate the MAPK-signaling pathways. Next various concentrations of the test compound were added to treat cells for 90 minutes. Cells lysed in lysis buffer (50 mM Tris-HCl pH 7.4, 150 mM NaCl, 5 mM EDTA, 1 mM EGTA, 1% Nonidet P-40, 2 mM Na3VO4 and protease inhibitor cocktail (Roche)). Equal amounts of lysate (50 g) were subjected to SDS-PAGE followed by immunoblotting with phospho-specific antibodies—anti-phospho-Erk (Thr202/Tyr204), anti-phospho-JNK (Thr183/Tyr185) and anti-phospho-p38 (Thr180/Tyr182) antibodies—or antibodies recognizing Erk (Cell signaling). Proteins were detected by enhanced chemioluminescence (ECL-plus; Amersham), following the manufacturer's guidelines.

Incorporation by Reference

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of formula I:

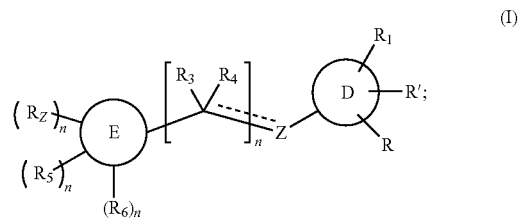

or a pharmaceutically acceptable salt, ester, or prodrug thereof,
wherein,
ring D is aryl or heteroaryl;
R is halo, or -A-B;
A is $NR_AC(O)$, O, $S(O)_m$, C(O), C(O)O, $C(O)NR_A$, $NR_AC(O)NR_A$, or absent;
B is alkyl, cycloalkyl, or aryl, each of which is optionally substituted;
$R_1$ is hydroxyl, alkyl, alkoxy, $C(O)OR_A$, $C(O)NR_AR_B$, or $NR_AR_B$, each of which may be is optionally substituted, or halo;
R' is absent, or R and R' together with the atoms to which each is attached, form a cycloalkyl, heterocycloalkyl, aryl, or heteroaryl ring, each of which is optionally substituted;
Z is $NR_A$, O, $CR_3R_4$ or $S(O)_m$;
$R_3$ is H or alkyl;
$R_4$ is H, alkyl, or absent;
ring E is 1H-pyrrolo[2,3-b]pyridine;
$R_Z$ is $NR_AR_2$;
$R_2$ is H, optionally substituted aryl, optionally substituted heteroaryl, optionally substituted heterocycloalkyl, $C(O)R_A$, $C(O)OR_A$, $C(O)NR_AR_B$, $C(NR_B)R_A$, or $C(NR_B)OR_A$;
$R_5$ is H, halo, alkyl, alkoxy, or thioalkoxy;
$R_6$ is H, $NR_AR_B$, or $OR_A$;
each $R_A$ is independently H, alkyl, alkenyl, cycloalkyl, heterocyclic, aryl or heteroaryl, each of which is optionally substituted;

each $R_B$ is independently H, alkyl, alkenyl, cycloalkyl, heterocyclic, aryl or heteroaryl, each of which is optionally substituted;

or, for each occurrence of $NR_AR_B$, $R_A$ and $R_B$ are taken together with the nitrogen atom to which they are attached to form a 3-7 membered heterocycloalkyl ring;

each m is independently 0, 1, or 2; and each n is independently 0 or 1.

2. The compound of claim 1, wherein ring D is selected from phenyl, naphthyl, tetrahydronaphthyl, indanyl, idenyl, pyridinyl, pyrazinyl, pyrimidinyl, pyrrolyl, pyrazolyl, pyrrolo pyridinyl, thiazolo pyridinyl, imidazolyl, thiazolyl, oxazolyl, isooxazolyl, thiadiazolyl, oxadiazolyl, thiophenyl, furanyl, indazolyl, indolonyl, quinolinyl, isoquinolinyl, benzimidazolyl, benzooxazolyl, and quinoxalinyl.

3. The compound of claim 2, wherein ring D is selected from phenyl, naphthyl, pyrazinyl, pyrimidinyl, pyrrolo pyridinyl, thiazolo pyridinyl, indazolyl, indolonyl, and quinolinyl.

4. A compound of formula IV:

(IV)

or a pharmaceutically acceptable salt, ester or prodrug thereof, wherein,

R is H or -A-B;

A is $NR_AC(O)$, O, $S(O)_m$, C(O), C(O)O, $C(O)NR_A$, or absent;

B is alkyl or aryl, each of which is optionally substituted;

$R_1$ is alkyl, alkoxy, or halo; each of which is optionally substituted;

Z is $NR_A$, O, or $S(O)_m$;

$R_3$ is H or alkyl;

$R_4$ is H or alkyl;

$R_5$ is H, halo, alkoxy, or thioalkoxy;

each $R_A$ is independently H, alkyl, alkenyl, cycloalkyl, heterocyclic, aryl or heteroaryl, each of which is optionally substituted; and each m is independently 0, 1, or 2.

5. The compound of claim 1, of formula V:

(V)

or a pharmaceutically acceptable salt, ester or prodrug thereof, wherein,

R is -A-B;

A is $NR_AC(O)$, O, $S(O)_m$, C(O), C(O)O, $C(O)NR_A$, or absent;

B is alkyl or aryl, each of which is optionally substituted;

$R_1$ is alkyl, alkoxy, or halo; each of which is optionally substituted;

$R_5$ is H, halo, alkoxy, or thioalkoxy;

each $R_A$ is independently H, alkyl, alkenyl, cycloalkyl, heterocyclic, aryl, or heteroaryl, each of which is optionally substituted; and m is 0, 1, or 2.

6. The compound of claim 1, wherein the compound is of the formula:

(VII-2)

(VII-3)

(VII-4)

(VII-5)

(VII-6)
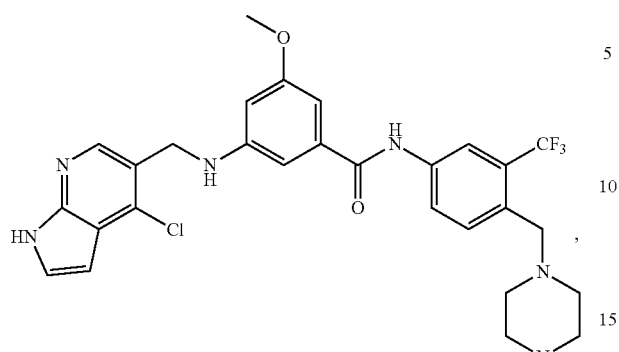
(VII-10)
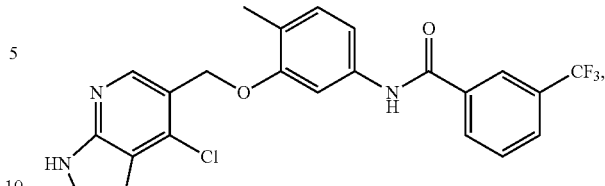
(VII-7)
(VIII-2)
(VII-8)
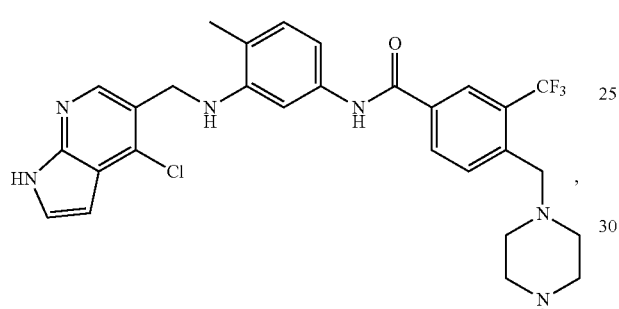
(IX-2)
(VII-9)
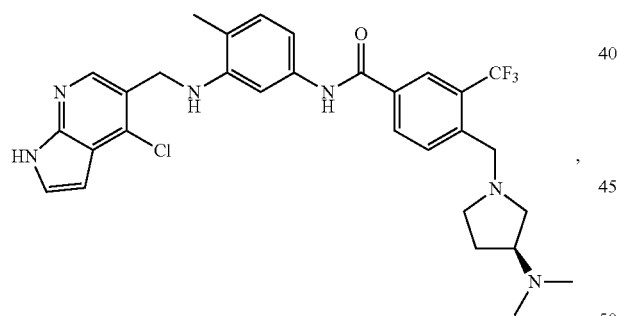
(IX-3)
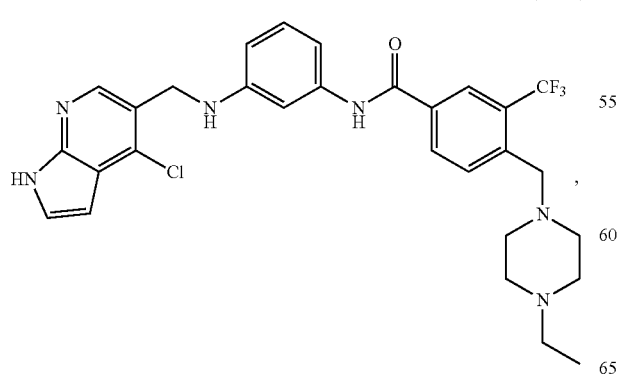

(IX-3)
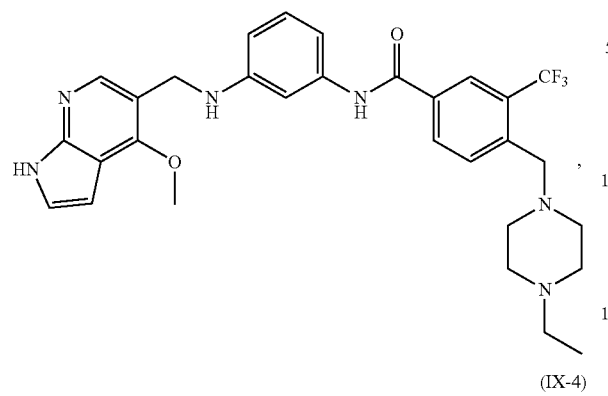
(IX-4)
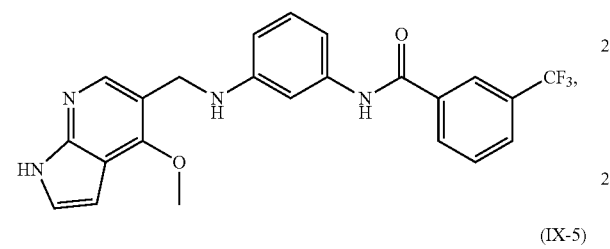
(IX-5)
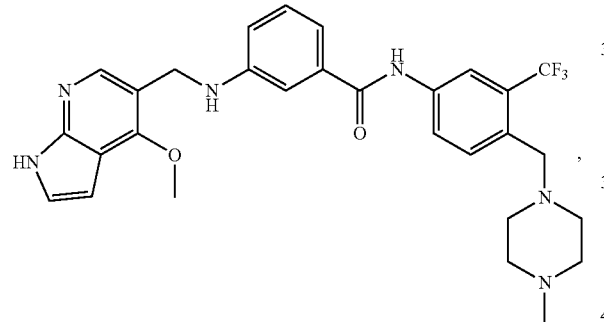
(IX-6)
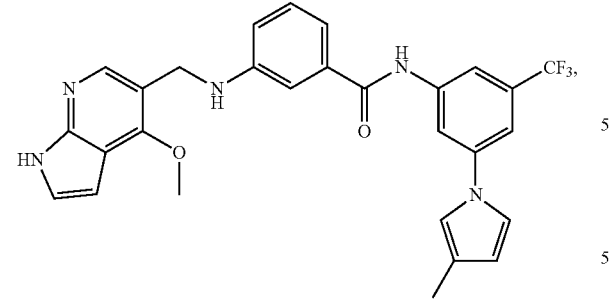
(IX-7)
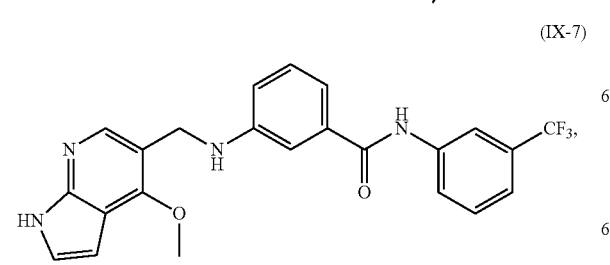
(IX-8)
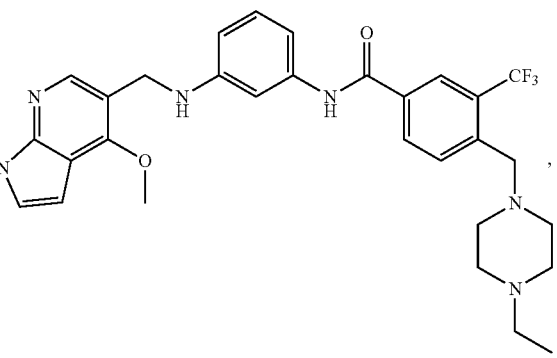
(X-2)
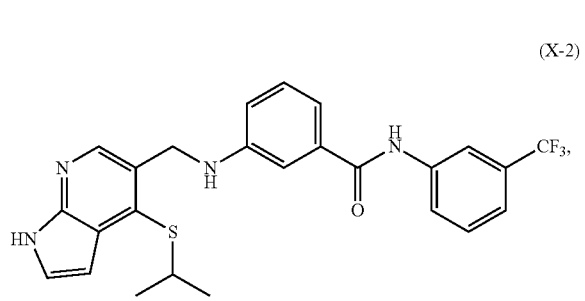
(X-3)
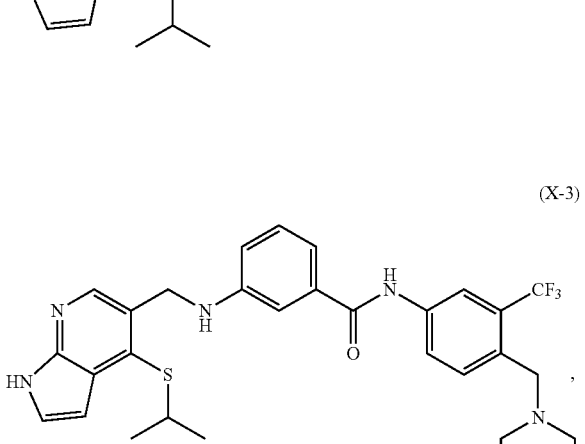
(X-4)
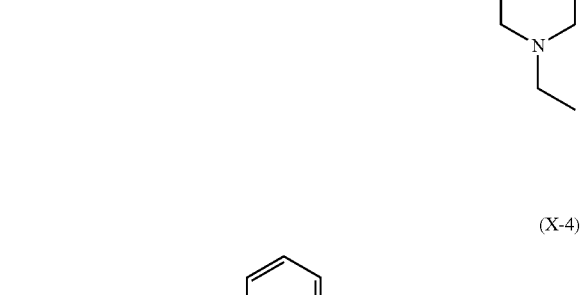
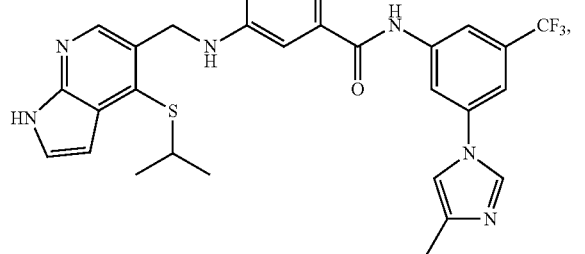

(X-5), (X-6), (XI-1), (XI-2), (XI-3), (XI-4), (XI-5), (XI-6), (XII-2)

(XII-3)
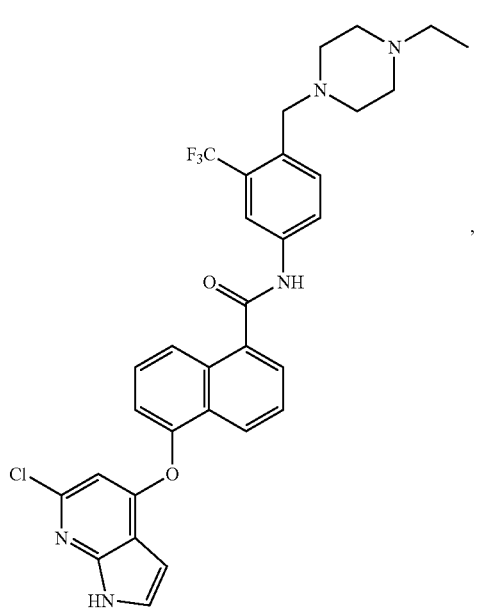
(XII-1)
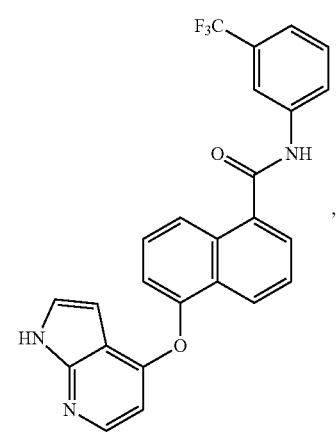
(XII-4)
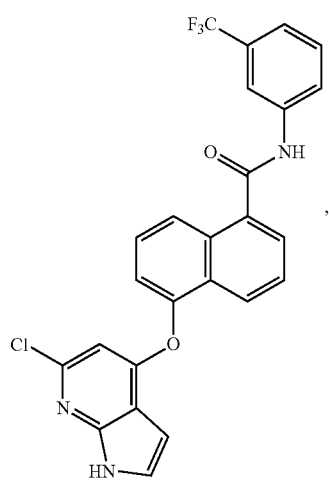
(XII-5)
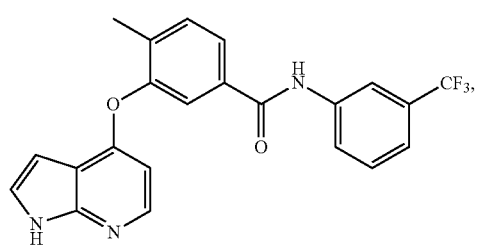
(XII-6)
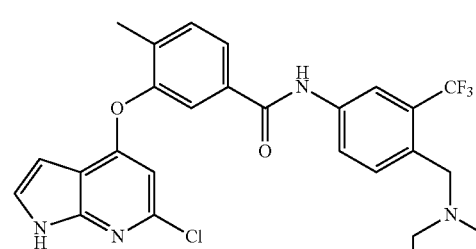
(XII-7)
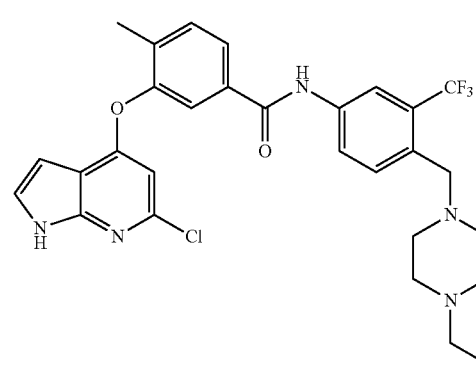
(XIII-2)
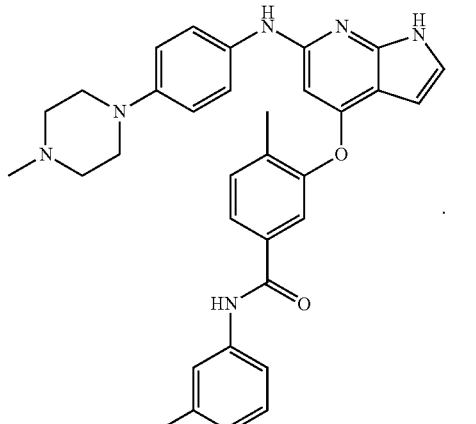
or a pharmaceutically acceptable salt thereof.
7. A pharmaceutical composition comprising a compound of claim 1, or a pharmaceutically acceptable ester, salt, or prodrug thereof, together with a pharmaceutically acceptable carrier.

8. A kit comprising a compound of claim 1, or a pharmaceutically acceptable salt, ester, or prodrug thereof, capable of inhibiting b-raf or b-raf mutation activity; and instructions for use in treating cancer.

* * * * *

UNITED STATES PATENT AND TRADEMARK OFFICE
CERTIFICATE OF CORRECTION

PATENT NO. : 9,180,127 B2
APPLICATION NO. : 13/519826
DATED : November 10, 2015
INVENTOR(S) : Nathanael S. Gray et al.

Page 1 of 1

It is certified that error appears in the above-identified patent and that said Letters Patent is hereby corrected as shown below:

Claims

In claim 1, at column 88, lines 48, the text reading "each of which may be is" should read -- each of which is --.

In claim 6, at column 90, lines 44-52, please replace the formula:

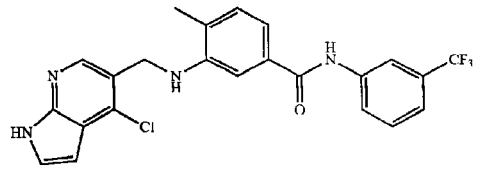 with the formula: 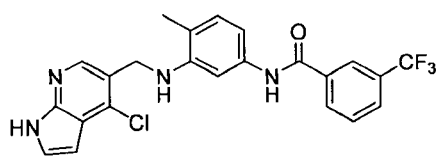

In claim 6, at column 92, line 51, please delete the text: "(IX-3)".

In claim 6, at column 93, line 3, please delete the text: "(IX-3)".

In claim 6, at column 93, lines 45-52, please replace the formula:

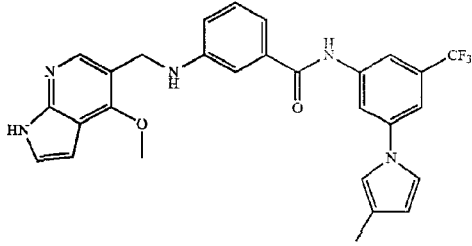 with the formula: 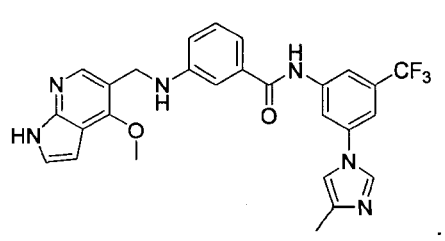

Signed and Sealed this
Fourteenth Day of June, 2016

Michelle K. Lee
*Director of the United States Patent and Trademark Office*